US011355714B2

(12) United States Patent
Parham et al.

(10) Patent No.: US 11,355,714 B2
(45) Date of Patent: Jun. 7, 2022

(54) MATERIALS FOR ORGANIC ELECTROLUMINESCENT DEVICES

(71) Applicant: Merck Patent GmbH, Darmstadt (DE)

(72) Inventors: Amir Hossain Parham, Frankfurt am Main (DE); Tobias Grossmann, Darmstadt (DE); Jonas Valentin Kroeber, Frankfurt am Main (DE)

(73) Assignee: MERCK PATENT GMBH, Darmstadt (DE)

( * ) Notice: Subject to any disclaimer, the term of this patent is extended or adjusted under 35 U.S.C. 154(b) by 279 days.

(21) Appl. No.: 15/770,979

(22) PCT Filed: Oct. 6, 2016

(86) PCT No.: PCT/EP2016/001655
§ 371 (c)(1),
(2) Date: Apr. 25, 2018

(87) PCT Pub. No.: WO2017/071791
PCT Pub. Date: May 4, 2017

(65) Prior Publication Data
US 2019/0058133 A1 Feb. 21, 2019

(30) Foreign Application Priority Data
Oct. 27, 2015 (EP) .................... 15191568

(51) Int. Cl.
| | | |
|---|---|---|
| *H01L 51/00* | (2006.01) | |
| *C07D 333/76* | (2006.01) | |
| *C07D 409/04* | (2006.01) | |
| *C07D 307/91* | (2006.01) | |
| *C07D 407/04* | (2006.01) | |
| *C07D 405/04* | (2006.01) | |
| *C09K 11/06* | (2006.01) | |
| *H01L 51/50* | (2006.01) | |

(52) U.S. Cl.
CPC ........ *H01L 51/0073* (2013.01); *C07D 307/91* (2013.01); *C07D 333/76* (2013.01); *C07D 405/04* (2013.01); *C07D 407/04* (2013.01); *C07D 409/04* (2013.01); *C09K 11/06* (2013.01); *H01L 51/0054* (2013.01); *H01L 51/0056* (2013.01); *H01L 51/0058* (2013.01); *H01L 51/0072* (2013.01); *H01L 51/0074* (2013.01); *C09K 2211/1018* (2013.01); *H01L 51/5012* (2013.01); *H01L 51/5016* (2013.01); *H01L 51/5072* (2013.01); *H01L 51/5096* (2013.01); *Y02E 10/549* (2013.01)

(58) Field of Classification Search
CPC ... H01L 51/5012–5016; H01L 51/5072–5084; H01L 51/5096; H01L 51/5048–506; H01L 51/50–56
See application file for complete search history.

(56) References Cited

U.S. PATENT DOCUMENTS

| | | | |
|---|---|---|---|
| 2011/0315965 A1 | 12/2011 | Takashima et al. | |
| 2012/0112179 A1* | 5/2012 | Mizuki | C07D 307/91 257/40 |
| 2012/0119196 A1 | 5/2012 | Ogiwara et al. | |
| 2013/0306960 A1* | 11/2013 | Yamamoto | H01L 51/5028 257/40 |
| 2015/0108449 A1* | 4/2015 | Huang | C07F 9/5325 548/310.7 |
| 2016/0218299 A1 | 7/2016 | Haketa et al. | |

FOREIGN PATENT DOCUMENTS

| | | |
|---|---|---|
| CN | 102265424 A | 12/2011 |
| TW | 201114320 A | 4/2011 |
| WO | 02/85822 A1 | 10/2002 |
| WO | WO-2006128800 A1 | 12/2006 |
| WO | 2008/059713 A1 | 5/2008 |
| WO | 2010/074087 A1 | 7/2010 |
| WO | WO-2011033978 A1 | 3/2011 |
| WO | WO-2015050173 A1 | 4/2015 |

OTHER PUBLICATIONS

International Search Report for PCT/EP2016/001655 dated Nov. 14, 2016.
Kumar, S., et al., "High $T_g$ fluoranthene-based electron transport materials for organic light-emitting diodes", New Journal of Chemistry, vol. 39, No. 8, (2015), pp. 6351-6357.
Written Opinion of the International Searching Authority for PCT/EP2016/001655 dated Nov. 14, 2016.

* cited by examiner

*Primary Examiner* — William E McClain
(74) *Attorney, Agent, or Firm* — Faegre Drinker Biddle & Reath LLP

(57) ABSTRACT

The present invention relates to compounds comprising a heterocyclic group substituted with a fluoranthene group and a particular aromatic or heteroaromatic group. The compounds are suitable for use in electronic devices, in particular organic electroluminescent devices, comprising these compounds. In some embodiments, the compounds are used as matrix materials for phosphorescent or fluorescent emitters as well as a hole-blocking or an electron-transport layer.

11 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2016/001655, filed Oct. 6, 2016, which claims benefit of European Application No. 15191568.3, filed Oct. 27, 2015, both of which are incorporated herein by reference in their entirety.

The present invention relates to materials for use in electronic devices, in particular in organic electroluminescent devices, and to electronic devices, in particular organic electroluminescent devices, comprising these materials.

The structure of organic electroluminescent devices (OLEDs) in which organic semiconductors are employed as functional materials is described, for example, in U.S. Pat. Nos. 4,539,507, 5,151,629, EP 0676461 and WO 98/27136. The emitting materials employed here are increasingly organometallic complexes which exhibit phosphorescence instead of fluorescence. For quantum-mechanical reasons, an up to four-fold increase in the energy and power efficiency is possible using organometallic compounds as phosphorescence emitters. In general, however, there is still a need for improvement in the case of OLEDs, in particular also in the case of OLEDs which exhibit triplet emission (phosphorescence), for example with respect to efficiency, operating voltage and lifetime.

The properties of phosphorescent OLEDs are not only determined by the triplet emitters employed. In particular, the other materials used, such as matrix materials, hole-blocking materials, electron-transport materials, hole-transport materials and electron- or exciton-blocking materials, are also of particular importance here. Improvements in these materials can thus also result in significant improvements in the OLED properties, particularly with respect to the efficiency, the lifetime and the thermal stability of the materials.

The object of the present invention is the provision of compounds which are suitable for use in an OLED, in particular as matrix material for phosphorescent emitters, but also as hole-blocking material, as electron-transport material or optionally as a material for a charge generation layer. A further object of the present invention is to provide further organic semiconductors for organic electroluminescent devices so as to provide the person skilled in the art with a greater possible choice of materials for the production of OLEDs.

It is known that compounds with aromatic heterocyclic groups such as dibenzofurans and dibenzothiophenes are useful in OLEDs, generally as hosts for light emitting materials or for their charge-carrying properties. Dibenzofurans or dibenzothiophenes may be substituted with substituents like aromatic or heteroaromatic groups in order to obtain compounds with adapted charge-carrying properties.

EP 2372803, CN 102850334, EP 1885818 describe OLED comprising compounds with aromatic groups, heteroaromatic groups or arylamines groups, which are bonded to a dibenzofuran skeleton or to a dibenzothiophene skeleton.

US 2012/0119196, WO 2013/132278, WO2015/050173 and US2015/0108449 describe OLEDs comprising compounds with fluoranthene rings bonded to an aromatic heterocyclic group.

Surprisingly, it has been found that excellent performance data can be achieved with compounds comprising a dibenzofuran or dibenzothiophene group, which is directly bonded to a fluoranthene skeleton on one side and to a particular aromatic or heteroaromatic group on the other side. More particularly, the compounds of the invention, which are described in greater detail below, are highly suitable for use in OLEDs and result in improvements in the organic electroluminescent device in terms of efficiency, lifetime and/or operating voltage. The improvements here relate, in particular, to the luminous efficacy. More particularly, OLEDs comprising the compounds of the invention as matrix material or host in the emitting layers for red or yellow phosphorescent emitters (Triplet state T1 between 2.4 and 1.8 eV) exhibit improved properties in terms of luminous efficacy while maintaining very good properties in terms of operating voltage and lifetime. The present invention therefore relates to these compounds and to electronic devices, in particular organic electroluminescent devices, which comprise compounds of the type described below.

The present invention thus relates to a compound of formula (1) or (2),

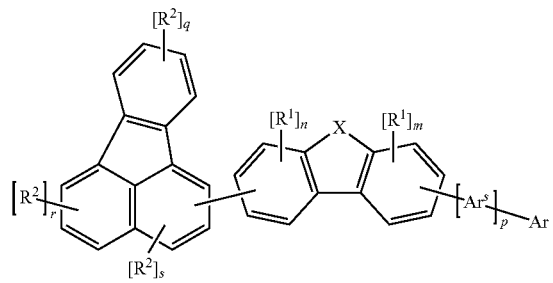

formula (1)

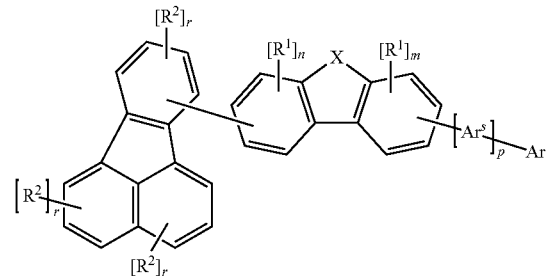

formula (2)

where the following applies to the symbols and indices used:

X is O or S;

$Ar^S$ is an aromatic or heteroaromatic ring system having 5 to 30 aromatic ring atoms, which may in each case also be substituted by one or more radicals $R^3$;

Ar is a condensed aryl group having 10 to 40 aromatic ring atoms, which may in each case be substituted by one or more radicals $R^3$; or Ar is a group of formula (Ar-1),

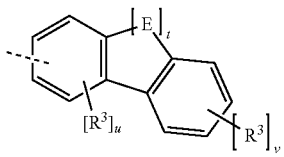

formula (Ar-1)

with the proviso that Ar is not a fluoranthene; and where the dashed line represents the bond to $Ar^S$ or, if $Ar^S$ is absent, to the phenyl group of the heterocycle comprising X as depicted in formula (1) or (2);

E is O, S, $C(R^0)_2$, wherein when t is 0 then the divalent bridge E is absent;

$R^0$, $R^1$, $R^2$, $R^3$ are on each occurrence, identically or differently, H, D, F, Cl, Br, I, CHO, $C(\!=\!\!O)Ar^1$, $P(\!=\!\!O)(Ar^1)_2$, $S(\!=\!\!O)Ar^1$, $S(\!=\!\!O)_2Ar^1$, $(R^4)C\!=\!\!C(R^4)Ar^1$, CN, $NO_2$, $N(R^4)_2$, $Si(R^4)_3$, $B(OR^4)_2$, $B(R^4)_2$, $B(N(R^4)_2)_2$, $OSO_2R^4$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^4$, where one or more, preferably non-adjacent $CH_2$ groups may be replaced by $(R^4)C\!=\!\!C(R^4)$, $C\!\equiv\!\!C$, $Si(R^4)_2$, $Ge(R^4)_2$, $Sn(R^4)_2$, $C\!=\!\!O$, $C\!=\!\!S$, $C\!=\!\!Se$, $P(\!=\!\!O)(R^4)$, SO, $SO_2$, $N(R^4)$, O, S or $CON(R^4)$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^4$, or an aryloxy or heteroaryloxy group having 5 to 60 aromatic ring atoms, which may be substituted by one or more radicals $R^4$; two adjacent substituents $R^0$, two or more adjacent substituents $R^1$, two or more adjacent substituents $R^2$ and/or two or more adjacent substituents $R^3$ may also form a mono- or polycyclic, aliphatic or aromatic or heteroaromatic ring system with one another;

$Ar^1$ is on each occurrence, identically or differently, an aromatic or heteroaromatic ring system having 5 to 24 aromatic ring atoms, which may in each case be substituted by one or more radicals $R^4$;

$R^4$ is on each occurrence, identically or differently selected from the group consisting of H, D, F, Cl, Br, I, CN, $Si(R^5)_3$, a straight-chain alkyl, alkoxy or thioalkyl group having 1 to 40 C atoms or a branched or cyclic alkyl, alkoxy or thioalkyl with 3-40 C atoms which may be substituted by one or more radicals $R^5$, wherein each one or more non-adjacent $CH_2$ groups by may be replaced $C(R^5)\!=\!\!C(R^5)$, $Si(R^5)_2$, $C\!=\!\!NR^5$, $P(\!=\!\!O)(R^5)$, SO, $SO_2$, $NR^5$, O, S or $CONR^5$ and where one or more H atoms may be replaced by D, F, Cl, Br or I, an aromatic or heteroaromatic ring system having 6 to 40 carbon atoms which may be substituted by one or more radicals $R^5$, an aryloxy group having 5 to 40 aromatic ring atoms which may be substituted by one or more radicals $R^5$, or an aralkyl group having 5 to 40 aromatic ring atoms which may be substituted by one or more radicals $R^5$, where optionally two or more adjacent substituents $R^4$ can form a mono- or polycyclic, aliphatic, aromatic or heteroaromatic ring system with one another;

$R^5$ is selected from the group consisting of H, D, F, an aliphatic hydrocarbon radical having 1 to 20 carbon atoms or an aromatic or heteroaromatic ring system having 5 to 30 C atoms, wherein two or more adjacent substituents $R^5$ can form a mono- or polycyclic, aliphatic, aromatic or heteroaromatic ring system with one another;

m, n, r, u are each, identically or differently, 0, 1, 2 or 3;
p, t are each, identically or differently, 0 or 1;
q, v are each, identically or differently, 0, 1, 2, 3 or 4;
s is 0, 1 or 2.

For the purposes of the present application, the following definitions of chemical groups apply:

An aryl group in the sense of this invention contains 6 to 60 aromatic ring atoms; a heteroaryl group in the sense of this invention contains 5 to 60 aromatic ring atoms, at least one of which is a heteroatom. Preferably, a heteroaryl group does not contain more than 3 heteroatoms in a ring. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or CH$_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, for the purposes of the present application, intended to be taken to mean, inter alia, that the two radicals are linked to one another by a chemical bond. This is illustrated by the following schemes:

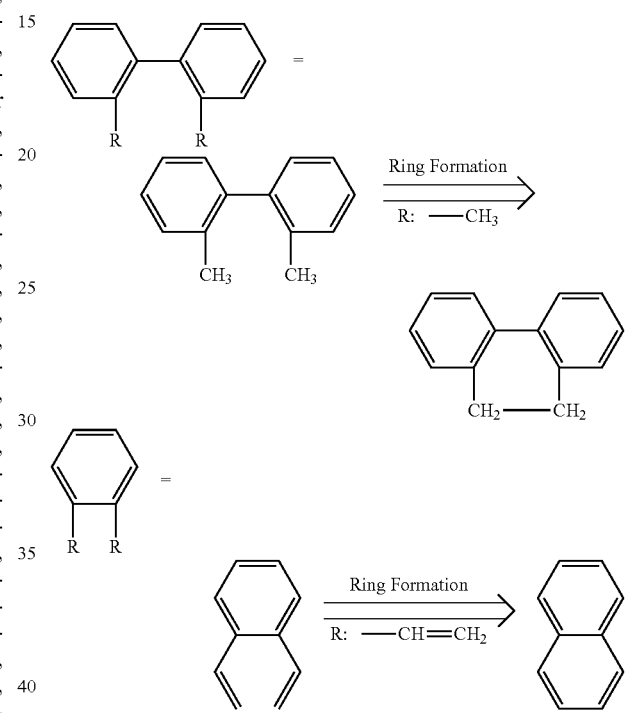

Furthermore, however, the above-mentioned formulation is also intended to be taken to mean that, in the case where one of the two radicals represents hydrogen, the second radical was bonded at the position to which the hydrogen atom was bonded, with formation of a ring. This is illustrated by the following scheme:

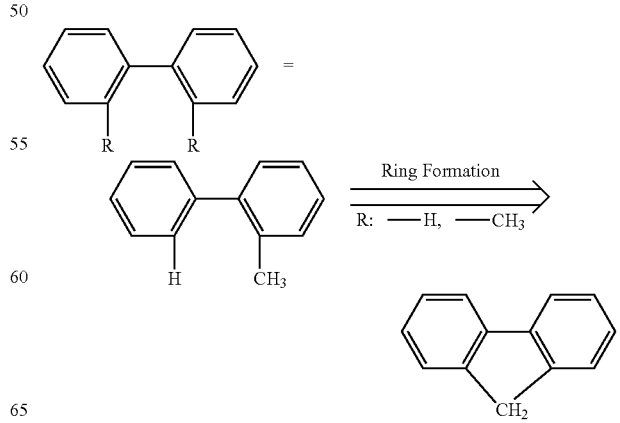

In accordance with a preferred embodiment, p is equal to 0 so that $Ar^S$ is absent and Ar is directly bonded to the phenyl group of the heterocycle comprising X as depicted in formula (1) or (2).

If p=1, the group $Ar^S$ is preferably selected from aromatic or heteroaromatic ring systems having 5 to 18 aromatic ring atoms, which may in each case also be substituted by one or more radicals $R^3$.

Particularly preferable groups $Ar^S$ are selected from the groups of formulae ($Ar^S$-1) to ($Ar^S$-13) below:

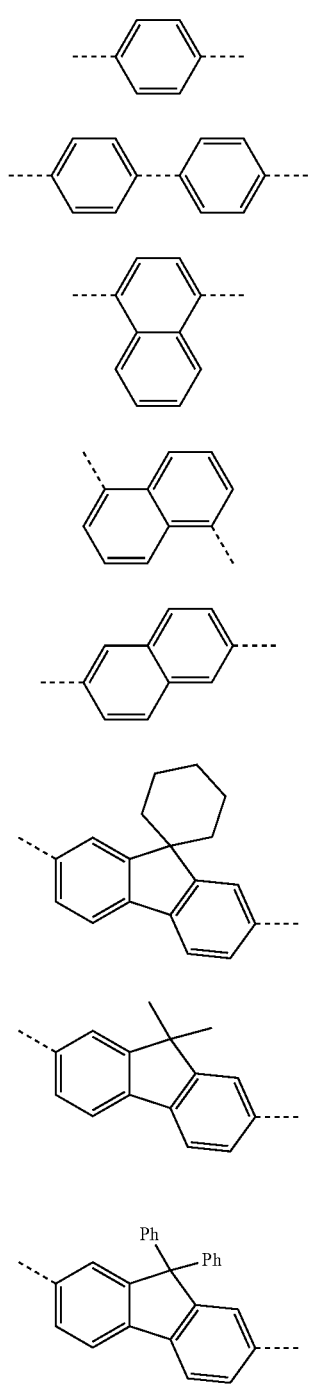

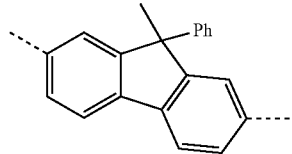

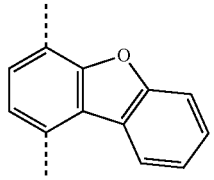

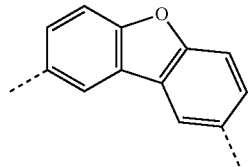

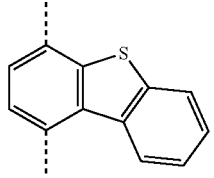

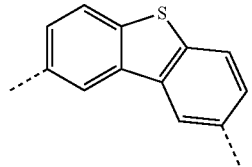

where the dashed bonds indicates the bonds to the phenyl group of the heterocycle comprising X and to the group Ar as depicted in formula (1) or (2), and where the groups may be substituted at each free position by a group $R^3$, but are preferably unsubstituted.

In a preferred embodiment of the invention, the compounds of formula (1) or (2) are selected from the compounds of formulae (1-1) or (2-1), formula (1-1)

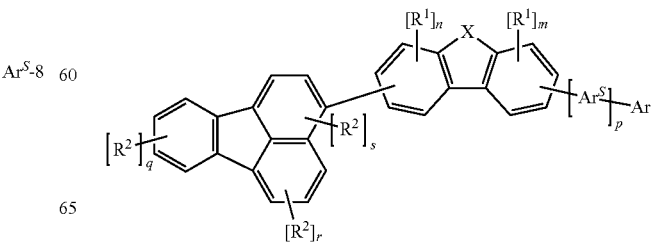

formula (2-1)
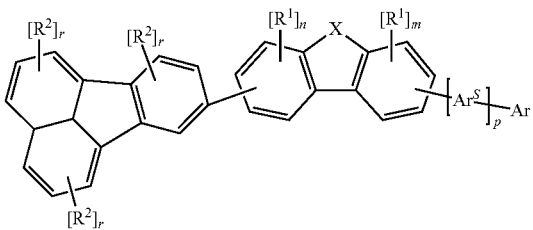
where the symbols and indices used have the same meanings as above.
In a particularly preferred embodiment of the invention, the compounds of formula (1-1) or (2-1) are selected from the compounds of the following formulae (1-1-1) to (2-1-4),
formula (1-1-1)
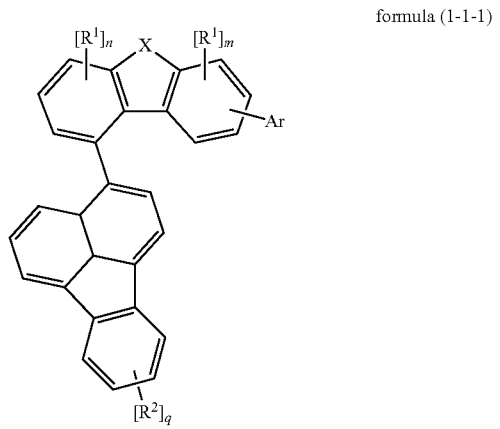
formula (1-1-2)
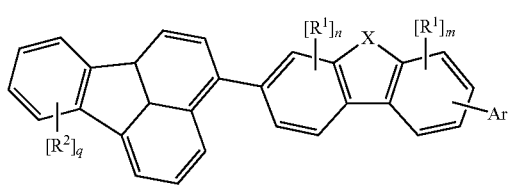
formula (1-1-3)
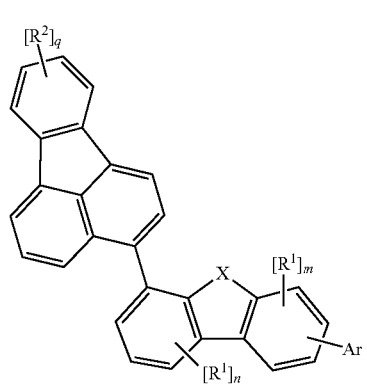
formula (1-1-4)
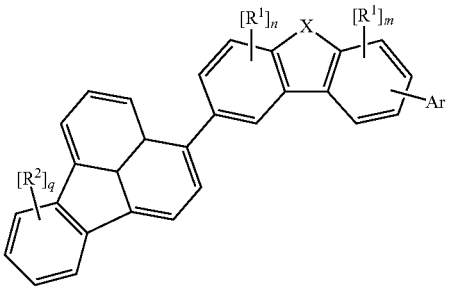
formula (2-1-1)
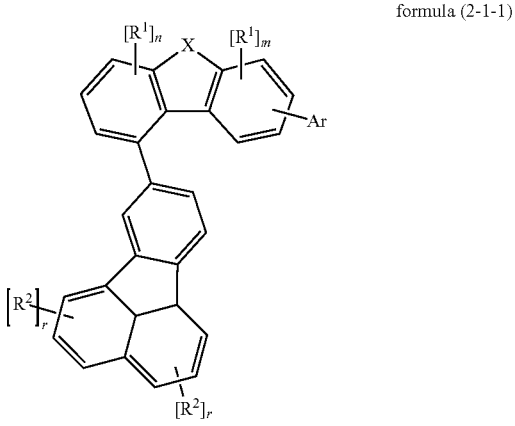
formula (2-1-2)
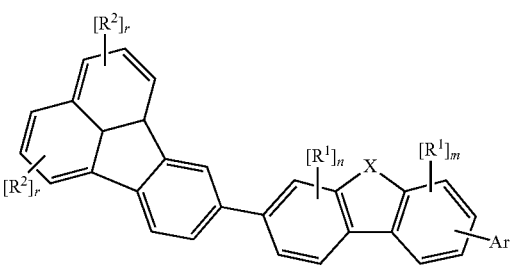
formula (2-1-3)
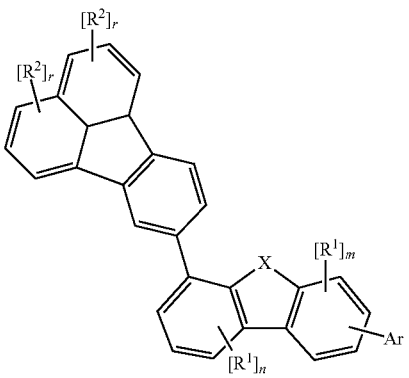

formula (2-1-4)
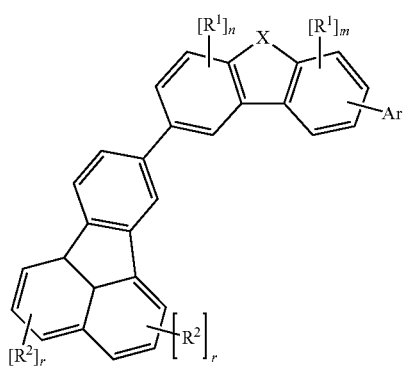
where the symbols and indices used have the same meanings as above.
In a very particularly preferred embodiment of the invention, the compounds of formula (1-1-1) to (2-1-4) are selected from the compounds of the following formulae (1-1-1-a) to (2-1-4-d),
formula (1-1-1-a)
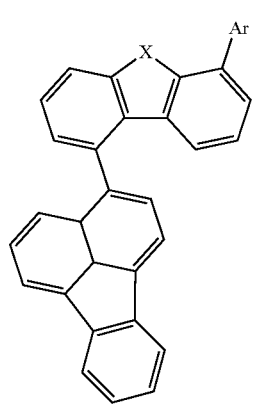
formula (1-1-1-b)
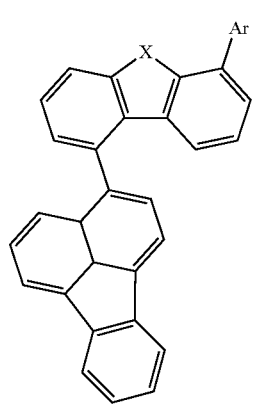
formula (1-1-1-c)
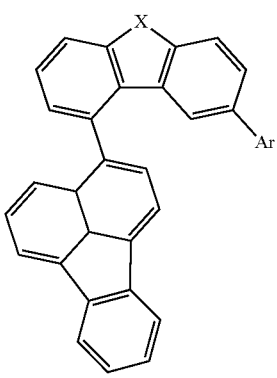
formula (1-1-1-d)
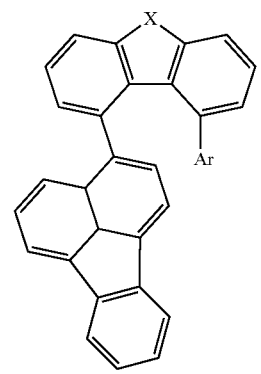
formula (1-1-2-a)
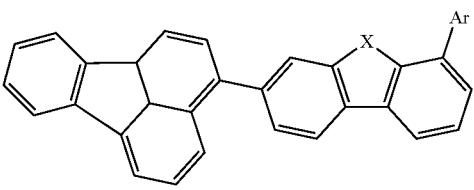
formula (1-1-2-b)
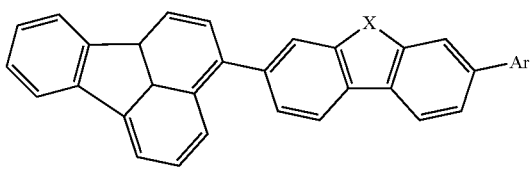
formula (1-1-2-c)
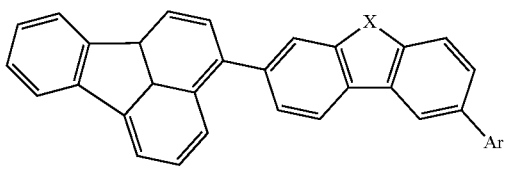
formula (1-1-2-d)
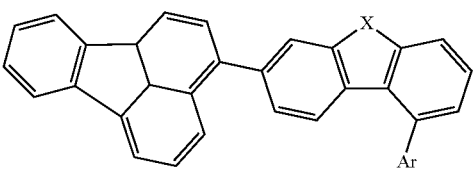

formula (1-1-3-a)
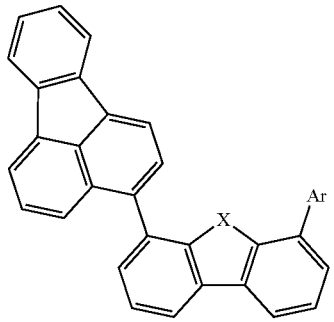
formula (1-1-4-a)
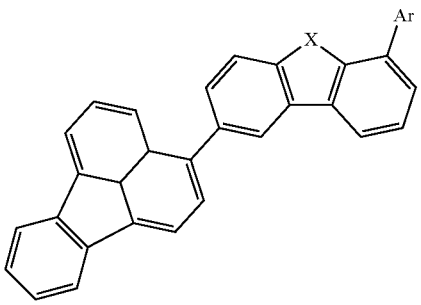
formula (1-1-3-b)
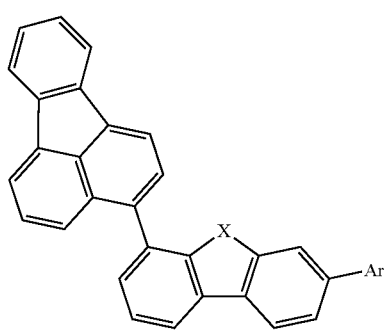
formula (1-1-4-b)
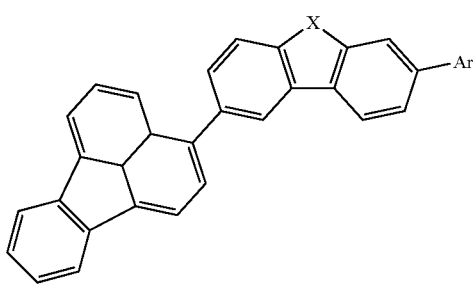
formula (1-1-3-c)
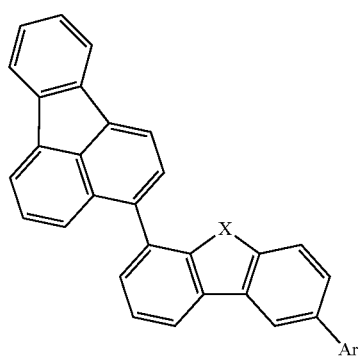
formula (1-1-4-c)
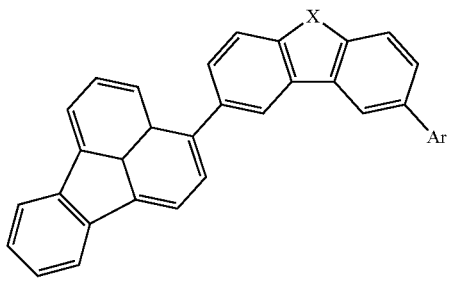
formula (1-1-4-d)
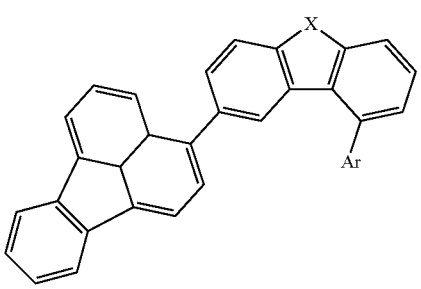
formula (1-1-3-d)
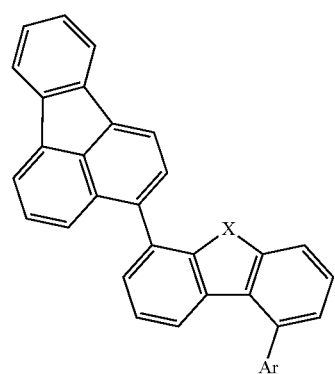
formula (2-1-1-a)
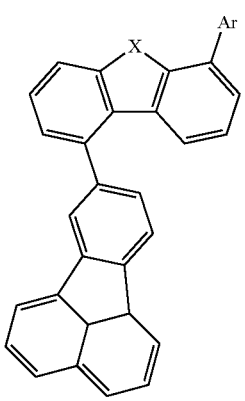

formula (2-1-1-b)
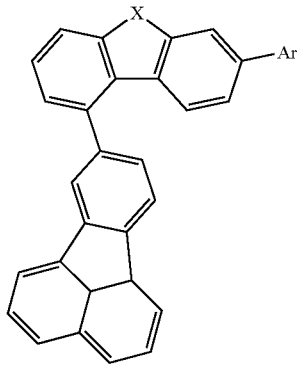
formula (2-1-1-c)
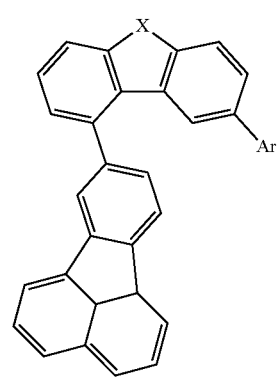
formula (2-1-1-d)
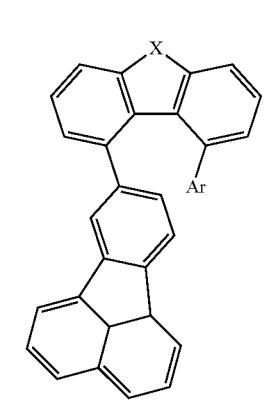
formula (2-1-2-a)
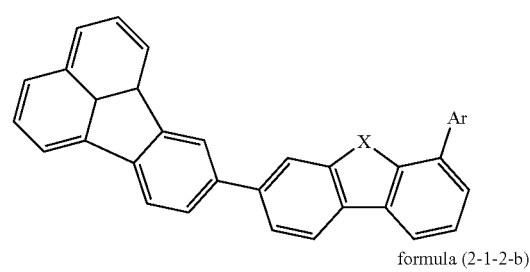
formula (2-1-2-b)
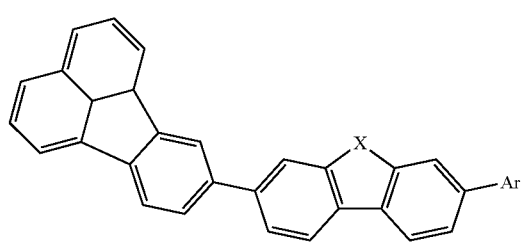
formula (2-1-2-c)
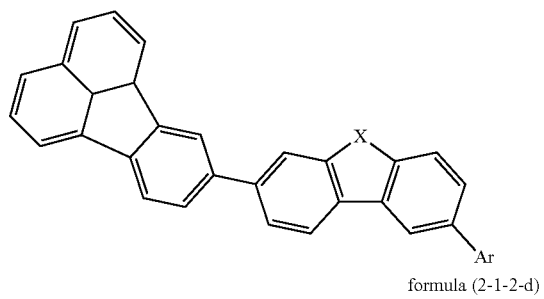
formula (2-1-2-d)
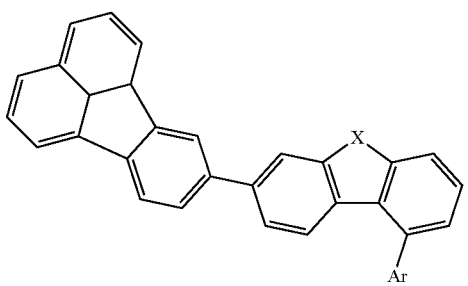
formula (2-1-3-a)
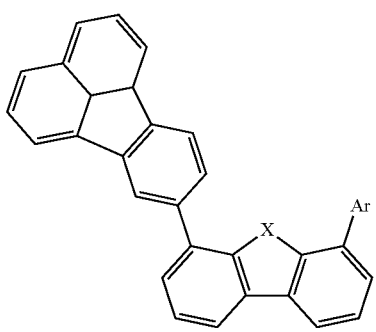
formula (2-1-3-b)
formula (2-1-3-c)
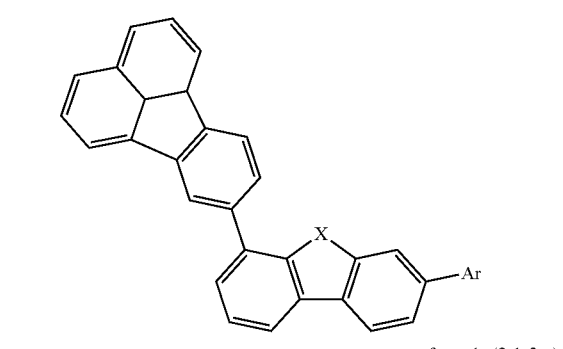

formula (2-1-3-d)

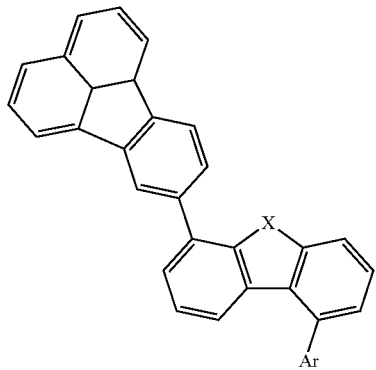

formula (2-1-4-a)

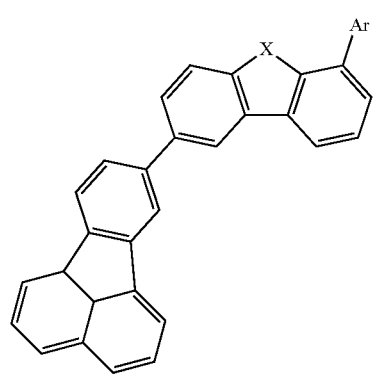

formula (2-1-4-b)

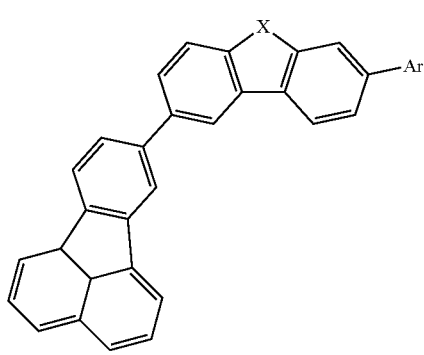

formula (2-1-4-c)

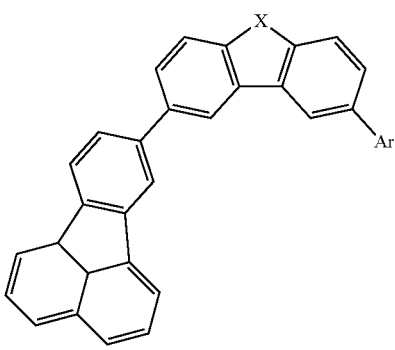

formula (2-1-4-d)

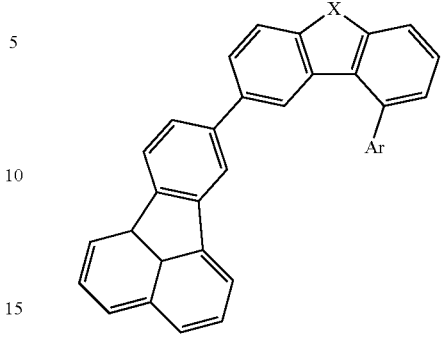

where the symbols and indices used have the same meanings as above.

According to the invention, formula (1) is preferred, formula (1-1) is very preferred, formulae (1-1-1) to (1-1-4) are particularly preferred and formulae (1-1-1-a) to (1-1-4-d) are very particularly preferred.

The group Ar in formulae (1), (2), (1-1), (2-1), (1-1-1) to (2-1-4) and (1-1-1-a) to (2-1-4-d) is a condensed aryl group having 10 to 40 aromatic ring atoms, more preferably 14 to 40 aromatic rings atoms, which may in each case be substituted by one or more radicals $R^3$; or Ar is a group of formula (Ar-1) as defined above, with the proviso that Ar is not a fluoranthene.

More preferably, the group Ar is selected from the group consisting of naphthalene, anthracene, tetracene, phenanthrene, chrysene, triphenylene, pyrene, perylene, benzophenanthracene, benzopyrene, biphenyl, fluorene, spirobifluorene, dibenzofuran, dibenzothiophene, each of which may be substituted by one or more radical $R^3$. It is particularly preferred that the group Ar is selected from anthracene, phenanthrene, tetracene, chrysene, triphenylene, fluorene, dibenzofuran or dibenzothiophene, each of which may be substituted by one or more radical $R^3$.

Suitable groups Ar are groups of the following formulae (Ar-2) to (Ar-38), where $R^0$ has the same meaning as indicated above and where the groups of formulae (Ar-2) to (Ar-38) may be substituted by one or more radicals $R^3$ as defined above, at any free position.

Ar-2

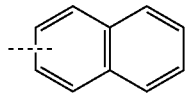

Ar-3

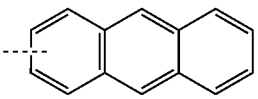

Ar-4

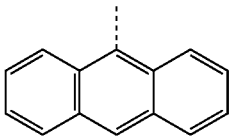

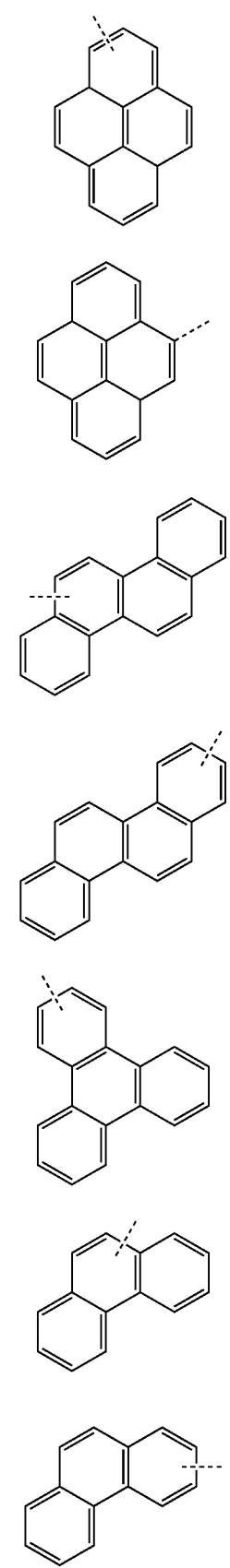

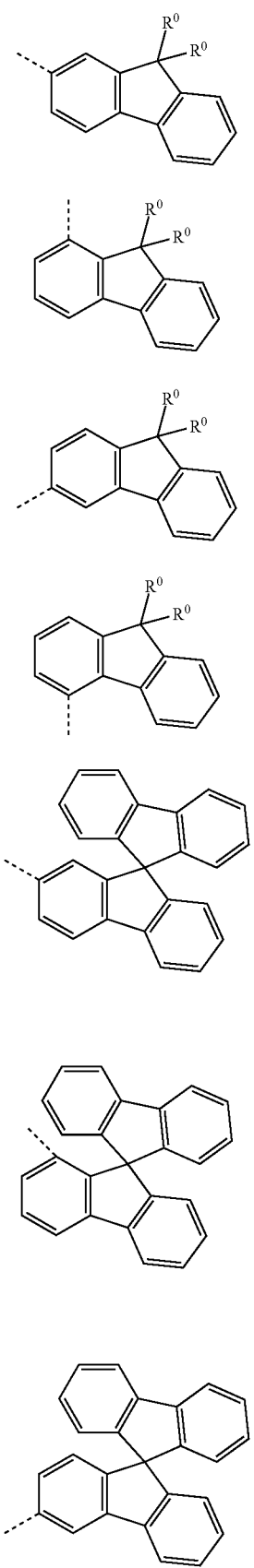

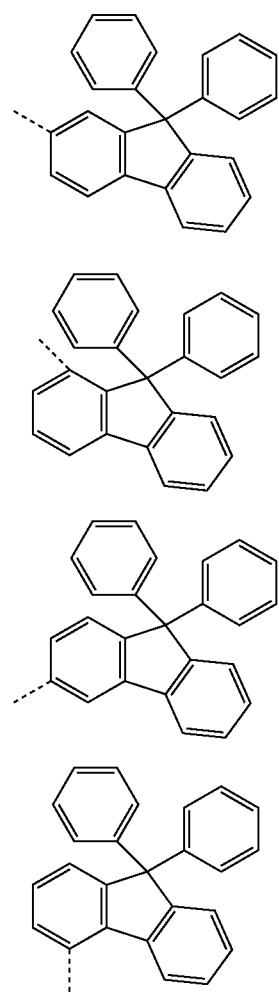

Ar-35

Ar-36

Ar-37

Ar-38

In a preferred embodiment of the invention, $R^1$, $R^2$ and $R^3$ are selected, identically or differently on each occurrence, from the group consisting of H, D, F, CN, a straight-chain alkyl or alkoxy group having 1 to 10 C atoms or a branched or cyclic alkyl or alkoxy group having 3 to 10 C atoms, each of which may be substituted by one or more radicals $R^4$, where one or more non-adjacent $CH_2$ groups may be replaced by O and where one or more H atoms may be replaced by F, an aromatic or heteroaromatic ring system having 5 to 24 aromatic ring atoms, which may in each case be substituted by one or more radicals $R^4$.

In a more preferred embodiment of the invention, $R^1$, $R^2$ and $R^3$ are selected, identically or differently on each occurrence, from the group consisting of H, D, F, CN, a straight-chain alkyl group having 1 to 5 C atoms or a branched or cyclic alkyl group having 3 to 5 C atoms, each of which may be substituted by one or more radicals $R^4$, where one or more H atoms may be replaced by F, an aryl or heteroaryl group having 5 to 14 aromatic ring atoms, which may in each case be substituted by one or more radicals $R^4$.

In a particularly preferred embodiment of the invention, $R^1$, $R^2$ and $R^3$ are selected, identically or differently on each occurrence, from the group consisting of H, D, F, CN, methyl, t-butyl, phenyl or naphthyl, each of which may be substituted by one or more radicals $R^4$.

In a preferred embodiment of the invention, $R^0$ is selected on each occurrence, identically or differently, from the group consisting of H, D, F, CN, a straight-chain alkyl or alkoxy group having 1 to 10 C atoms or a branched or cyclic alkyl or alkoxy group having 3 to 10 C atoms, each of which may be substituted by one or more radicals $R^4$, where in each case one or more non-adjacent $CH_2$ groups may be replaced by O and where one or more H atoms may be replaced by D, F or CN, an aromatic or heteroaromatic ring system having 5 to 24 aromatic ring atoms, which may in each case be substituted by one or more radicals $R^4$, where two substituents $R^0$ may optionally form a mono- or polycyclic, aliphatic or aromatic or heteroaromatic ring system.

More preferably, $R^0$ is selected on each occurrence, identically or differently, from the group consisting of H, a straight-chain alkyl having 1 to 5 C atoms or a branched or cyclic alkyl group having 3 to 5 C atoms, each of which may be substituted by one or more radicals $R^4$, where one or more H atoms may be replaced by F, an aryl or heteroaryl group having 5 to 14 aromatic ring atoms, which may in each case be substituted by one or more radicals $R^4$, where two substituents $R^0$ may optionally form a mono- or polycyclic, aliphatic or aromatic or heteroaromatic ring system, which may be substituted by one or more radicals.

It is particularly preferred that $R^0$ is methyl or phenyl.

For compounds which are processed by vacuum evaporation, the alkyl groups preferably have not more than four C atoms, particularly preferably not more than 1 C atom. For compounds which are processed from solution, suitable compounds are also those which are substituted by linear, branched or cyclic alkyl groups having up to 10 C atoms or which are substituted by oligoarylene groups, for example ortho-, meta-, para- or branched terphenyl or quaterphenyl groups.

The following examples represent some compounds according to formula (1) or (2):

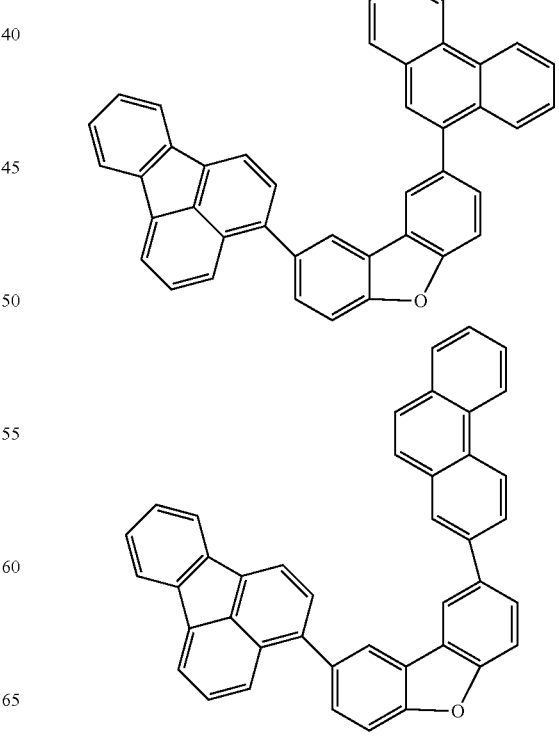

25
-continued
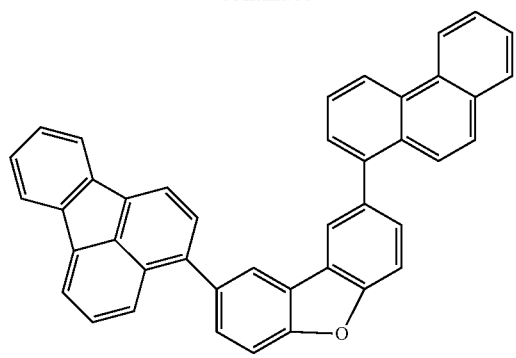
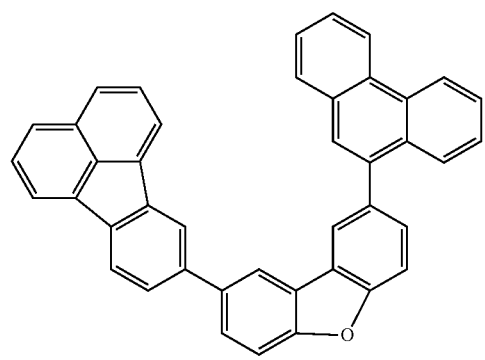
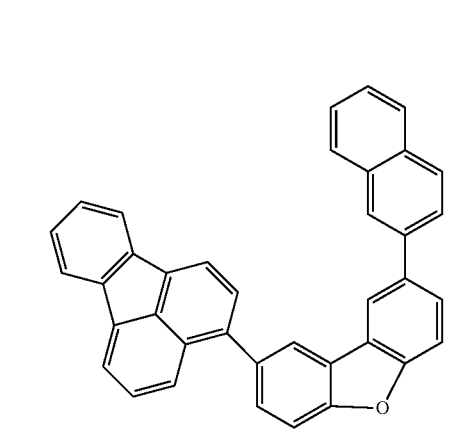
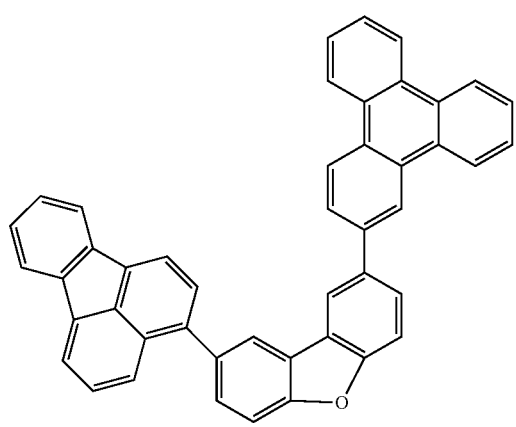
26
-continued
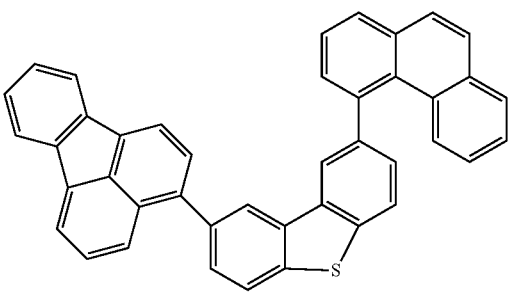
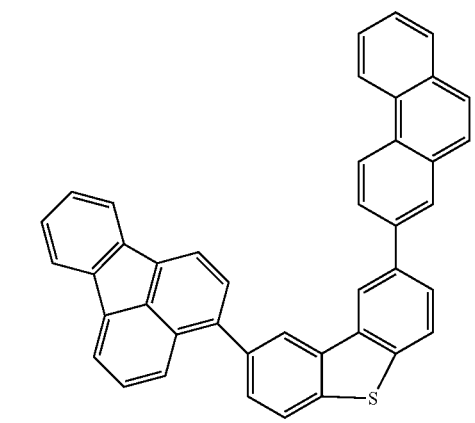
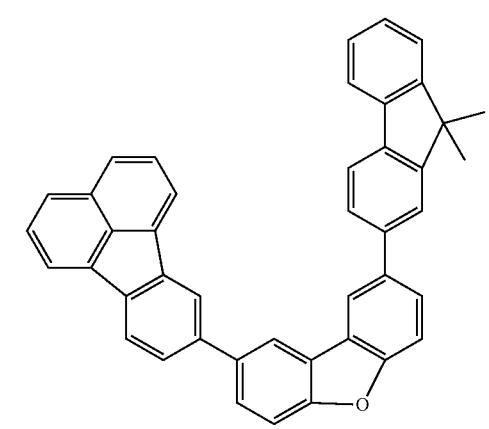

27
-continued
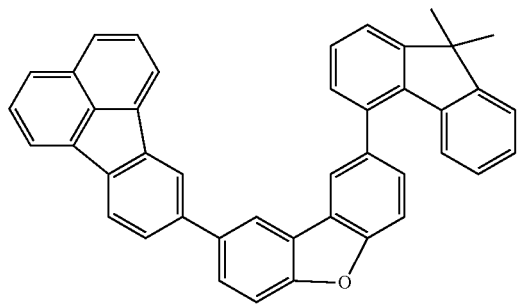
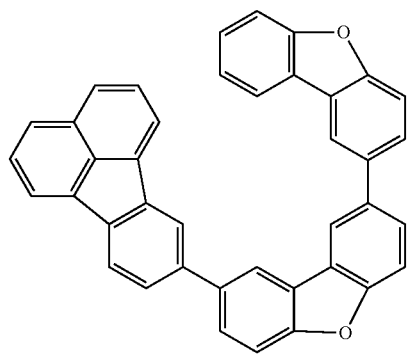
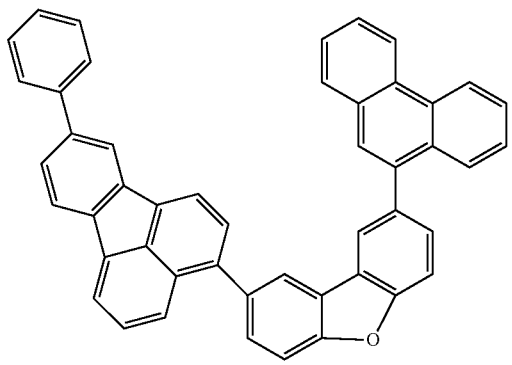
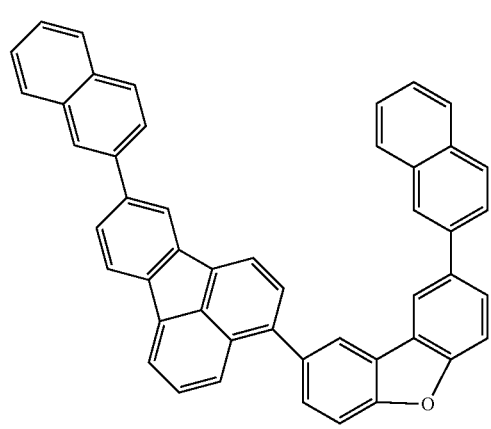
28
-continued
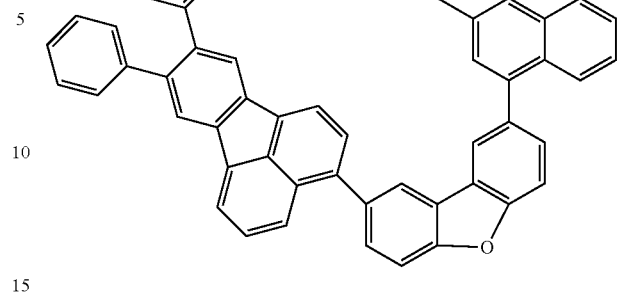
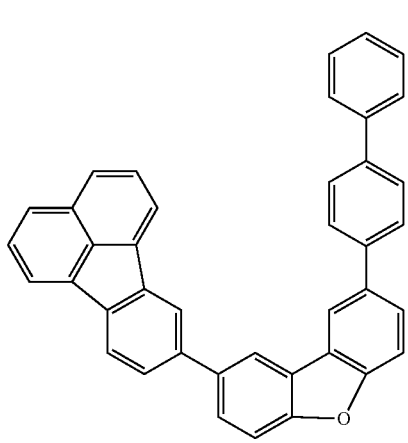
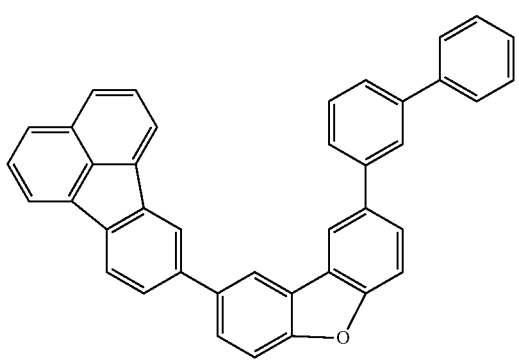
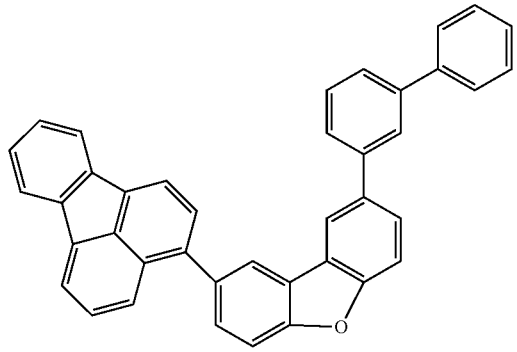

29
-continued
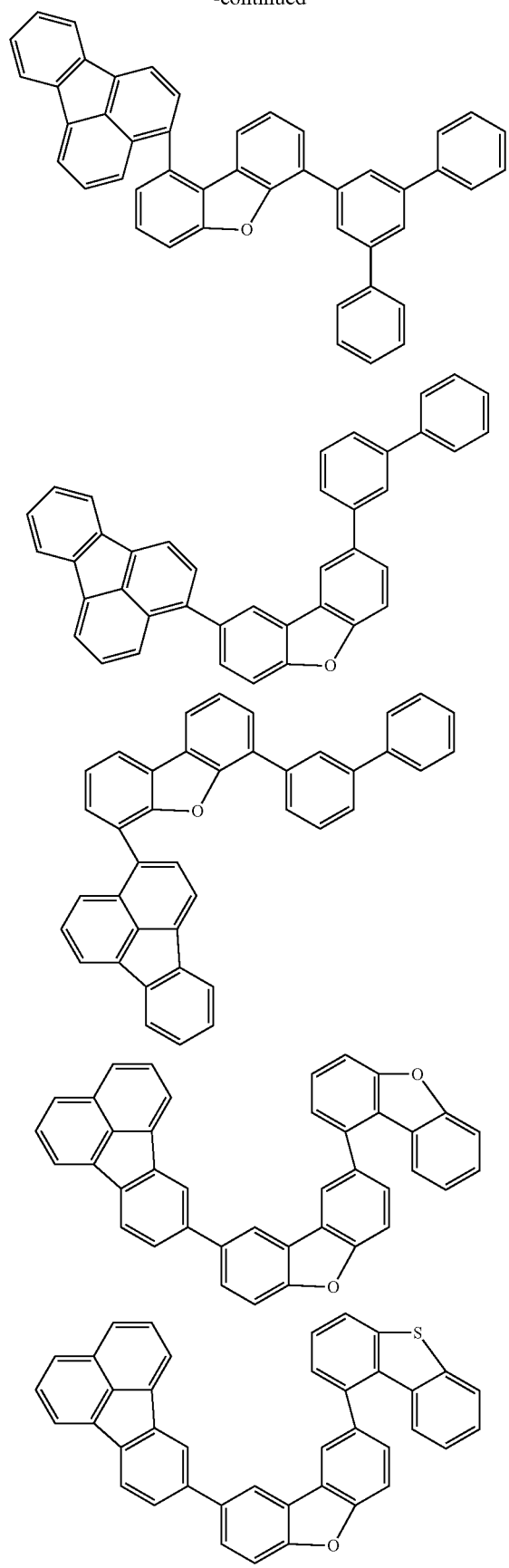
30
-continued
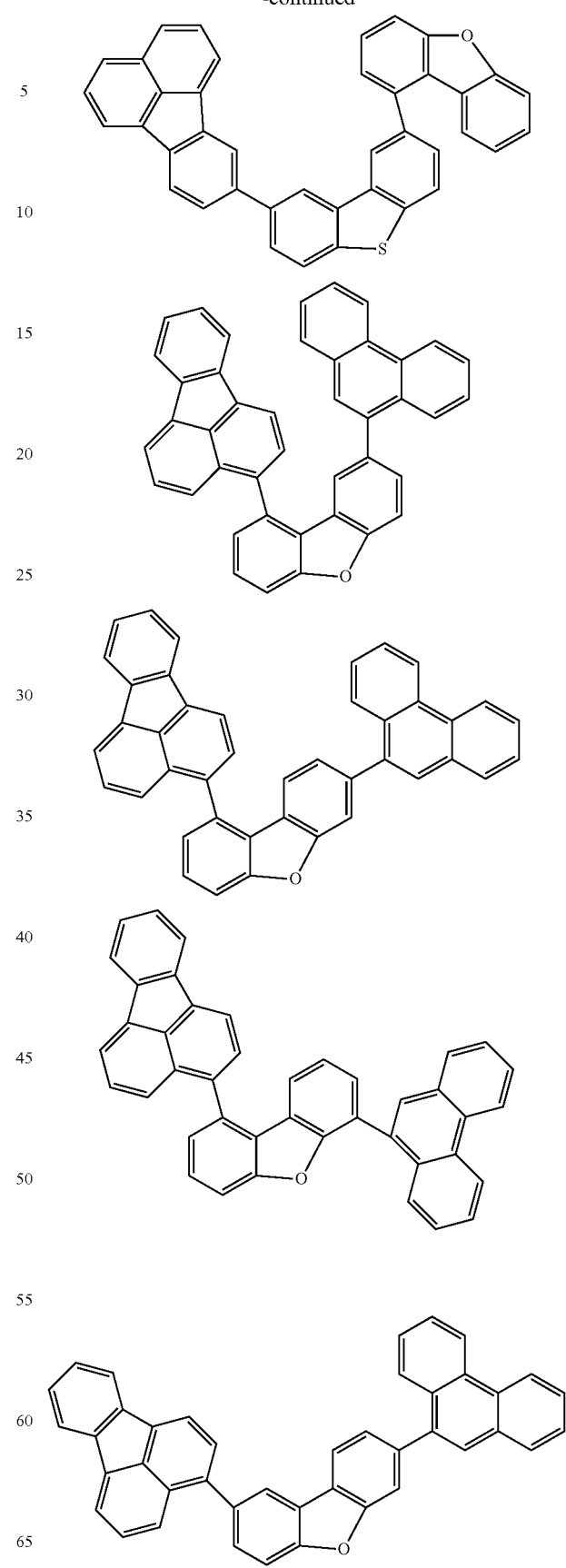

31
-continued
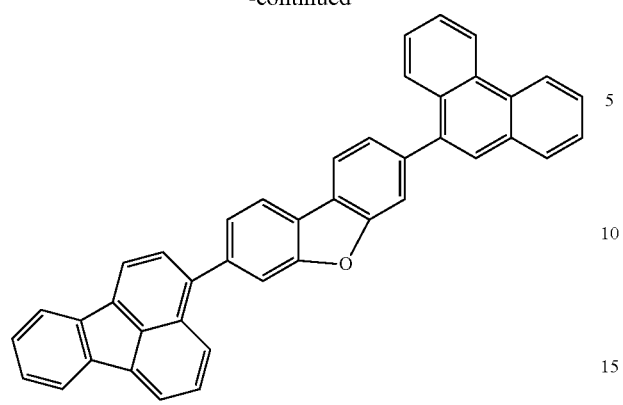
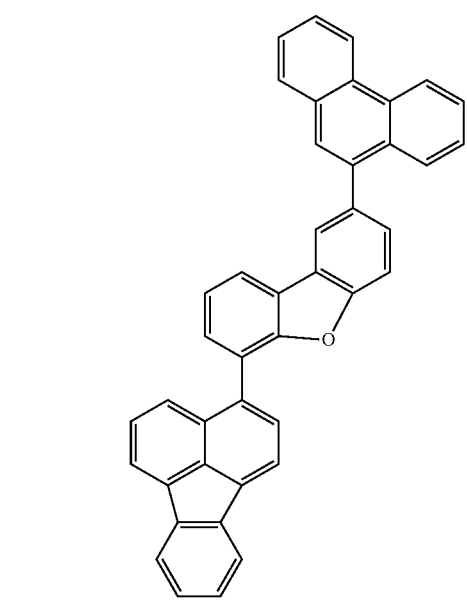
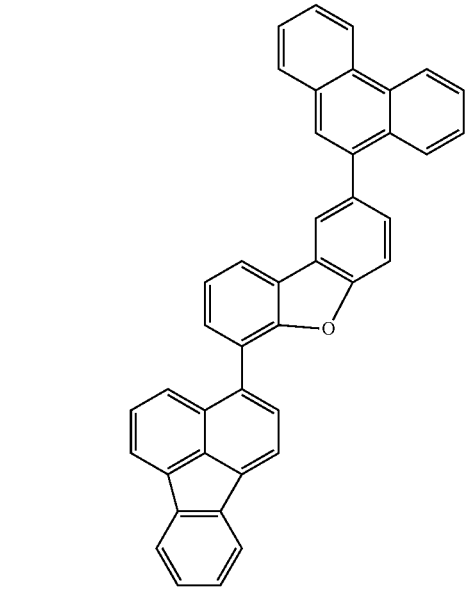
32
-continued
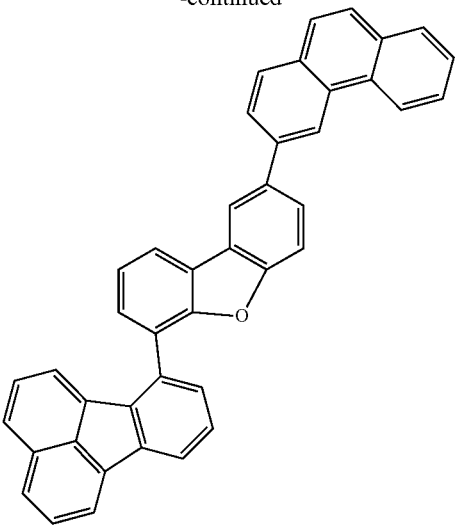
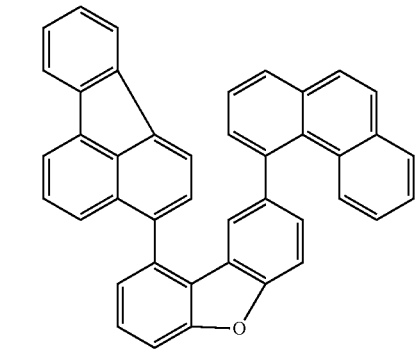
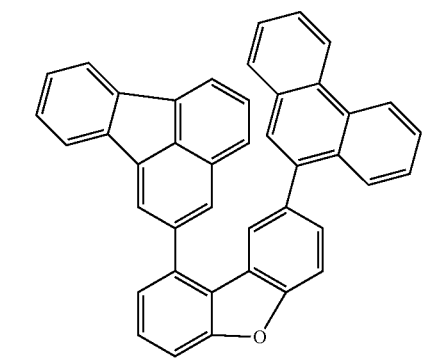
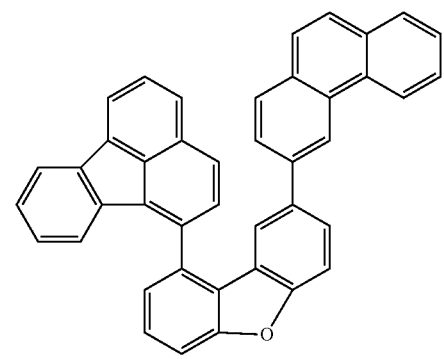

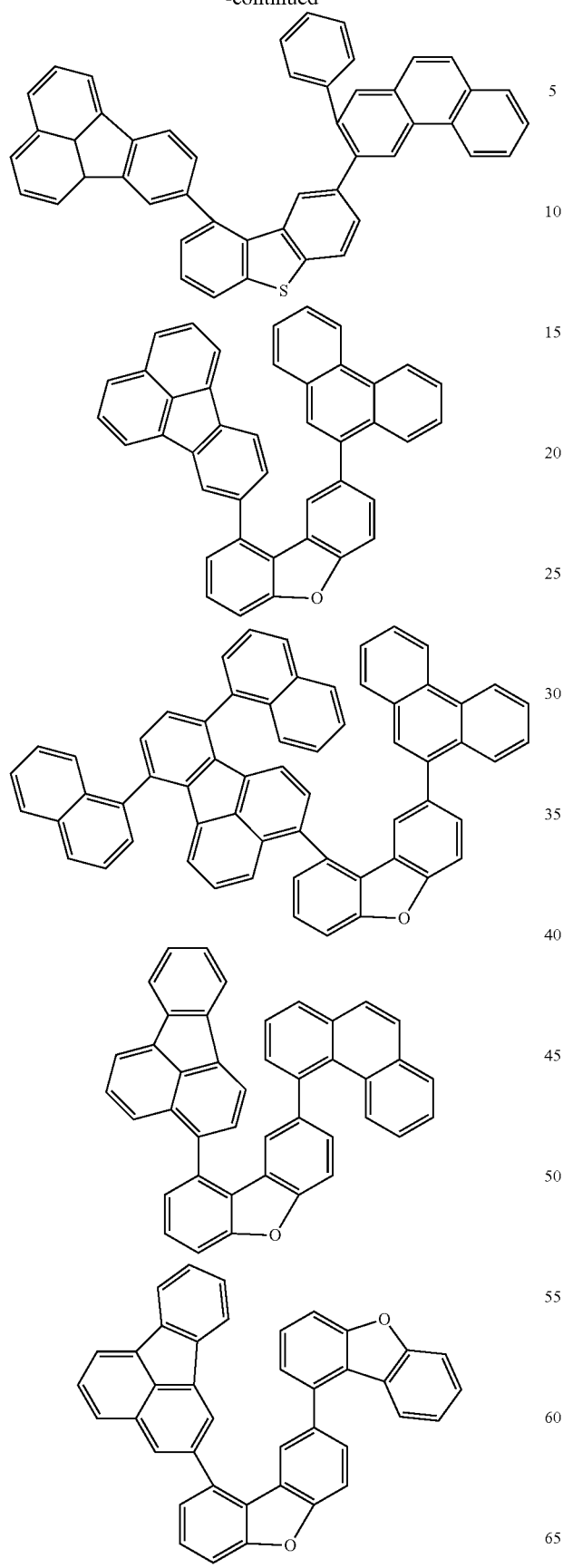
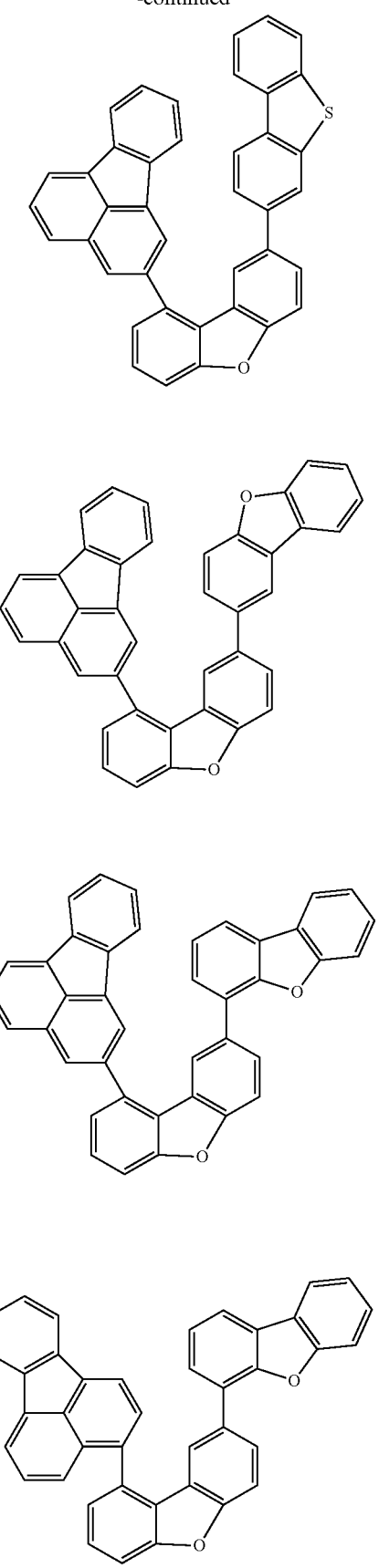

35
-continued
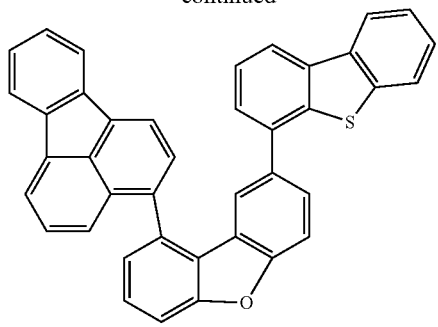
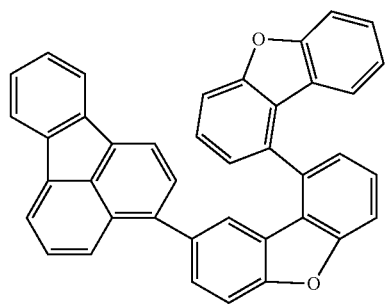
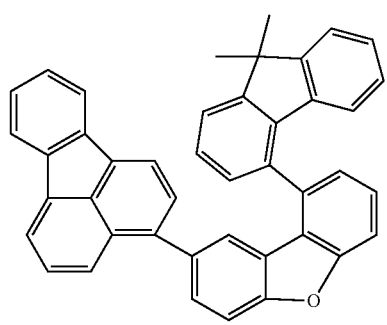
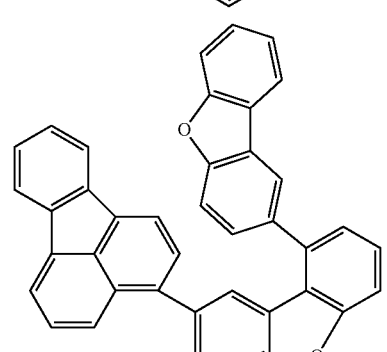
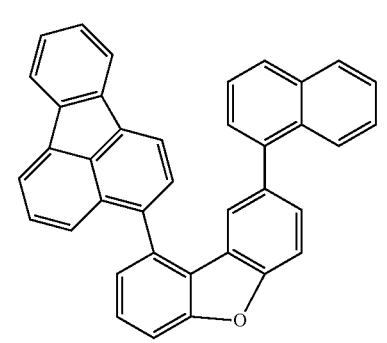
36
-continued
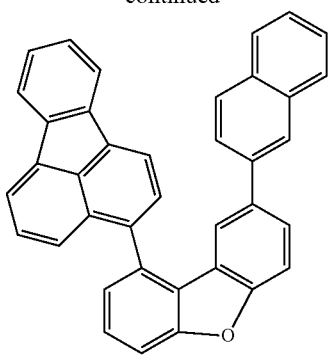
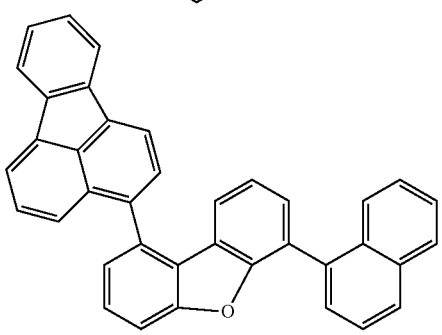
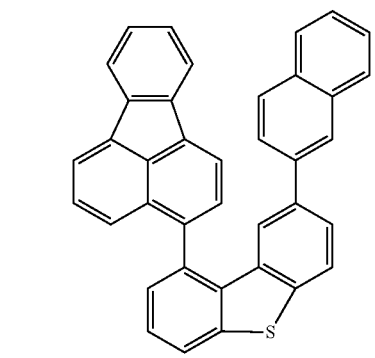
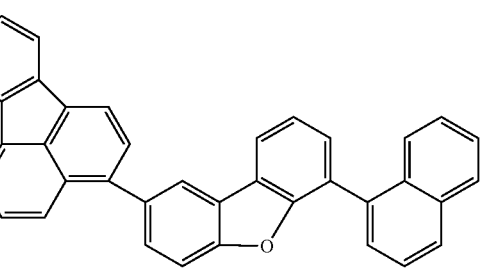
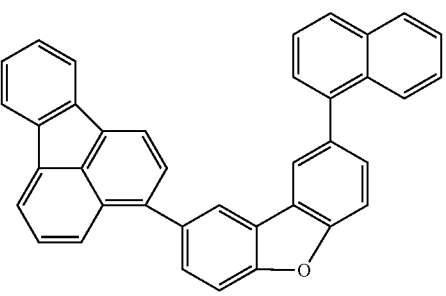

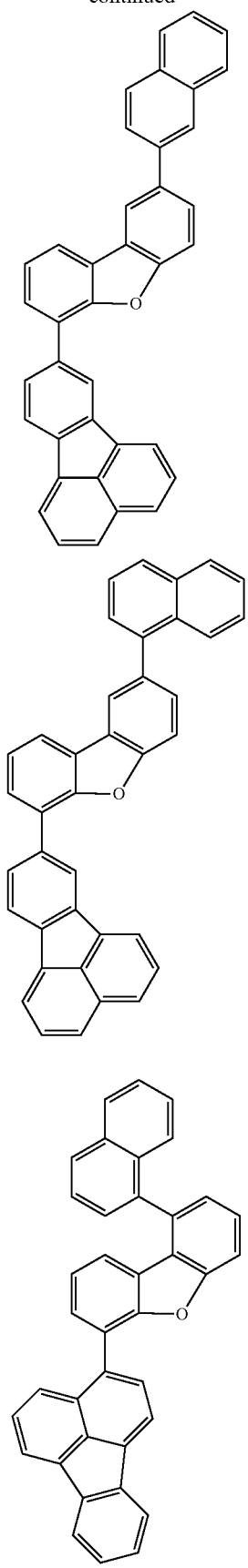
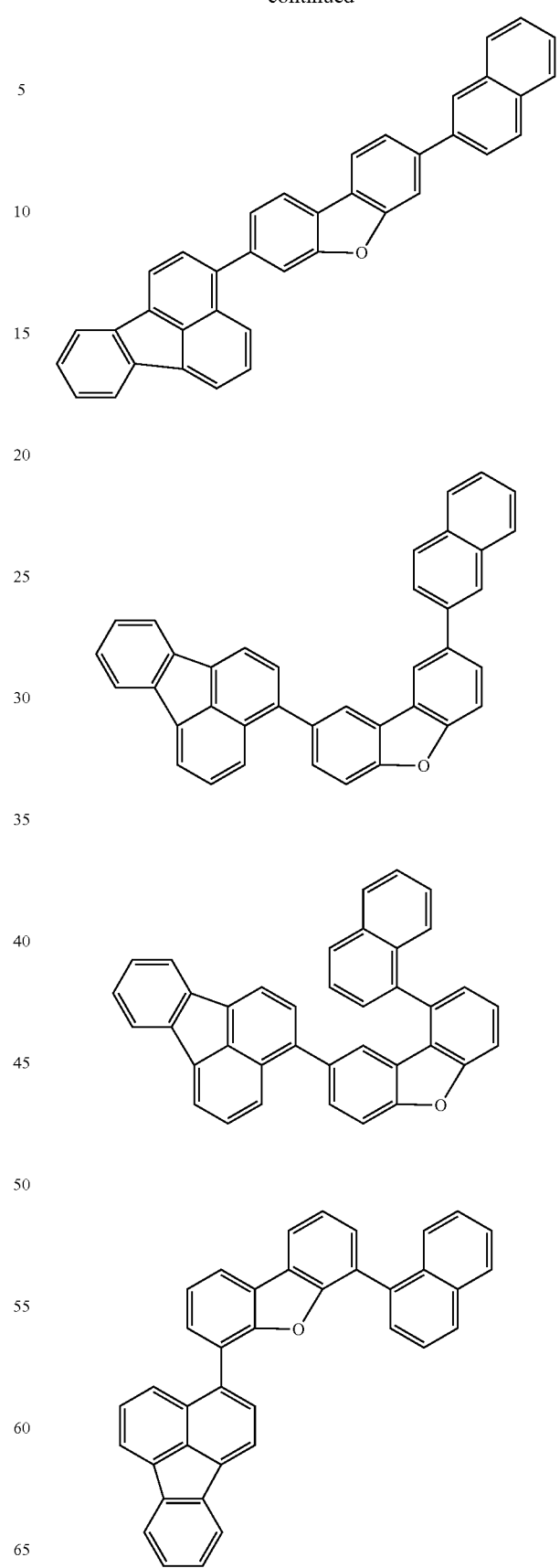

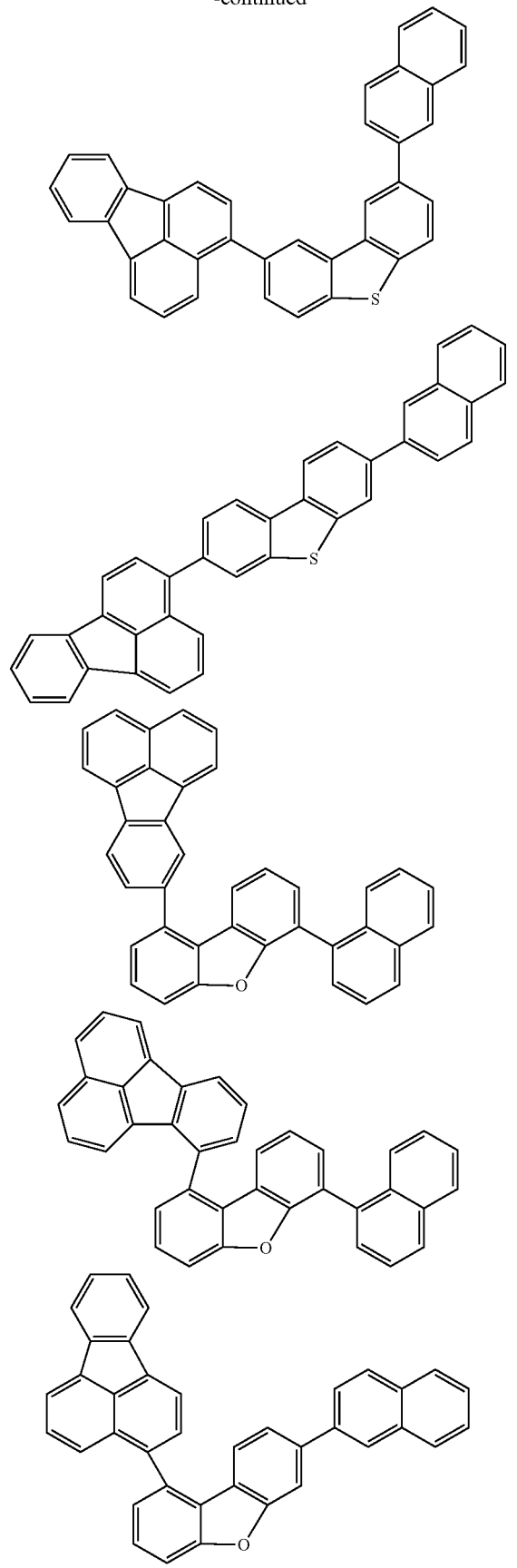
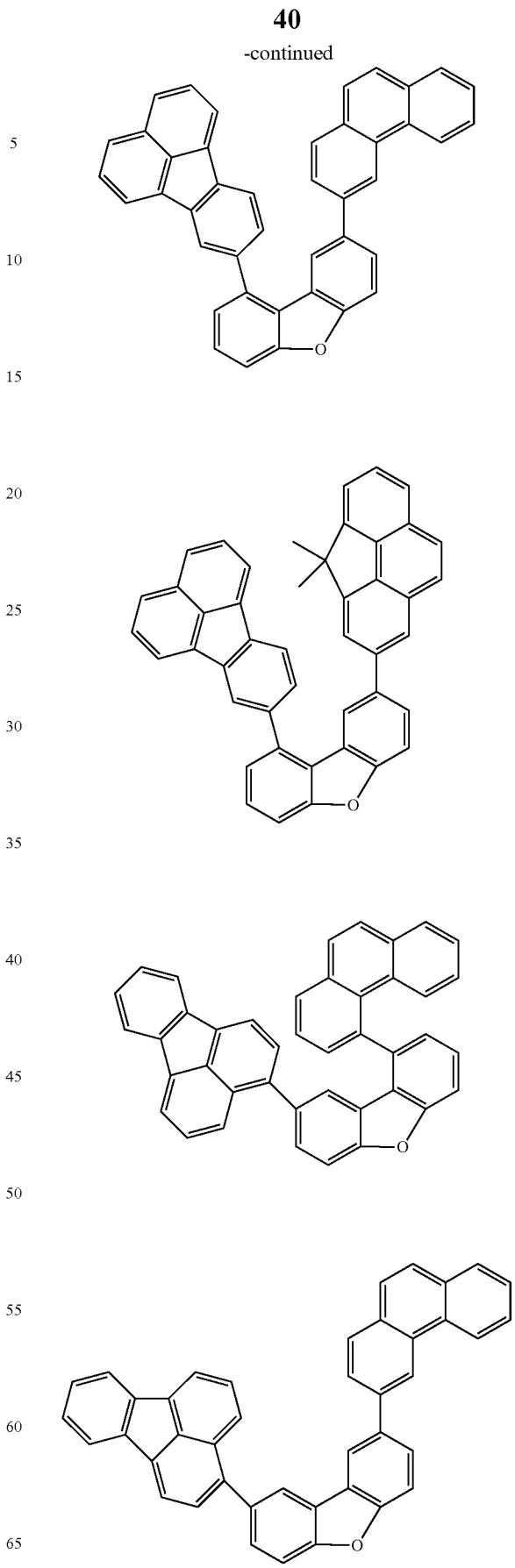

41
-continued
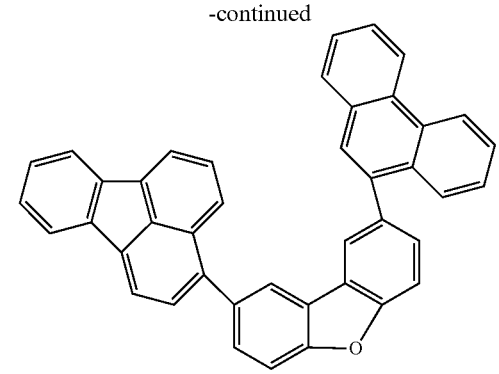
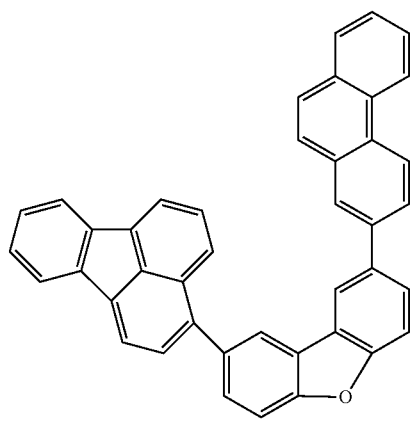
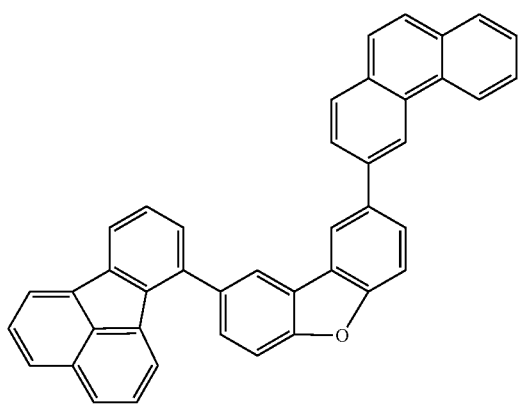
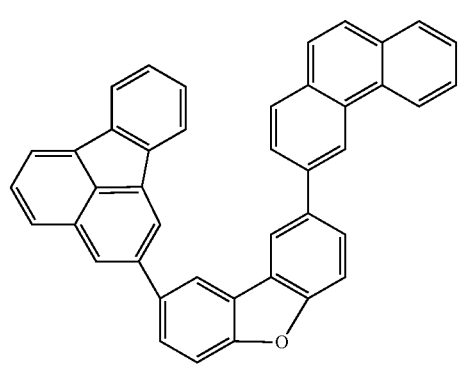
42
-continued
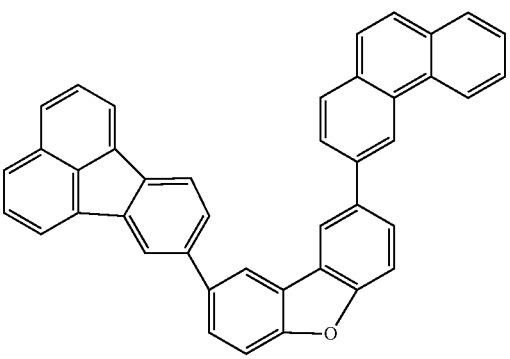
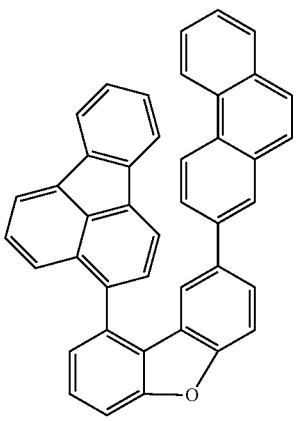
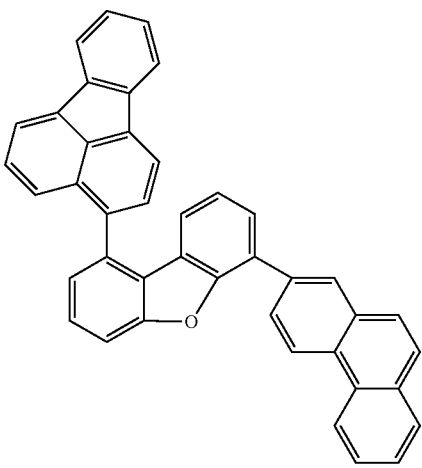
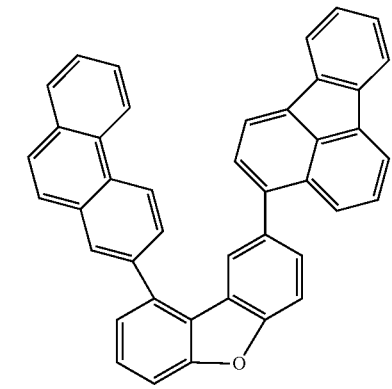

43
-continued
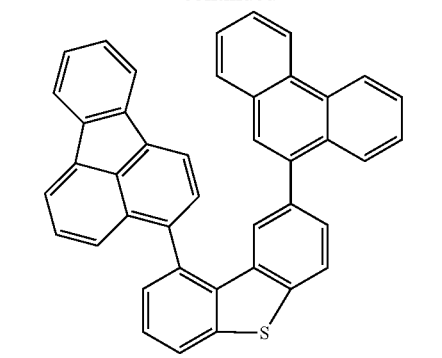
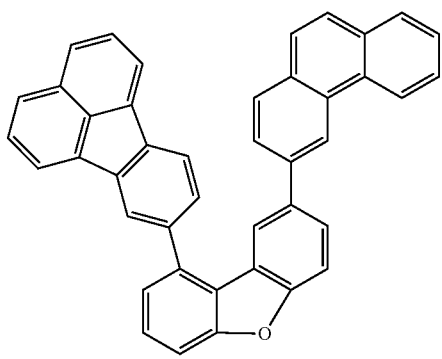
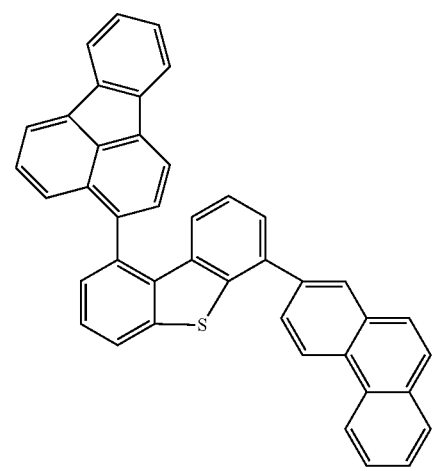
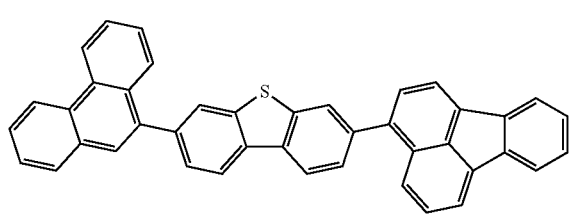
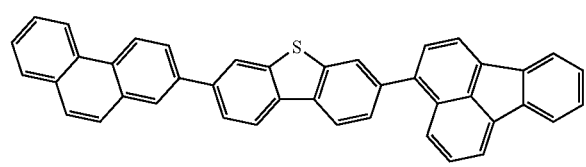
44
-continued
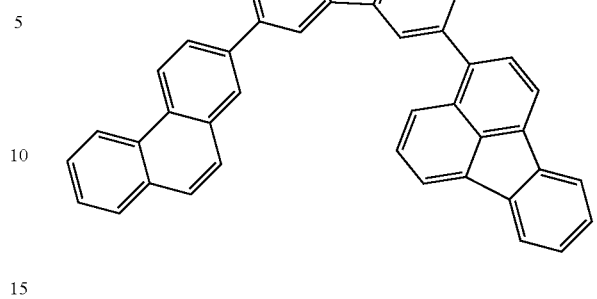
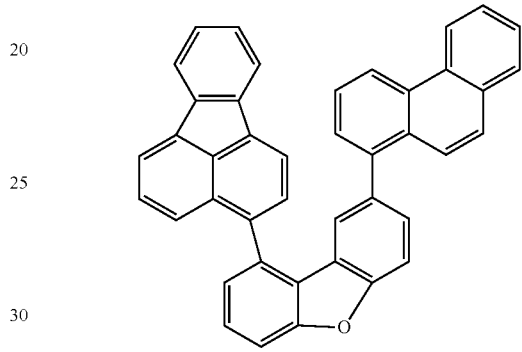
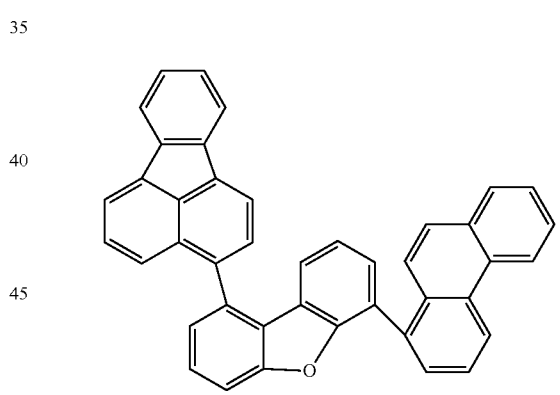
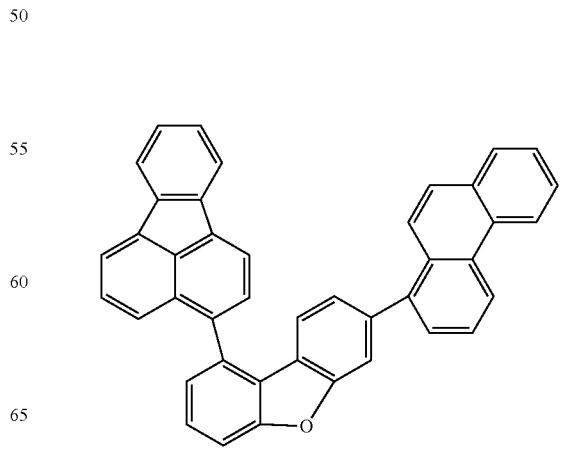

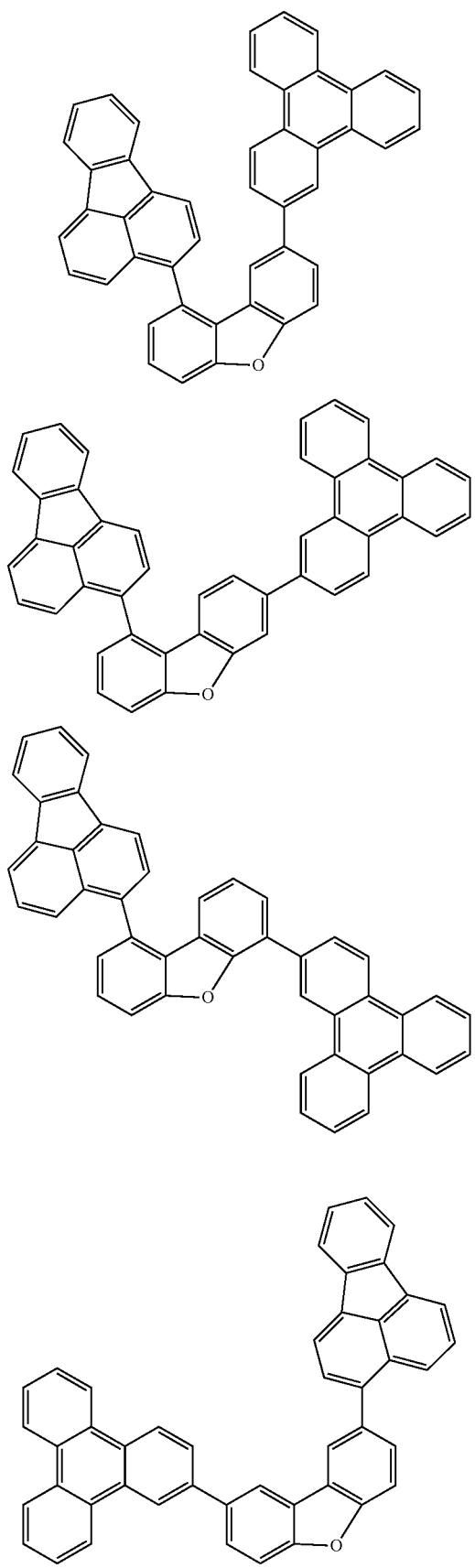
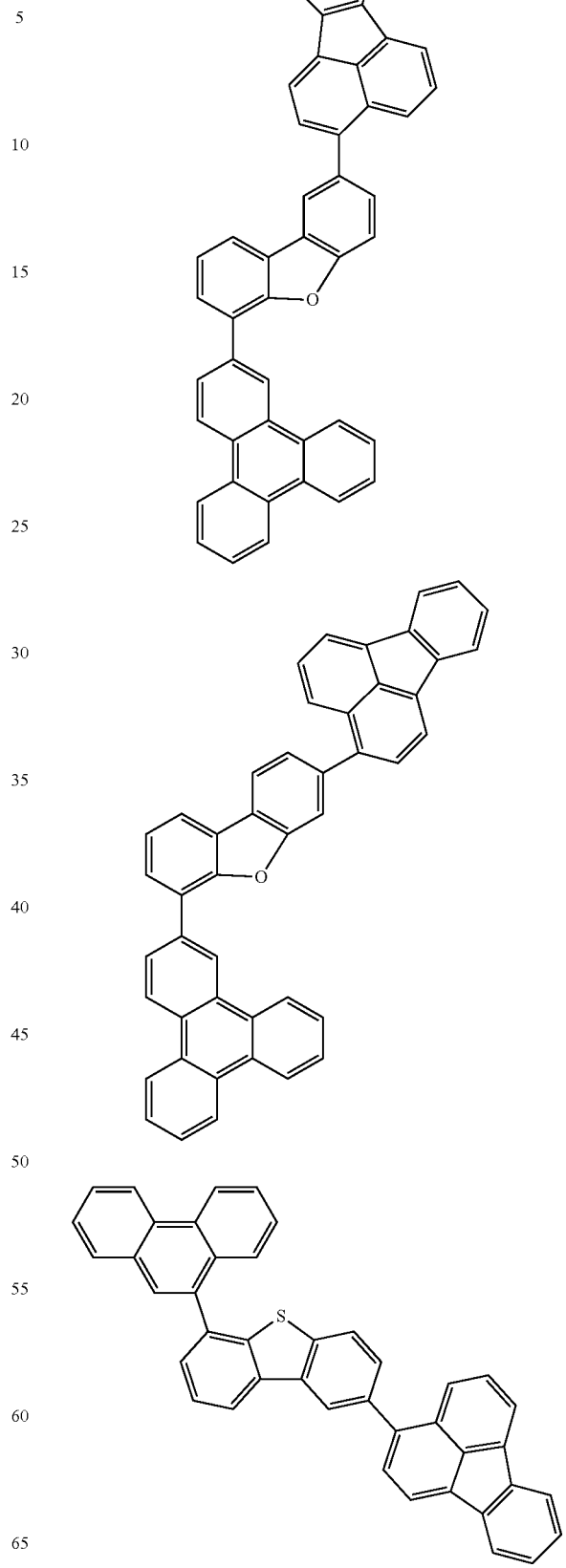

-continued
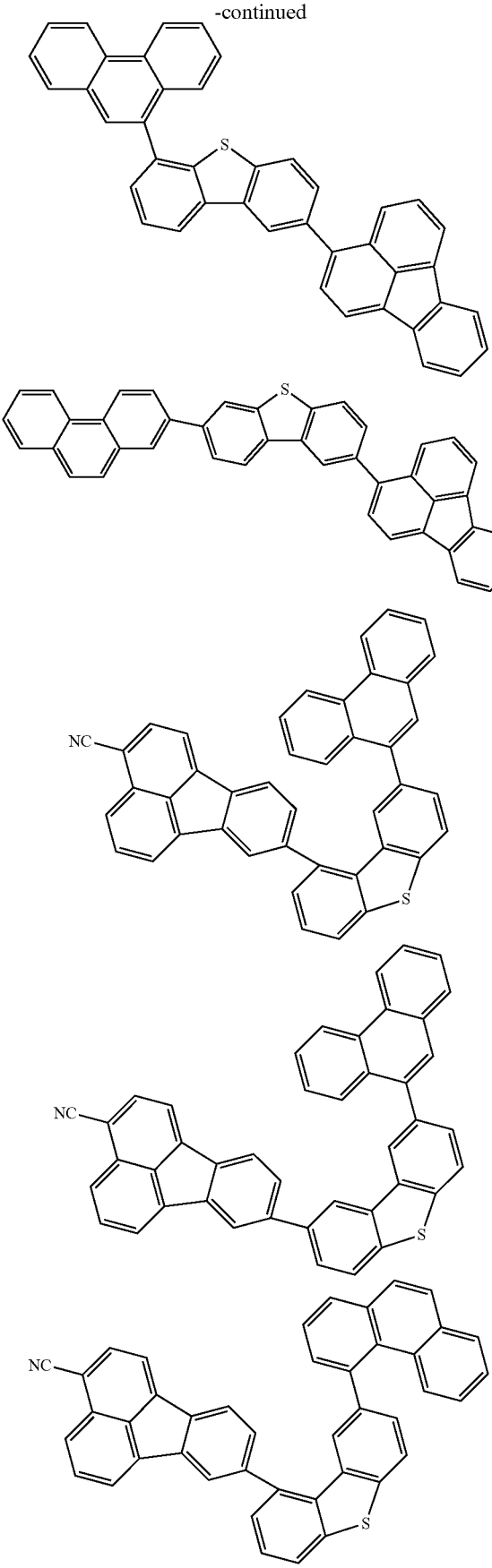
-continued
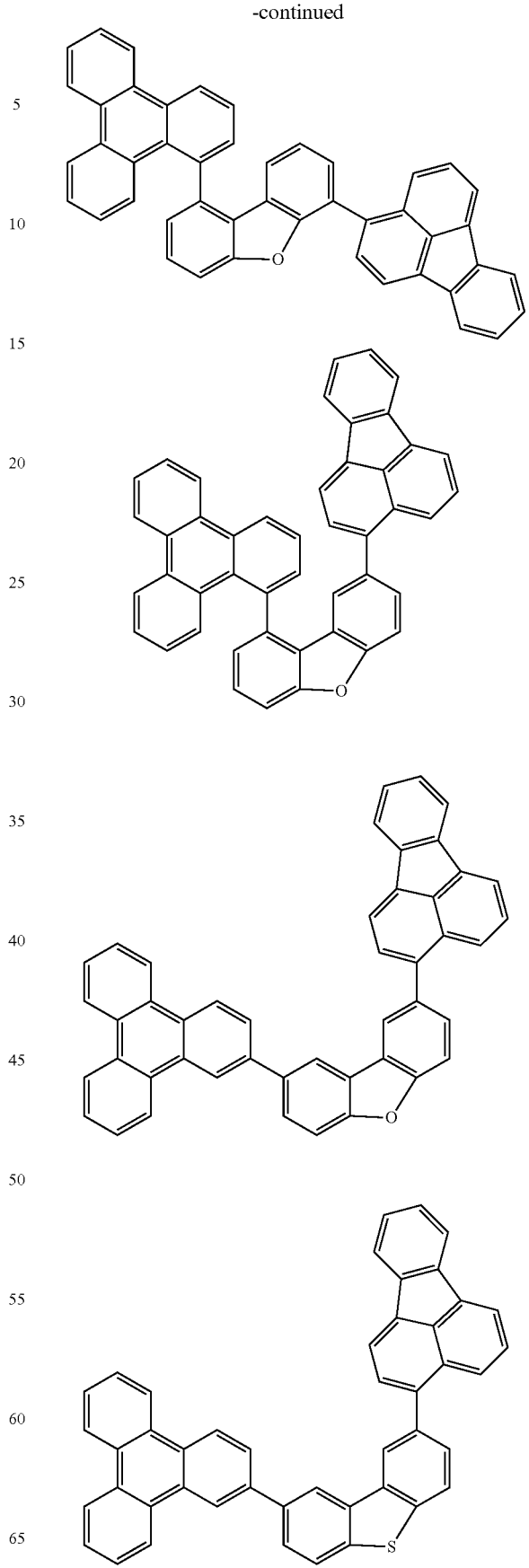

-continued
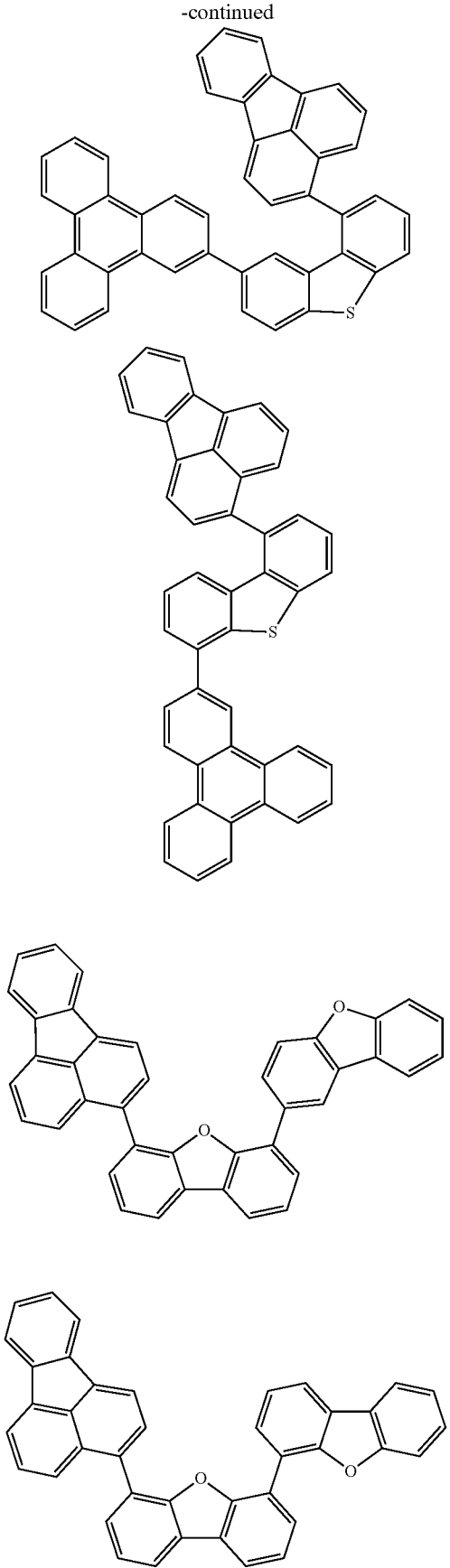
-continued
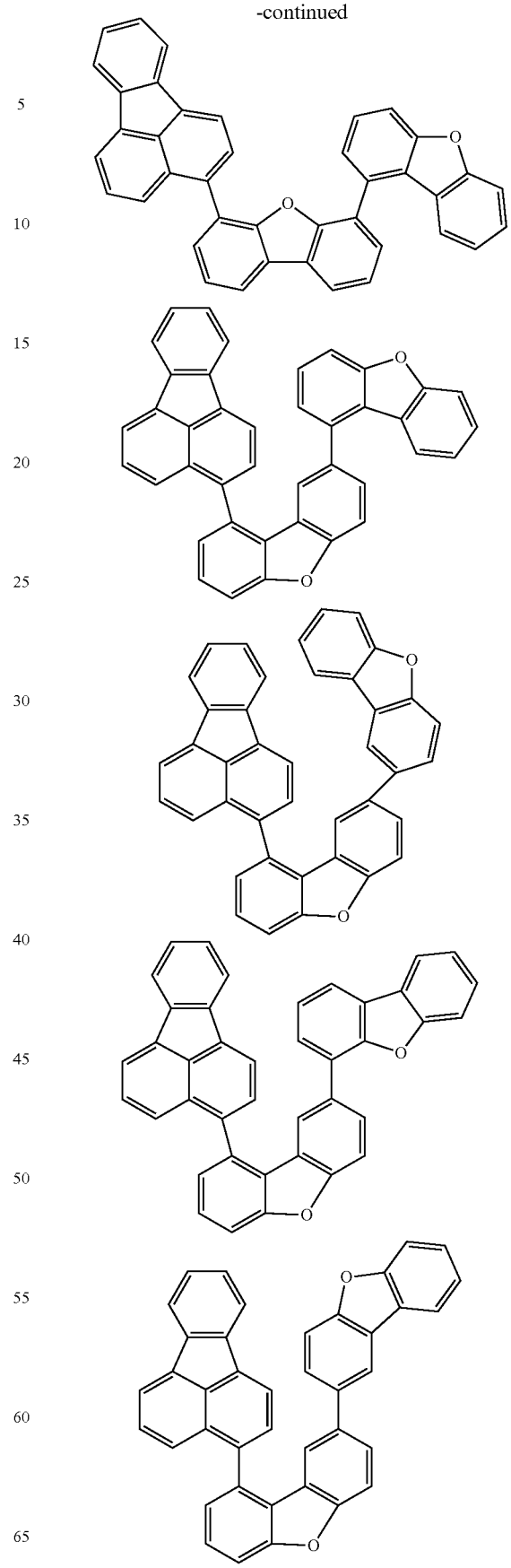

51
-continued
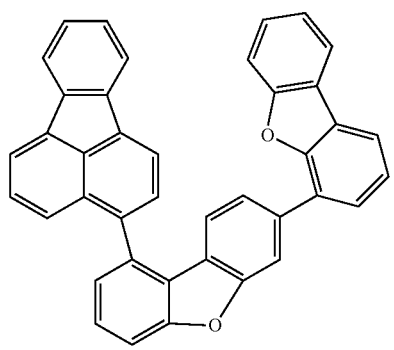
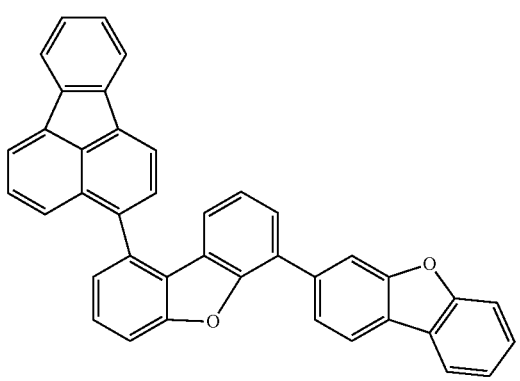
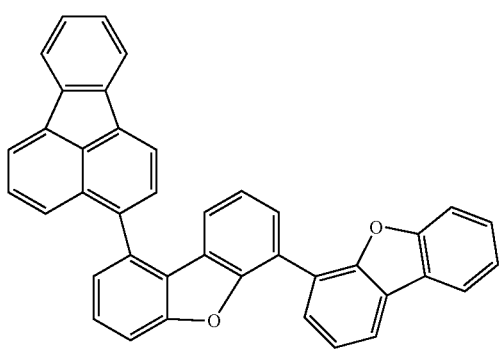
52
-continued
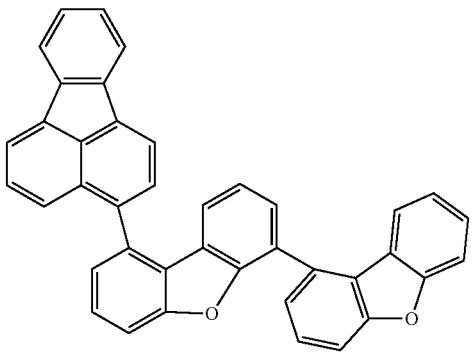
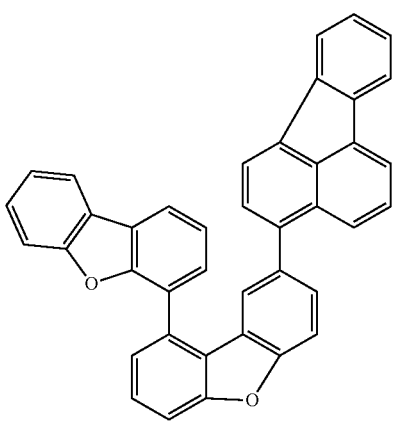
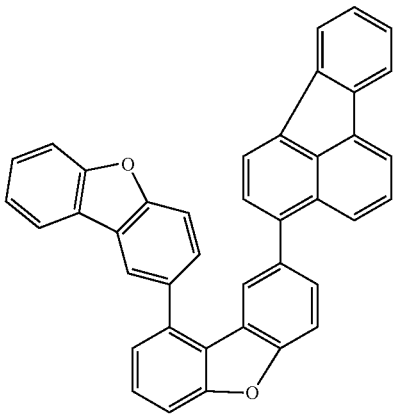
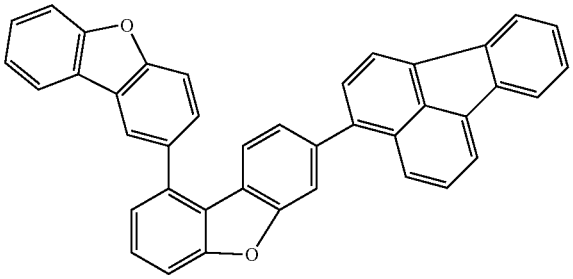

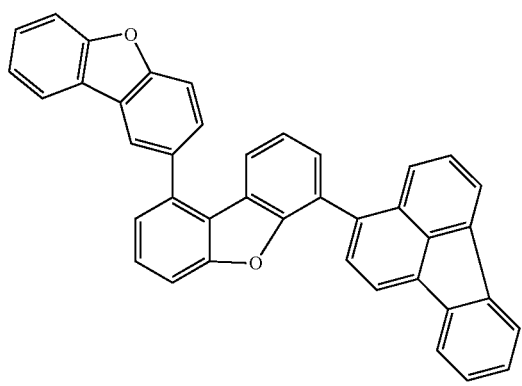
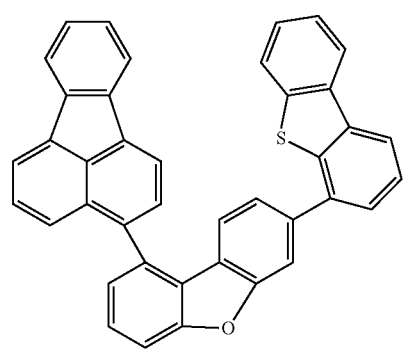
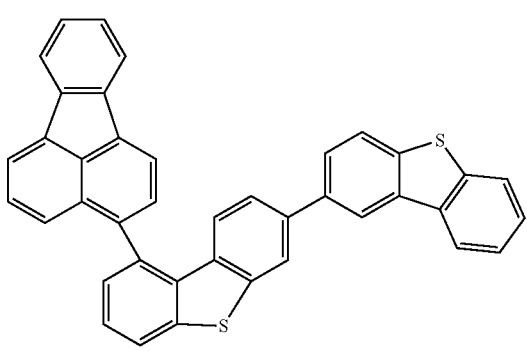
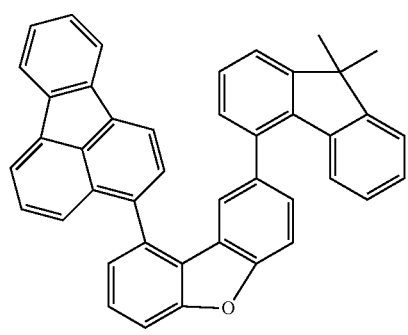
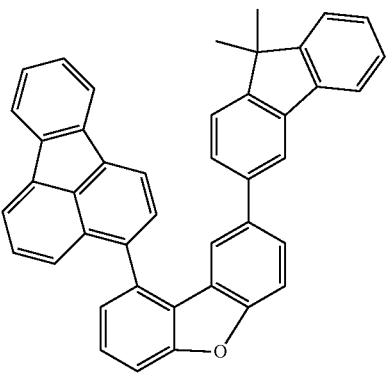
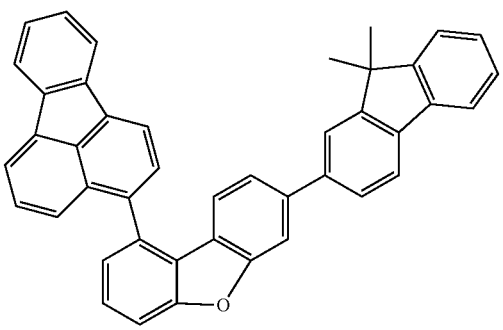
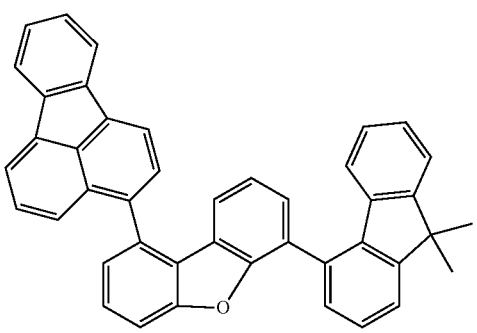
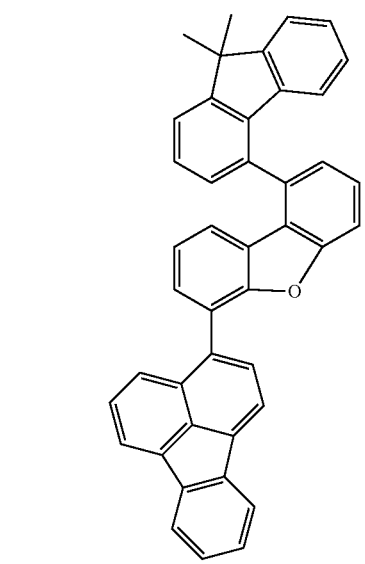

55
-continued
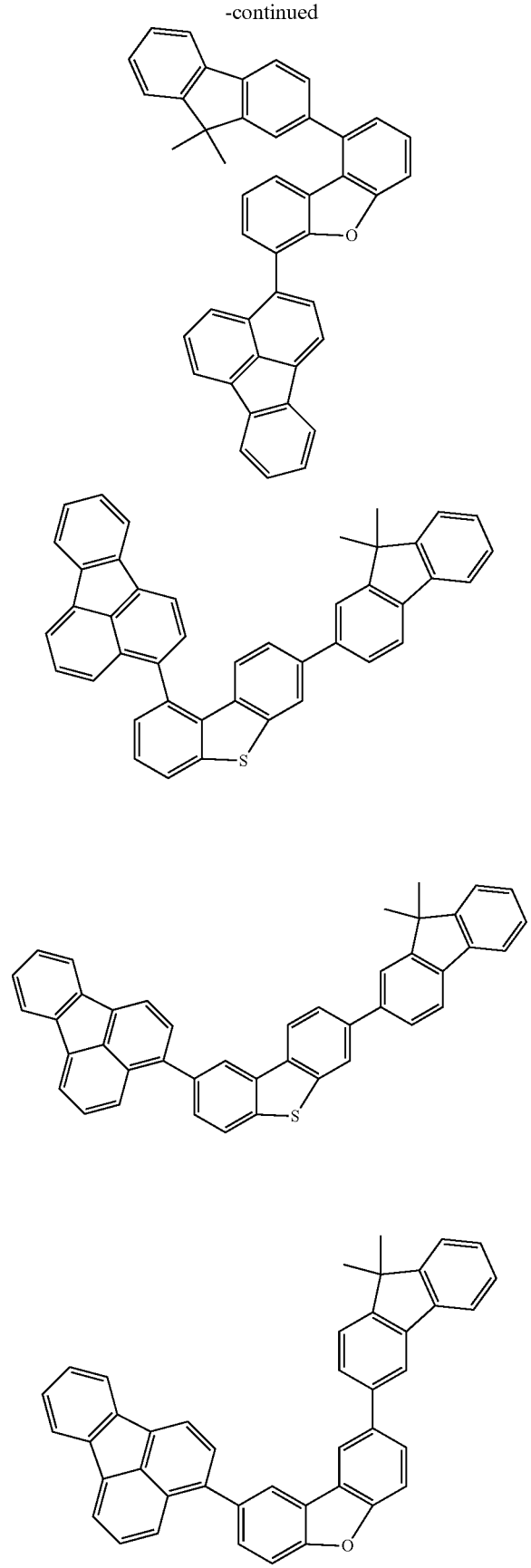
56
-continued
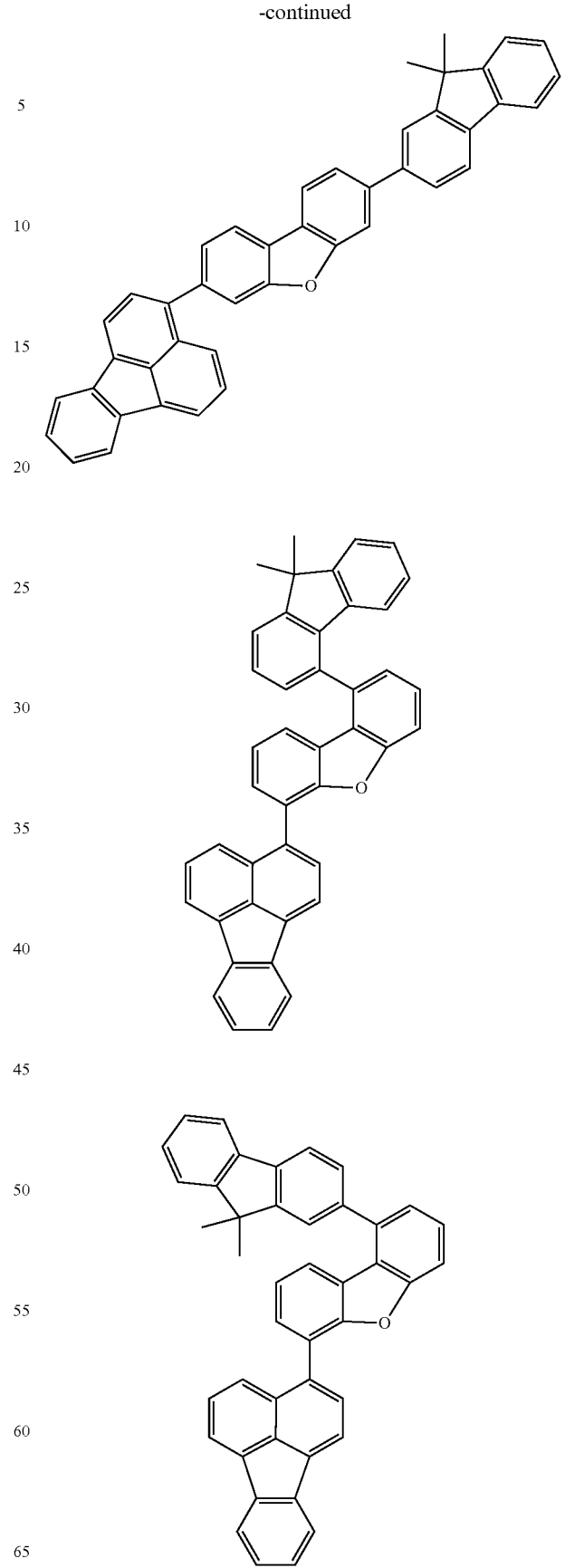

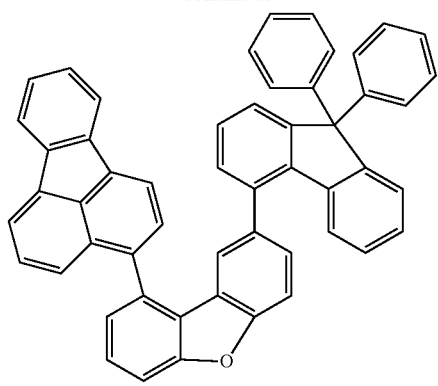
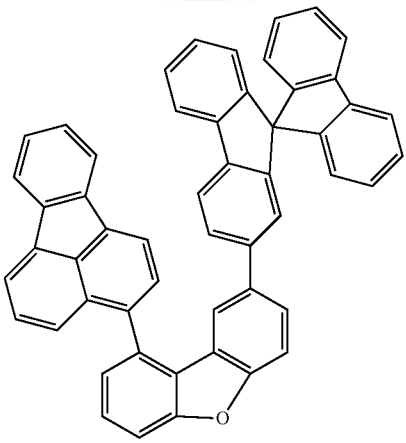
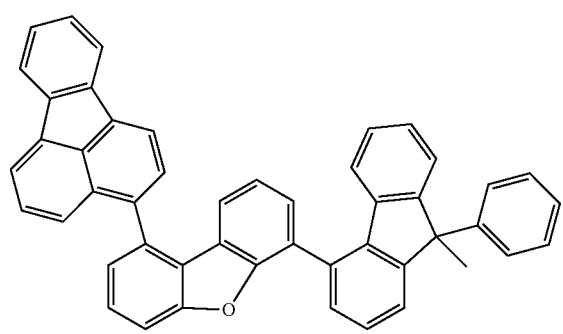
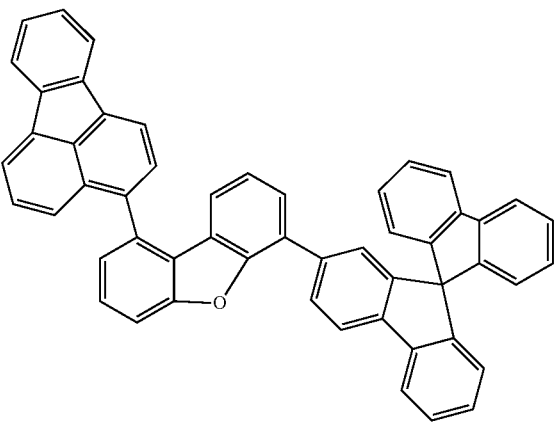
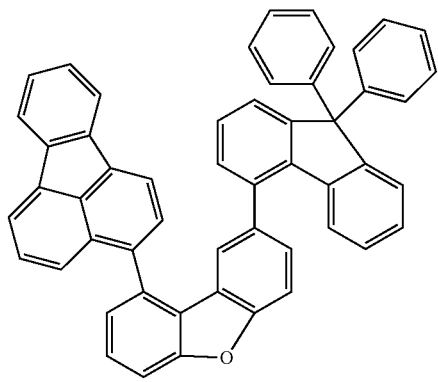
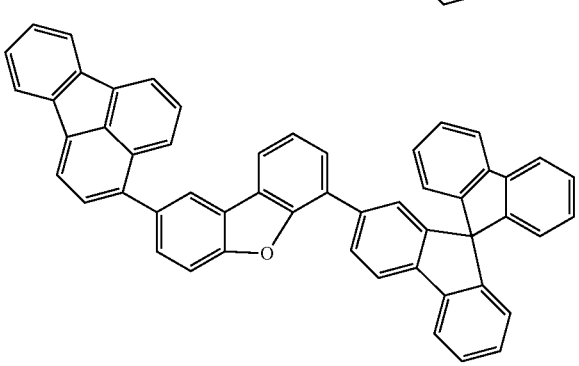
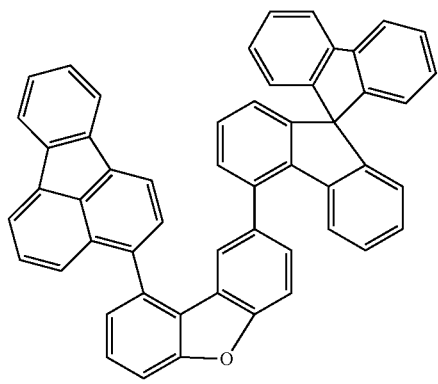
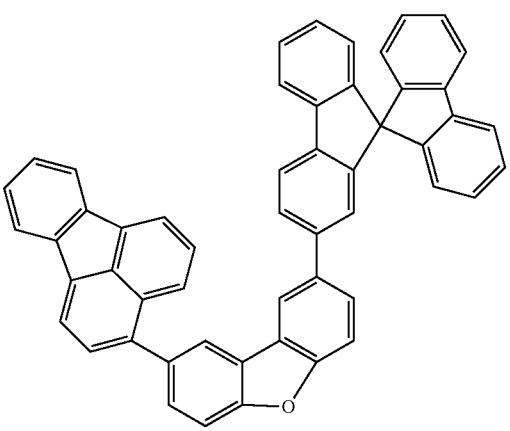

-continued

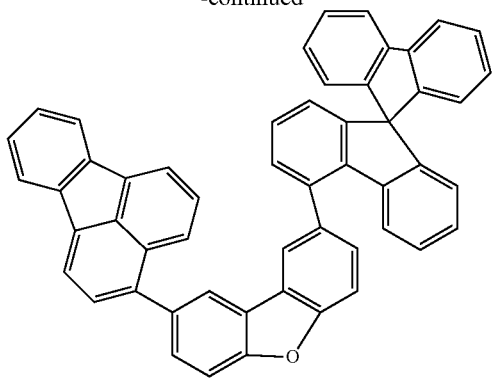

The present invention furthermore relates to a process for the preparation of a compound of the formula (1) or (2), comprising the reaction steps of:

a. Reaction of a dibenzofuran or dibenzothiophene in a C—C coupling, such as Suzuki, Negishi, Yamamoto, Grignard-Cross, Stille coupling, Ullmann coupling with a group Ar as defined above or, when p=1, with a group $Ar^S$;

b. Reaction of the compound obtained in step a in a C—C coupling, such as Suzuki, Negishi, Yamamoto, Grignard-Cross, in order to add the fluoranthene group on the dibenzothiophene or dibenzofuran skeleton.

The materials of the invention can generally be prepared according to the following synthetic schemes 1 or 2.

Scheme 1

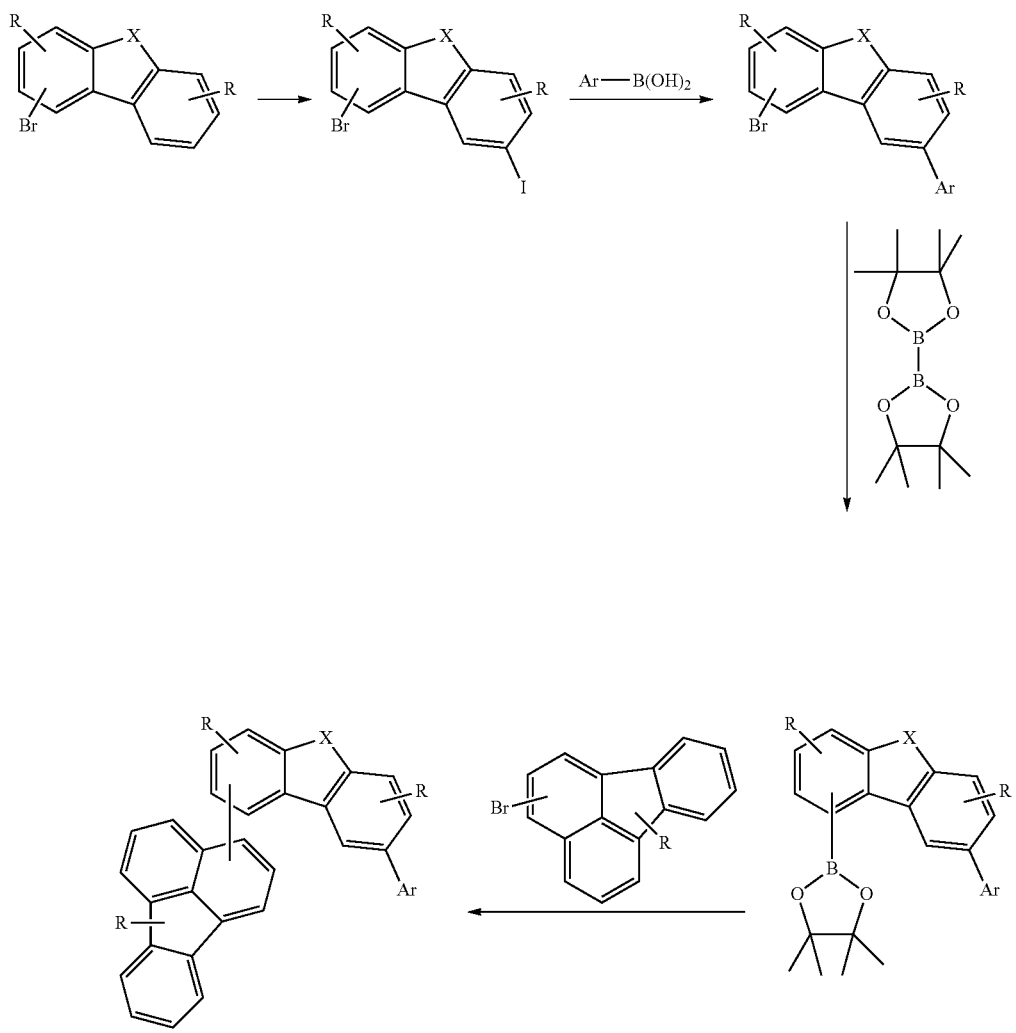

X = S, O

Scheme 2

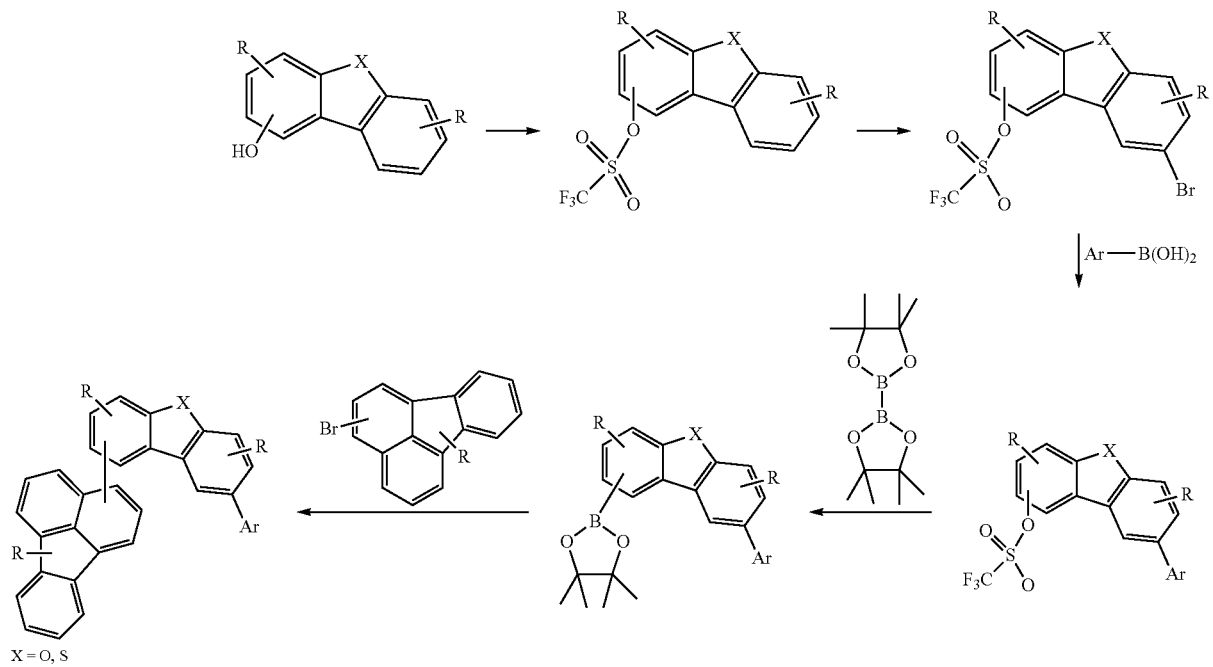

X = O, S

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetraline, veratrole, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, hexamethylindane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycoldimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention therefore furthermore relates to a formulation comprising a compound according to the invention and at least one further compound. The further compound may be, for example, a solvent, in particular one of the above-mentioned solvents or a mixture of these solvents. However, the further compound may also be at least one further organic or inorganic compound which is likewise employed in the electronic device, for example an emitting compound and/or a further matrix material. Suitable emitting compounds and further matrix materials are indicated below in connection with the organic electroluminescent device. This further compound may also be polymeric.

The compounds according to the invention are suitable for use in an electronic device, in particular in an organic electroluminescent device. The present invention therefore furthermore relates to the use of a compound according to the invention in an electronic device, in particular in an organic electroluminescent device. The present invention still furthermore relates to an electronic device comprising at least one compound according to the invention.

An electronic device in the sense of the present invention is a device which comprises at least one layer which comprises at least one organic compound. The component may also comprise inorganic materials or also layers which are built up entirely from inorganic materials. The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), dye-sensitised organic solar cells (DSSCs), organic optical detectors, organic photoreceptors, organic field-quench devices (O-FQDs), light-emitting electrochemical cells (LECs), organic laser diodes (O-lasers) and "organic plasmon emitting devices", but preferably organic electroluminescent devices (OLEDs), particularly preferably phosphorescent OLEDs.

The organic electroluminescent device comprises cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. Interlayers, which have, for example, an exciton-blocking function, may likewise be introduced between two emitting layers. However, it should be pointed out that each of these layers does not necessarily have to be present. The organic electroluminescent device here may comprise one emitting layer, or it may comprise a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having two emitting layers, where the two layers exhibit blue and orange or yellow emission, or three emitting layers, where the three layers exhibit blue, green and orange or red emission (for the basic structure see, for example, WO 2005/011013). The organic electroluminescent device according to the invention may also be a tandem OLED, in particular also for white-emitting OLEDs.

The compound according to the invention in accordance with the embodiments indicated above can be employed in various layers of the electronic device, depending on the precise structure. Preference is given to an organic electroluminescent device comprising a compound of the formula (1) or (2) or the preferred embodiments indicated above as matrix material for phosphorescent or fluorescent emitters, in particular for phosphorescent emitters, and/or in an electron-blocking or exciton-blocking layer and/or in a charge generation layer and/or in a hole-blocking or electron-transport layer, depending on the precise substitution.

In a preferred embodiment of the invention, the compound according to the invention is employed as matrix material for a phosphorescent compound in an emitting layer. The organic electroluminescent device here may comprise one emitting layer, or it may comprise a plurality of emitting layers, where at least one emitting layer comprises at least one compound according to the invention as matrix material.

If the compound according to the invention is employed as matrix material for a phosphorescent compound in an emitting layer, it is preferably employed in combination with one or more phosphorescent materials (triplet emitters). Phosphorescence in the sense of this invention is taken to mean the luminescence from an excited state having relatively high spin multiplicity, i.e. a spin state >1, in particular from an excited triplet state. In the sense of this application, all luminescent complexes containing transition metals or lanthanides, in particular all iridium, platinum and copper complexes, are to be regarded as phosphorescent compounds. In the sense of the application, red and yellow triplet emitters exhibit a lowest triplet state T1, which is comprised between 2.4 and 1.8 eV.

The energy of the lowest triplet state T1 of the phosphorescent emitter is determined via quantum chemical calculations using the software package "Gaussian09, Revision D.01" (Gaussian Inc.). In order to calculate organometallic compounds, firstly a geometry optimization is carried out using the Hartree-Fock method, the standard basis set "LanL2 MB" (Gaussian input line "# HF/LanL2 MB opt") and the charge 0 with a multiplicity 1. Subsequently, a single point energy calculation is carried out on top of the optimized geometry. In this calculation the ground state and the triplet states are determined via the TDDFT method (time dependent density functional theory) with the DFT functional B3PW91 and the standard basis set 6-31G(d) (charge 0, multiplicity 1). The Gaussian input line is "# B3PW91/ gen pseudo=lanl2 td=(50-50, nstates=4)". In contrast to all other atoms, the ECP basis set (effective core potential) "LanL2DZ" is used for the metal atom.

The energetically lowest singlet state is the S0. The triplet state T1 is defined as the relative excitation energy (in eV) in the triplet state with lowest energy which arises from the quantum chemical single point calculation described above.

The method described herein is independent of the software package used and always gives the same results. Examples of frequently used programs for this purpose are "Gaussian09 W" (Gaussian Inc.) and Q-Chem 4.1 (Q-Chem, Inc.).

The mixture of the compound according to the invention and the emitting compound comprises between 99 and 1% by vol., preferably between 98 and 10% by vol., particularly preferably between 97 and 60% by vol., in particular between 95 and 80% by vol., of the compound according to the invention, based on the entire mixture comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture comprising emitter and matrix material.

A further preferred embodiment of the present invention is the use of the compound according to the invention as matrix material for a phosphorescent emitter in combination with a further matrix material. Particularly suitable matrix materials which can be employed in combination with the compounds according to the invention are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-bis-carbazolylbiphenyl) or the carbazole derivatives disclosed in WO 2005/039246, US 2005/0069729, JP 2004/288381, EP 1205527, WO 2008/086851 or WO 2013/041176, indolocarbazole derivatives, for example in accordance with WO 2007/063754 or WO 2008/056746, indenocarbazole derivatives, for example in accordance with WO 2010/136109, WO 2011/000455, WO 2013/041176 or WO 2013/056776, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2007/063754, WO 2008/056746, WO 2010/015306, WO 2011/057706, WO 2011/060859 or WO 2011/060877, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with WO 2011/042107, WO 2011/060867, WO 2011/088877 and WO 2012/143080, or triphenylene derivatives, for example in accordance with WO 2012/048781. A further phosphorescent emitter which emits at shorter wavelength than the actual emitter may likewise be present in the mixture as co-host, or a compound which does not participate in the charge transport to a significant extent, if at all, as described, for example, in WO 2010/108579. It is well within the art to select appropriate matrix materials and emitters for light-emitting layers along with determining the appropriate relative proportions of all the materials present.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescence emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 2001/41512, WO 2002/02714, WO 2002/15645, EP 1191613, EP 1191612, EP 1191614, WO 2005/033244, WO 2005/019373, US 2005/0258742, WO 2010/086089, WO 2011/157339, WO 2012/007086, WO 2012/163471, WO 2013/000531 and WO 2013/020631. Also suitable are, for example, the metal complexes disclosed in the applications EP 2872590 and EP 2882763. In general, all phosphorescent complexes as are used in accordance with the prior art for phosphorescent OLEDs and as are known to the person skilled in the art in the area of organic electroluminescence are suitable, and the person skilled in the art will be able to use further phosphorescent complexes without inventive step.

The compounds according to the invention are also suitable, in particular, as matrix materials for phosphorescent emitters in organic electroluminescent devices, as described, for example, in US 2011/0248247 and US 2012/0223633. In these multicoloured display components, an additional blue emission layer is applied by vapour deposition over the entire area to all pixels, also those having a colour other than blue. It has been found here, surprisingly, that the compounds according to the invention, when employed as matrix materials for the red and/or green pixels, more particularly for the red pixels, continue to result in very good emission together with the vapour-deposited blue emission layer.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is the same as or similar to the metal complex in the emitting layer as hole-transport or hole-injection material directly adjacent to the emitting layer, as described, for example, in WO 2009/030981.

In a further embodiment of the invention, the compound according to the invention is employed in an exciton-blocking layer.

In still a further preferred embodiment of the invention, the compound according to the invention is employed as electron-transport material in an electron-transport or electron-injection layer. The emitting layer here may be fluorescent or phosphorescent. If the compound is employed as electron-transport material, it may be preferred for it to be doped, for example with alkali metals or alkali-metal complexes, such as, for example, Li or LiQ (lithium hydroxyquinolinate).

In still a further preferred embodiment of the invention, the compound according to the invention is employed in a hole-blocking layer. A hole-blocking layer is taken to mean a layer which is directly adjacent to an emitting layer on the cathode side. Another preferred embodiment is employing the compound as part of a charge generation layer. A charge generation layer (CGL) works as an injector of an electron-hole pair upon voltage application and is well-known in the art. Generally, a CGL consists of a electron-rich layer (for example, a n-doped electron transporting layer) adjacent to an electron-poor layer (for example, a p-doped hole transporting layer). However, in some cases, the CGL can be only a single layer. In other cases, one or both layers of the CGL may or may not be doped.

In the further layers of the organic electroluminescent device according to the invention, all materials can be used as are usually employed in accordance with the prior art. The person skilled in the art will therefore be able to employ all materials which are known for organic electroluminescent devices in combination with the compounds of the formula (1) or (2) according to the invention or the preferred embodiments indicated above without inventive step.

Preference is furthermore given to an organic electroluminescent device, characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), inkjet printing or nozzle printing. Soluble compounds, which are obtained, for example, by suitable substitution, are necessary for this purpose.

Also possible are hybrid processes, in which, for example, one or more layers are applied from solution and one or more further layers are applied by vapour deposition. These processes are generally known to the person skilled in the art and can be applied by him without inventive step to organic electroluminescent devices comprising the compounds according to the invention.

The compounds according to the invention and the organic electroluminescent devices according to the invention are distinguished by one or more of the following surprising advantages over the prior art:

1. The compounds according to the invention, employed as matrix material for fluorescent or phosphorescent emitters, result in long lifetimes. This applies, in particular, if the compounds are employed as matrix material for a phosphorescent emitter.

2. The compounds according to the invention result in very high efficiency. This applies, in particular, if the compounds are employed as matrix material for a phosphorescent emitter or as a hole-blocking material.

3. In some embodiments, the compounds according to the invention result in low voltage devices. This applies, in particular, if the compounds are employed as matrix material for a phosphorescent emitter or in an electron-transport layer.

These above-mentioned advantages are not accompanied by an impairment in the other electronic properties.

The invention is explained in greater detail by the following examples without wishing to restrict it thereby. The person skilled in the art will be able to use the descriptions to carry out the invention throughout the range disclosed and prepare further compounds according to the invention without inventive step and use them in electronic devices or apply the process according to the invention.

EXAMPLES

A) Synthesis Examples

The following syntheses are carried out, unless indicated otherwise, under a protective-gas atmosphere in dried solvents. The solvents and reagents can be purchased from ALDRICH or ABCR. The numbers indicated in the case of the starting materials which are commercially available are the corresponding CAS numbers.

The materials of the invention can generally be prepared according to the schemes 1 or 2 as defined above.

a) 6-Bromo-2-fluoro-2'-methoxy-biphenyl 200 g (664 mmol) of 1-bromo-3-fluoro-2-iodo-benzene, 101 g (664 mmol) of 2-methoxyphenyl-boronic acid and 137.5 g (997 mmol) of sodium tetraborate are dissolved in 1000 mL of THF and 600 ml of water and degassed. Afterwards, 9.3 g (13.3 mmol) of bis (triphenylphosphine) palladium (II) chloride and 1 g (20 mmol) of hydrazinium hydroxide are added to the reaction mixture, which is then stirred at 70° C. for 48 h under inert gas atmosphere. The cooled solution is completed with toluene, washed several times with water, dried and concentrated. The product is washed via column chromatography on silica gel with toluene/heptane:ethyl (1:2).

Yield: 155 g (553 mmol), 83% of theory.

The following compounds are prepared analogously:

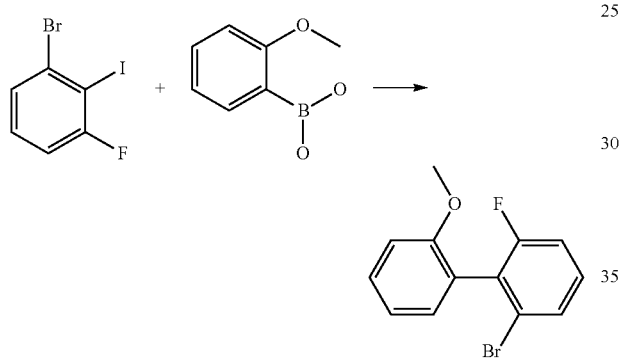

b) 6'-bromo-2'-fluoro-biphenyl-2-ol

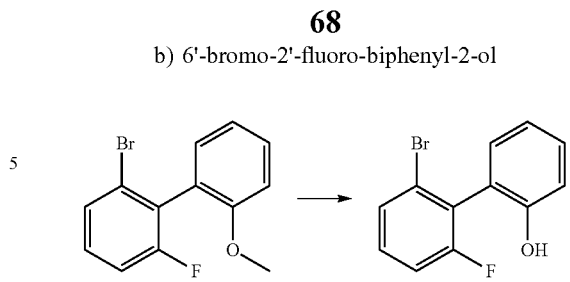

112 g (418 mmol) of 6-bromo-2-chloro-2'-methoxy-biphenyl are dissolved in 2 L of dichloromethane and cooled to 5° C. Afterwards, 41.01 ml (431 mmol) of boron tribromide are added dropwise within 90 min and the mixture is stirred overnight. The mixture is then slowly mixed with water, the organic phase is washed three times with water and dried over $Na_2SO_4$, evaporated and purified by chromatography.

Yield: 104 g (397 mmol), 98% of theory.

The following compounds are prepared analogously:

| | Reactant 1 | Product | Yield |
|---|---|---|---|
| b1 | | | 92% | c) 1-Bromo-dibenzofuran 111 g (416 mmol) 6'-bromo-2'-fluoro-biphenyl-2-ol are dissolved in 2 L DMF (max 0.003% $H_2O$) SeccoSolv® and cooled to 5° C. 20 g (449 mmol) of sodium hydride (60% suspension in paraffin oil) are added to this solution portion by portion. The mixture is stirred 20 min and then heated to 100° C. during 45 min. The mixture is slowly mixed after cooling with 500 ml of ethanol, and then evaporated and purified by chromatography.

Yield: 90 g (367 mmol), 88.5% of theory.

The following compounds are prepared analogously:

| Reactant 1 | Product | Yield |
|---|---|---|
| c1 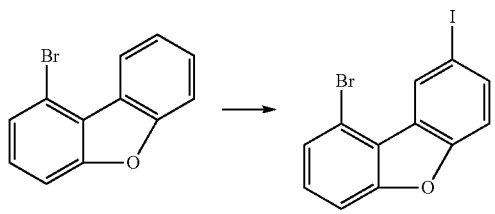 [SMILES: Brc1cccc2oc3ccccc3c12 ; Brc1cccc2oc3ccc(I)cc3c12] | | 81% | d) 1-Bromo-8-iodo-dibenzofuran 20 g (80 mmol) of dibenzofuran-1-boronic acid, 2.06 g (40.1 mmol) of iodine, 3.13 g (17.8 mmol) of iodic acid, 80 ml of acetic acid, 5 ml of sulfuric acid, 5 ml of water and 2 ml of chloroform are stirred at 65° during 3 hours. After cooling, the mixture is mixed with water, the precipitated solid is removed, and the residue is washed three times with water. The residue is recrystallized from toluene and dichloromethane/heptane.

The yield is 25.6 g (68 mmol), corresponding to 85% of theory.

The following compounds are prepared analogously:

| Reactant 1 | Product | Yield |
|---|---|---|
| d1 [65642-94-6] | | 81% | e) Dibenzofuran-1-boronic Acid

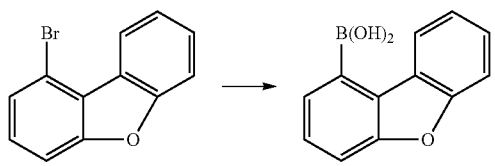 [SMILES: Brc1cccc2oc3ccccc3c12 ; OB(O)c1cccc2oc3ccccc3c12]

180 g (728 mmol) of 1-bromo-dibenzofuran are dissolved in 1500 mL of dried THF and cooled to −78° C. At this temperature, 305 mL (764 mmol/2.5 M in hexane) of n-butyl lithium is added within about 5 min to the mixture, which is then stirred during 2.5 hours at −78° C. At this temperature, 151 g (1456 mmol) of trimethyl borate is added as quickly as possible to the mixture and the reaction mixture is allowed to slowly warm to room temperature (about 18 h). The reaction solution is washed with water and the precipitated solid and the organic phase are dried with toluene. The crude product is extracted out of toluene/methylene chloride at about 40° C.

Yield: 146 g (690 mmol), 95% of theory.

The following compounds are prepared analogously:

| Reactant 1 | Product | Yield |
|---|---|---|
| e1 | | 81% |
| e2 [65642-94-6] | | 73% | f) Trifluoro-methanesulfonic acid-dibenzofuran-1-yl ester

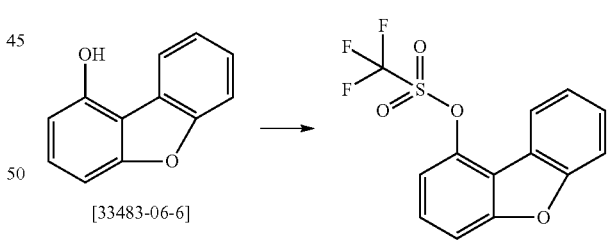

[33483-06-6]

40 g (217 mmol) of dibenzofuran-1-ol is suspended in 500 mL of dichloromethane under a protective gas. 66.9 g (661 mmol) of triethylamine are then dropwise added to this suspension. Afterwards, a solution of 74.5 g of anhydride trifluoromethansulfonic acid in 100 ml of dichloromethane is added dropwise. After 2.5 hours of stirring at 15° C., the solution is mixed with 100 ml of water, the organic phase is then separated and filtered through silica gel with toluene and then concentrated to dryness.

The yield is 60 g (191 mmol), corresponding to 88% of theory.

| | Reactant 1 | Product | Yield |
|---|---|---|---|
| f1 | dibenzothiophen-1-ol [69747-83-7] | dibenzothiophen-1-yl trifluoromethanesulfonate | 83% |
| f2 | 6-bromodibenzothiophen-1-ol [1332939-31-7] | 6-bromodibenzothiophen-1-yl trifluoromethanesulfonate | 87% |
| f3 | 7-bromodibenzofuran-3-ol [74423-78-2] | 7-bromodibenzofuran-3-yl trifluoromethanesulfonate | 85% |
| f4 | 6-bromodibenzothiophen-3-ol [1332939-34-0] | 6-bromodibenzothiophen-3-yl trifluoromethanesulfonate | 86% |

-continued

| | Reactant 1 | Product | Yield |
|---|---|---|---|
| f5 | 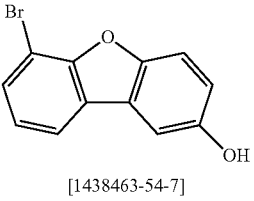 [SMILES: Oc1ccc2oc3c(Br)cccc3c2c1] [1438463-54-7] | 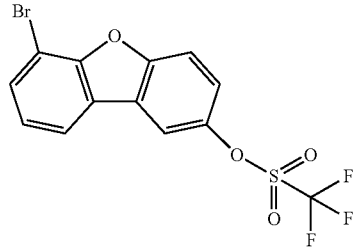 [SMILES: O=S(=O)(Oc1ccc2oc3c(Br)cccc3c2c1)C(F)(F)F] | 89% |
| f6 | 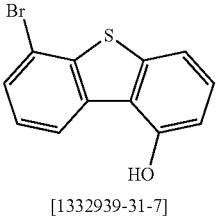 [SMILES: Oc1cccc2sc3c(Br)cccc3c12] [1332939-31-7] | 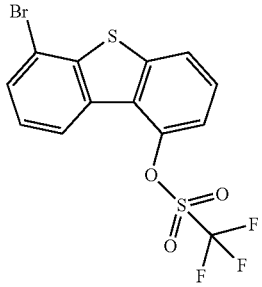 [SMILES: O=S(=O)(Oc1cccc2sc3c(Br)cccc3c12)C(F)(F)F] | 87% | g) 1 Trifluoro-methanesulfonic acid 8-bromo-dibenzofuran-1-yl Ester

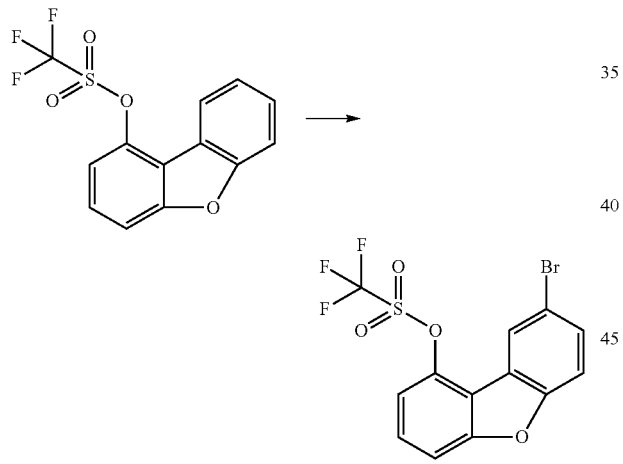

40 g (126 mmol) of trifluoromethanesulfonic acid dibenzofuran-1-yl-ester are suspended in 76 ml (506 mmol) of trifluoromethanesulfonic acid. 52 g (291 mmol) of NBS are added little by little o this suspension and stirred for 2 hours in the dark. Then, the reaction mixture is mixed with water/ice, the solid is separated and washed with ethanol. The residue is recrystallized from toluene.

The yield is 33 g (84 mmol), corresponding to 66% of theory.

In the case of the thiophene derivatives of the present invention, elemental bromine is used in place of NBS.

The following compounds are prepared analogously:

| | Reactant 1 | Product | Yield |
|---|---|---|---|
| g1 | 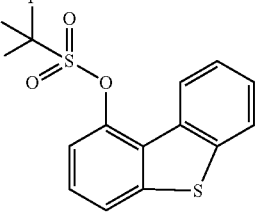 | 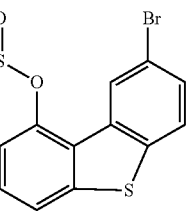 | 77% | h) 1-Bromo-8-phenanthren-9-yl-dibenzofuran

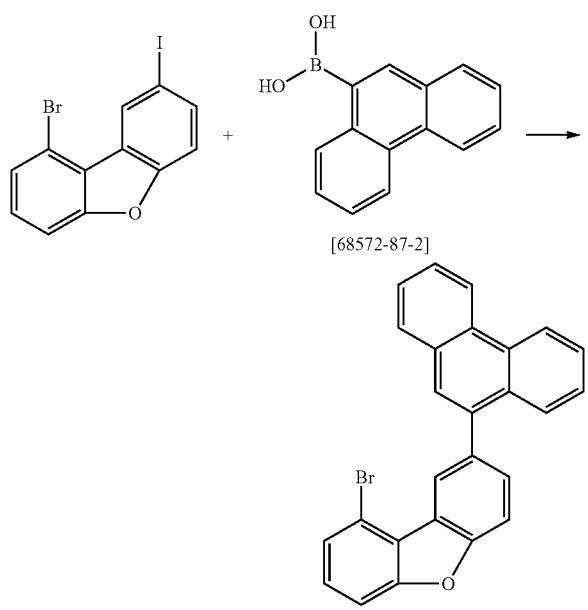

[68572-87-2]

24.4 g (110.0 mmol) of phenanthrene-9-boronic acid, 41 g (110.0 mmol) of 1-bromo-8-iodo-dibenzofuran, and 26 g (210.0 mmol) of sodium carbonate are suspended in 500 mL ethylene glycol diaminether and 500 mL water. 913 mg (3.0 mmol) of tri-o-tolylphosphine are first added to this mixture, and then 112 mg (0.5 mmol) of palladium (II) acetate are added to the mixture. Subsequently, the reaction mixture is heated under reflux during 16 h. After cooling, the organic phase is separated, filtered through silica gel and then concentrated to dryness. The residue is recrystallized from toluene and dichloromethane/Heptan.

The yield is 37 g (90 mmol) corresponding to 82% of theory.

The following compounds are prepared analogously:

| | Reactant 1 | Reactant 2 | Produkt | Yield |
|---|---|---|---|---|
| h1 | (Br, I-dibenzofuran) | naphthalen-1-yl-B(OH)₂ [13922-41-3] | 1-bromo-8-(naphthalen-1-yl)dibenzofuran | 70% |
| h2 | (Br, I-dibenzofuran) | naphthalen-2-yl-B(OH)₂ [32316-92-0] | 1-bromo-8-(naphthalen-2-yl)dibenzofuran | 73% |

-continued

| | Reactant 1 | Reactant 2 | Produkt | Yield |
|---|---|---|---|---|
| h3 | | [13922-41-3] | | 66% |
| h4 | | [1269818-63-4] | | 64% |
| h5 | | [1242770-93-9] | | 62% |
| h6 | | [11188094-46-3] | | 61% |

-continued
| | Reactant 1 | Reactant 2 | Produkt | Yield |
|---|---|---|---|---|
| h7 | 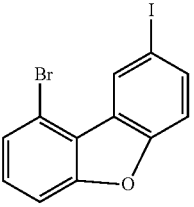 [SMILES: Brc1cccc2oc3ccc(I)cc3c12] | 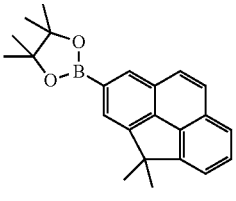 [SMILES: CC1(C)c2cccc3ccc4cc(B5OC(C)(C)C(C)(C)O5)cc1c4c23]
[1021857-39-5] | 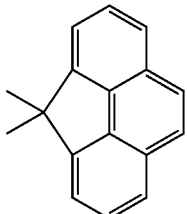 | 65% |
| h8 | 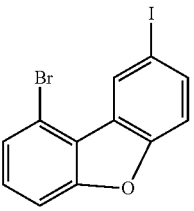 [SMILES: Brc1cccc2oc3ccc(I)cc3c12] | 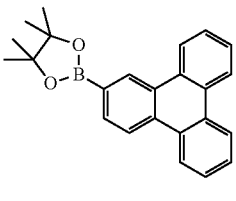 [SMILES: CC1(C)OB(c2ccc3c4ccccc4c4ccccc4c3c2)OC1(C)C]
[890042-13-4] | 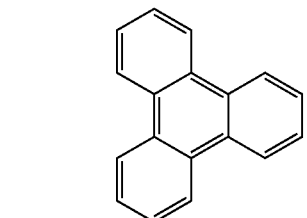 | 63% |
| h9 | 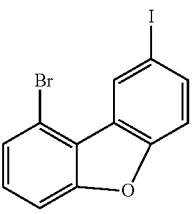 [SMILES: Brc1cccc2oc3ccc(I)cc3c12] | 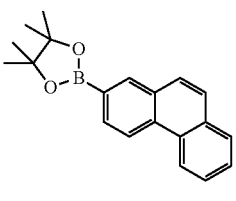 [SMILES: CC1(C)OB(c2ccc3c(ccc4ccccc43)c2)OC1(C)C]
[895137-83-4] | 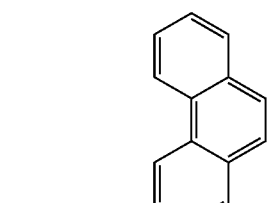 | 61% |
| h10 | 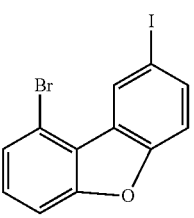 [SMILES: Brc1cccc2oc3ccc(I)cc3c12] | 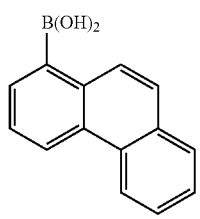 [SMILES: OB(O)c1cccc2c1ccc1ccccc12]
[146746-63-6] | 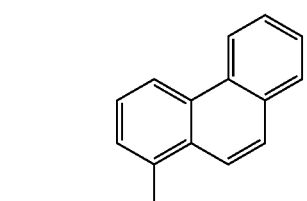 | 71% |

| | Reactant 1 | Reactant 2 | Produkt | Yield |
|---|---|---|---|---|
| h11 | 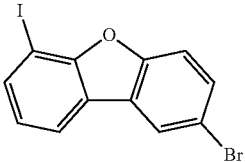 [SMILES: Brc1ccc2oc3c(I)cccc3c2c1] [1643716-58-8] | 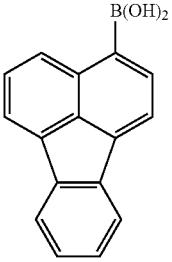 [SMILES: OB(O)c1ccc2c3c(cccc13)-c1ccccc1-2] [359012-63-8] | 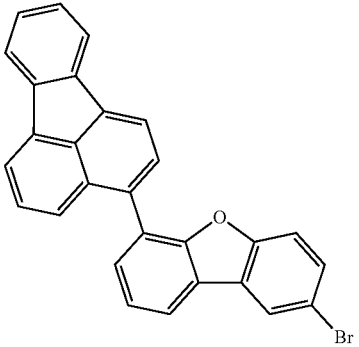 [SMILES: Brc1ccc2oc3c(-c4ccc5c6c(cccc46)-c4ccccc4-5)cccc3c2c1] | 70% |
| h12 | 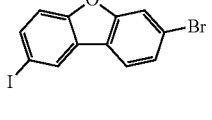 [1627589-28-9] | 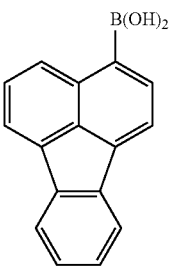 [SMILES: OB(O)c1ccc2c3c(cccc13)-c1ccccc1-2] [359012-63-8] | 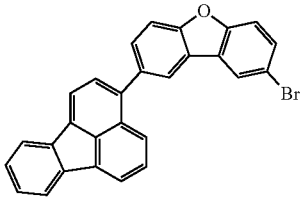 [SMILES: Brc1ccc2oc3ccc(-c4ccc5c6c(cccc46)-c4ccccc4-5)cc3c2c1] | 76% |
| h13 | 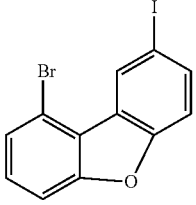 [SMILES: Brc1cccc2oc3ccc(I)cc3c12] | 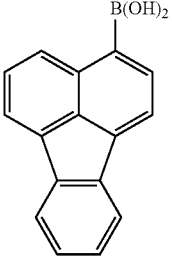 [SMILES: OB(O)c1ccc2c3c(cccc13)-c1ccccc1-2] [359012-63-8] | 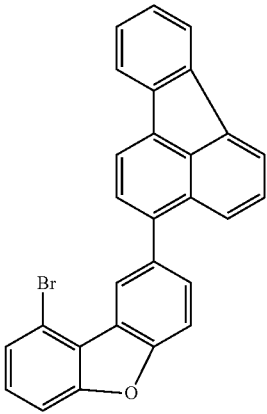 [SMILES: Brc1cccc2oc3ccc(-c4ccc5c6c(cccc46)-c4ccccc4-5)cc3c12] | 60% |
| h14 | 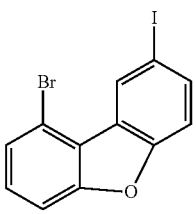 [SMILES: Brc1cccc2oc3ccc(I)cc3c12] | 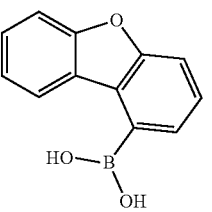 [SMILES: OB(O)c1cccc2oc3ccccc3c12] [162607-19-4] | 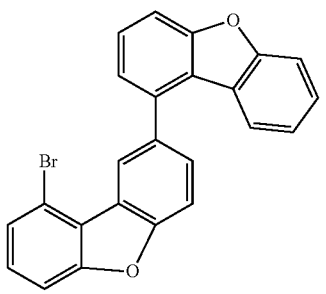 [SMILES: Brc1cccc2oc3ccc(-c4cccc5oc6ccccc6c45)cc3c12] | 62% |

-continued
| | Reactant 1 | Reactant 2 | Produkt | Yield |
|---|---|---|---|---|
| h15 | 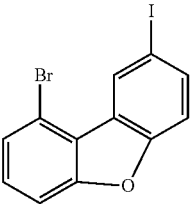 [SMILES: Brc1cccc2oc3ccc(I)cc3c12] | 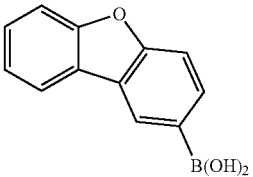 [SMILES: OB(O)c1ccc2oc3ccccc3c2c1] [402936-15-6] | 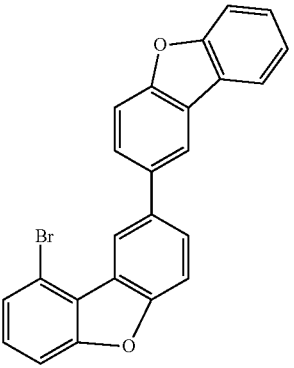 [SMILES: Brc1cccc2oc3ccc(-c4ccc5oc6ccccc6c5c4)cc3c12] | 63% |
| h16 | 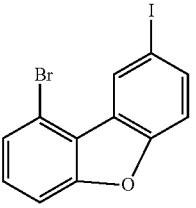 [SMILES: Brc1cccc2oc3ccc(I)cc3c12] | 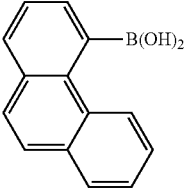 [SMILES: OB(O)c1cccc2ccc3ccccc3c12] [1269818-63-4] | 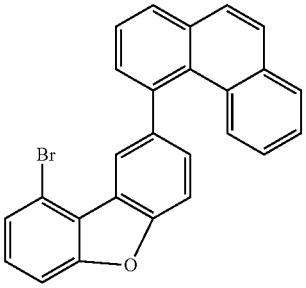 [SMILES: Brc1cccc2oc3ccc(-c4cccc5ccc6ccccc6c45)cc3c12] | 63% |
| h17 | 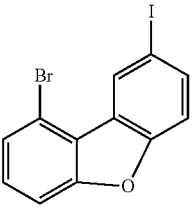 [SMILES: Brc1cccc2oc3ccc(I)cc3c12] | 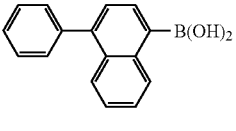 [372521-91-0] | 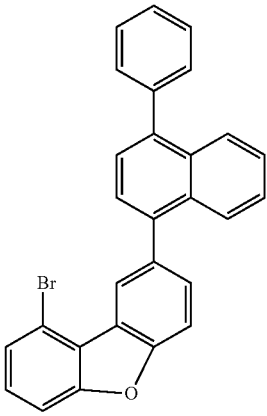 [SMILES: Brc1cccc2oc3ccc(-c4ccc(-c5ccccc5)c5ccccc45)cc3c12] | 61% |
| h18 | 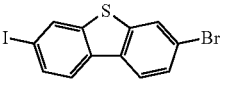 [1448787-84-5] | 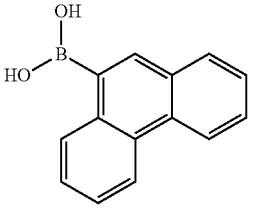 [SMILES: OB(O)c1cc2ccccc2c2ccccc12] [68572-87-2] | 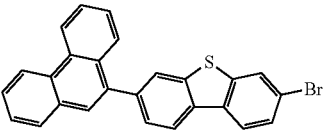 [SMILES: Brc1ccc2c(c1)sc1cc(-c3cc4ccccc4c4ccccc34)ccc12] | 60% |

-continued

| | Reactant 1 | Reactant 2 | Produkt | Yield |
|---|---|---|---|---|
| h19 | [1110690-60-2] | [359012-63-8] | | 67% |
| h20 | [1643716-57-7] | [68572-87-2] | | 59% |
| h21 | [693226-82-3] | [359012-63-8] | | 65% |
| h22 | [378781-73-8] | [359012-63-8] | | 62% |
| h23 | [916435-45-5] | [68572-87-2] | | 65% |

-continued
| | Reactant 1 | Reactant 2 | Produkt | Yield |
|---|---|---|---|---|
| h24 | 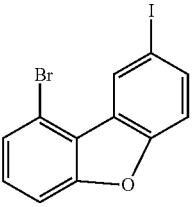 [SMILES: Brc1cccc2oc3ccc(I)cc3c12] | 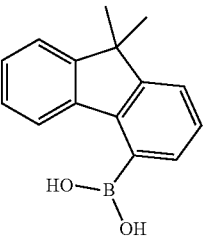 [SMILES: CC1(C)c2ccccc2-c2c(B(O)O)cccc21]<br>[1246022-50-3] | 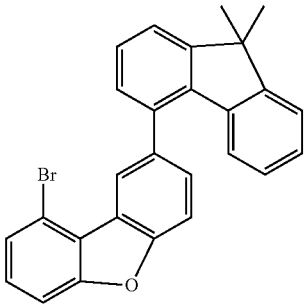 [SMILES: CC1(C)c2ccccc2-c2c(-c3ccc4oc5cccc(Br)c5c4c3)cccc21] | 67% |
| h25 | 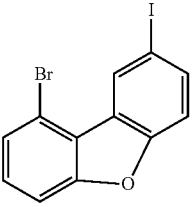 [SMILES: Brc1cccc2oc3ccc(I)cc3c12] | 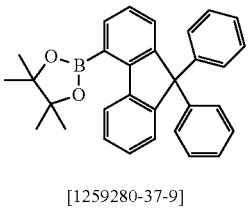<br>[1259280-37-9] | 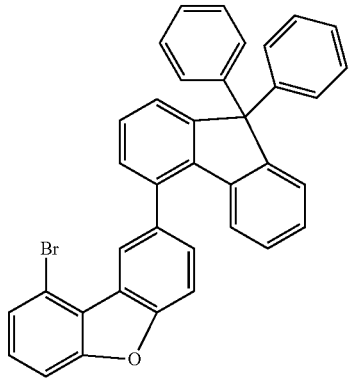 [SMILES: Brc1cccc2oc3ccc(-c4cccc5c4-c4ccccc4C5(c4ccccc4)c4ccccc4)cc3c12] | 53% |
| h26 | 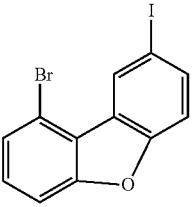 [SMILES: Brc1cccc2oc3ccc(I)cc3c12] | 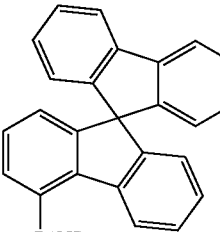<br>[1421789-05-0] | 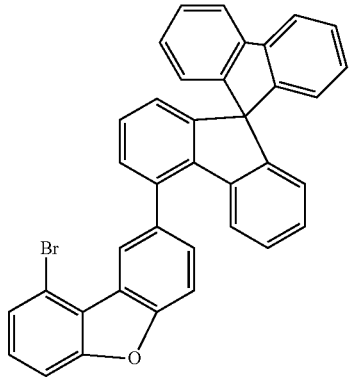 | 69% |
| h27 | 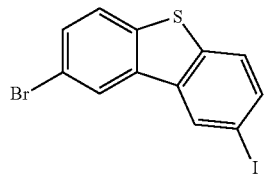<br>[1206544-88-8] | 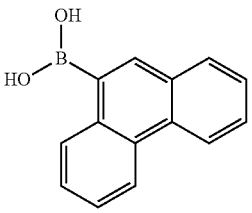 [SMILES: OB(O)c1cc2ccccc2c2ccccc12]<br>[68572-87-2] | 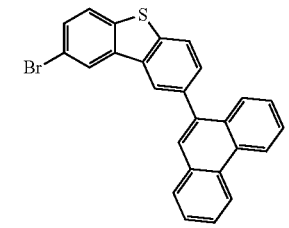 [SMILES: Brc1ccc2sc3ccc(-c4cc5ccccc5c5ccccc45)cc3c2c1] | 62% |
| h28 | 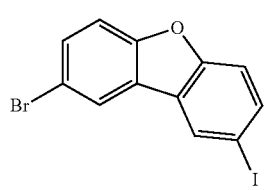<br>[916435-41-1] | 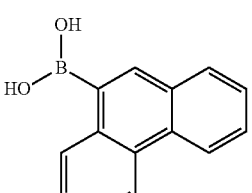<br>[68572-87-2] | 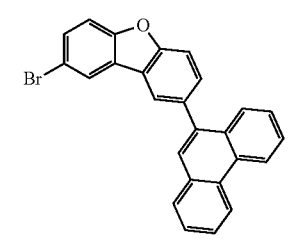 [SMILES: Brc1ccc2oc3ccc(-c4cc5ccccc5c5ccccc45)cc3c2c1] | 61% |

-continued
| Reactant 1 | Reactant 2 | Produkt | Yield |
|---|---|---|---|
| h29 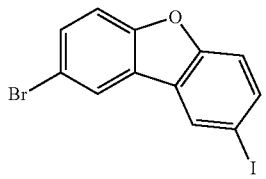 [SMILES: Brc1ccc2oc3ccc(I)cc3c2c1] [916435-41-1] | 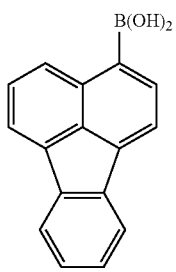 [SMILES: OB(O)c1ccc2c3c(cccc13)-c1ccccc1-2] [359012-63-8] | 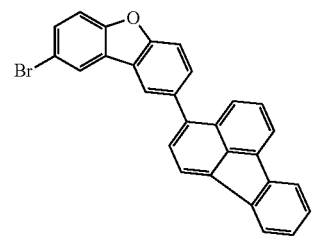 [SMILES: Brc1ccc2oc3ccc(-c4ccc5c6c(cccc46)-c4ccccc4-5)cc3c2c1] | 58% |
| h30 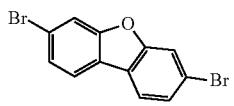 [67019-91-4] | 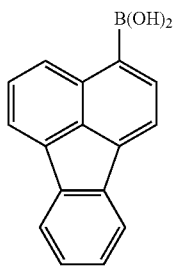 [SMILES: OB(O)c1ccc2c3c(cccc13)-c1ccccc1-2] [359012-63-8] | 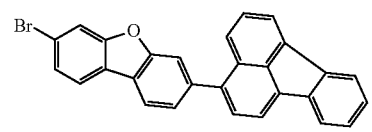 [SMILES: Brc1ccc2c(c1)oc1cc(-c3ccc4c5c(cccc35)-c3ccccc3-4)ccc12] | 45% |
i) 1-Fluoranthen-3-yl-8-phenanthren-9-yl-dibenzofuran
-continued
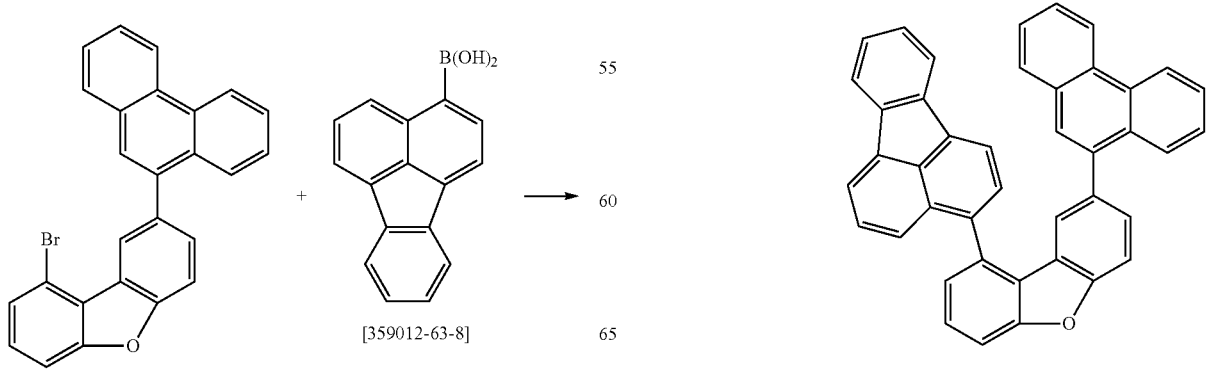

65.9 g (156 mmol) of 1-bromo-8-phenanthren-9-yl-dibenzofuran, 36.7 g (170 mmol) of fluoranthene-3-boronic acid and 36 g (340 mmol) of sodium carbonate are suspended in 1000 mL ethylene glycol diaminether and 280 mL water. 1.8 g (1.5 mmol) of tetrakis (triphenylphosphine) palladium (0) are added to the suspension and the reaction mixture is heated under reflux during 16 h. After cooling, the organic phase is separated, filtered through silica gel, washed three times with 200 mL water and then concentrated to dryness. The product is washed via column chromatography on silica gel with toluene/heptane (1:2) and via sublimation in high vacuum (p=5×10$^{-7}$ mbar) (purity 99.9%).

The yield is 53 g (98 mmol), corresponding to 63% of theory.

The following compounds are prepared analogously:

| | Reactant 1 | Reactant 2 | produkt | Yield |
|---|---|---|---|---|
| i1 | 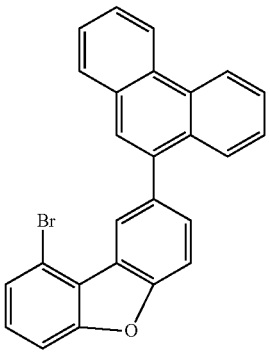 [SMILES: Brc1cccc2oc3ccc(-c4cc5ccccc5c5ccccc45)cc3c12] | 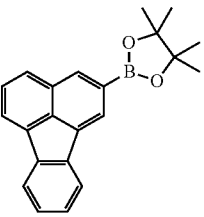 [SMILES: CC1(C)OB(c2cc3c4c(cccc4c2)-c2ccccc2-3)OC1(C)C] [1005770-98-8] | 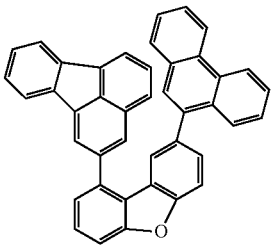 [SMILES: c1ccc2c(c1)-c1cccc3cc(-c4cccc5oc6ccc(-c7cc8ccccc8c8ccccc78)cc6c45)cc-2c13] | 70% |
| i2 | 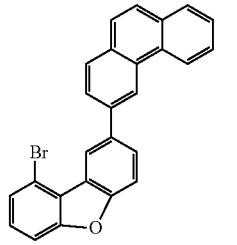 [SMILES: Brc1cccc2oc3ccc(-c4ccc5ccc6ccccc6c5c4)cc3c12] | 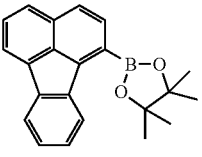 [SMILES: CC1(C)OB(c2ccc3cccc4c3c2-c2ccccc2-4)OC1(C)C] [1005770-97-7] | 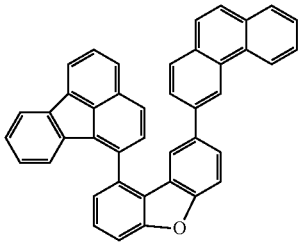 | 77% |
| i3 | 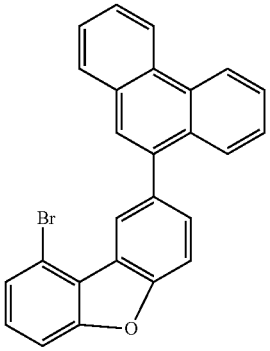 [SMILES: Brc1cccc2oc3ccc(-c4cc5ccccc5c5ccccc45)cc3c12] | 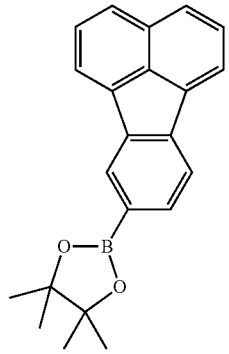 [SMILES: CC1(C)OB(c2ccc3c(c2)-c2cccc4cccc-3c24)OC1(C)C] [944418-47-7] | 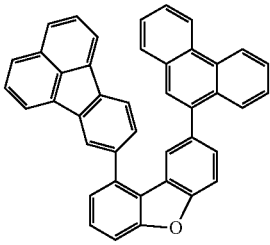 [SMILES: c1cc2c3c(cccc3c1)-c1cc(-c3cccc4oc5ccc(-c6cc7ccccc7c7ccccc67)cc5c34)ccc1-2] | 73% |
| i4 | 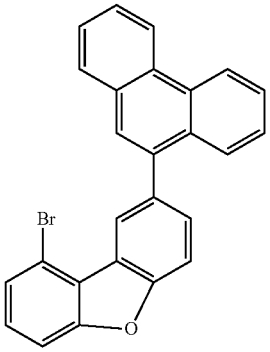 [SMILES: Brc1cccc2oc3ccc(-c4cc5ccccc5c5ccccc45)cc3c12] | 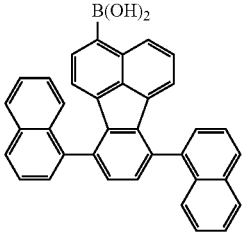 [SMILES: OB(O)c1ccc2c3c(cccc13)-c1c(-c3cccc4ccccc34)ccc(-c3cccc4ccccc34)c1-2] [370084-57-4] | 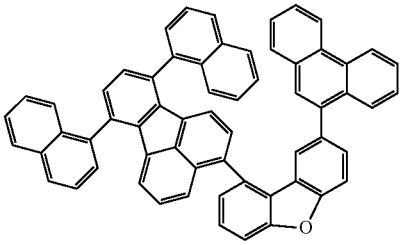 [SMILES: c1ccc2c(-c3ccc(-c4cccc5ccccc45)c4c3-c3cccc5c(-c6cccc7oc8ccc(-c9cc%10ccccc%10c%10ccccc9%10)cc8c67)ccc-4c35)cccc2c1] | 61% |

-continued
| | Reactant 1 | Reactant 2 | produkt | Yield |
|---|---|---|---|---|
| i5 | 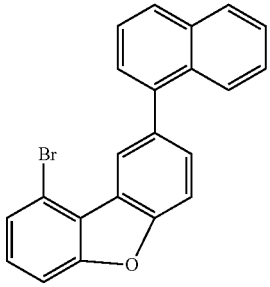 [SMILES: Brc1cccc2oc3ccc(-c4cccc5ccccc45)cc3c12] | 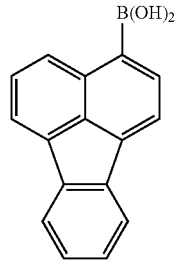 [SMILES: OB(O)c1ccc2c3c(cccc13)-c1ccccc1-2] [359012-63-8] | 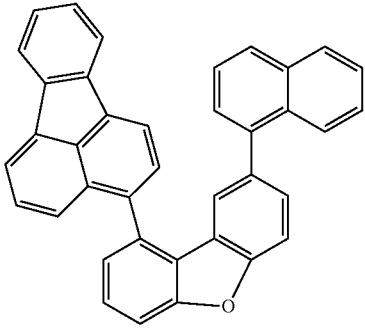 [SMILES: c1ccc2c(c1)-c1cccc3c(-c4cccc5oc6ccc(-c7cccc8ccccc78)cc6c45)ccc-2c13] | 78% |
| i6 | 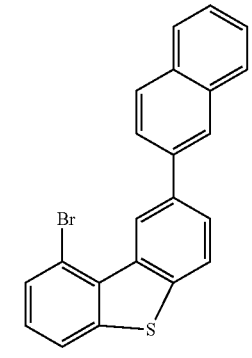 [SMILES: Brc1cccc2sc3ccc(-c4ccc5ccccc5c4)cc3c12] | 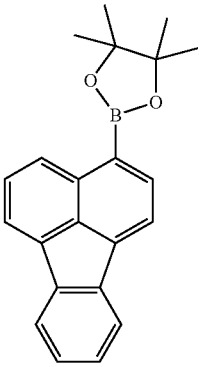 [SMILES: CC1(C)OB(c2ccc3c4c(cccc24)-c2ccccc2-3)OC1(C)C] [863878-53-9] | 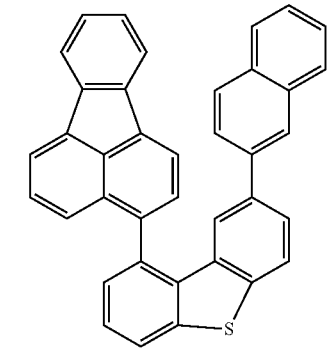 [SMILES: c1ccc2c(c1)-c1cccc3c(-c4cccc5sc6ccc(-c7ccc8ccccc8c7)cc6c45)ccc-2c13] | 72% |
| i7 | 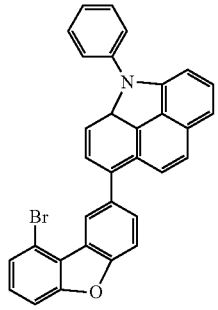 | 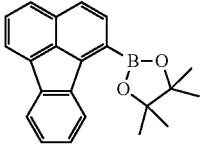 [SMILES: CC1(C)OB(c2ccc3cccc4c3c2-c2ccccc2-4)OC1(C)C] [1005770-97-7] | 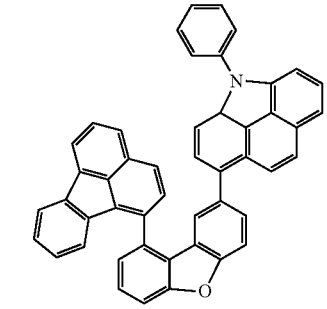 | 74% |
| i8 | 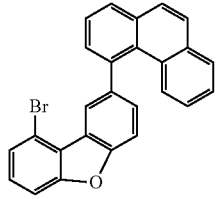 [SMILES: Brc1cccc2oc3ccc(-c4cccc5ccc6ccccc6c45)cc3c12] | 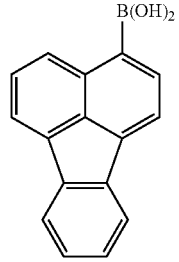 [SMILES: OB(O)c1ccc2c3c(cccc13)-c1ccccc1-2] [359012-63-8] | 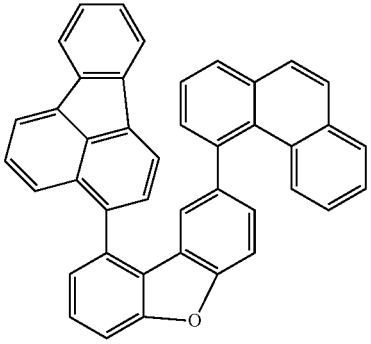 [SMILES: c1ccc2c(c1)-c1cccc3c(-c4cccc5oc6ccc(-c7cccc8ccc9ccccc9c78)cc6c45)ccc-2c13] | 75% |

-continued

| | Reactant 1 | Reactant 2 | produkt | Yield |
|---|---|---|---|---|
| i9 | | [944418-47-7] | | 54% |
| i10 | | [944418-47-7] | | 69% |
| i11 | | [944418-47-7] | | 71% |

-continued

| | Reactant 1 | Reactant 2 | produkt | Yield |
|---|---|---|---|---|
| i12 | | [359012-63-8] | | 70% |
| i13 | | [359012-63-8] | | 67% |
| i14 | | [359012-63-8] | | 72% |

-continued

| | Reactant 1 | Reactant 2 | produkt | Yield |
|---|---|---|---|---|
| i15 | | [68572-87-2] | | 71% |
| i16 | | [68572-87-2] | | 75% |
| i17 | | [359012-63-8] | | 68% |
| i18 | | [359012-63-8] | | 69% |

-continued

| | Reactant 1 | Reactant 2 | produkt | Yield |
|---|---|---|---|---|
| i19 | | [359012-63-8] | | 63% |
| i20 | | [68572-87-2] | | 76% |
| i21 | | [359012-63-8] | | 68% |
| i22 | | [402936-15-6] | | 67% |
| i23 | | [359012-63-8] | | 72% |

-continued

| | Reactant 1 | Reactant 2 | produkt | Yield |
|---|---|---|---|---|
| i24 | | [359012-63-8] | | 65% |
| i25 | | [359012-63-8] | | 61% |
| i26 | | [359012-63-8] | | 58% |
| i27 | | [359012-63-8] | | 65% |
| i28 | | [359012-63-8] | | 69% |

-continued
| | Reactant 1 | Reactant 2 | produkt | Yield |
|---|---|---|---|---|
| i29 | 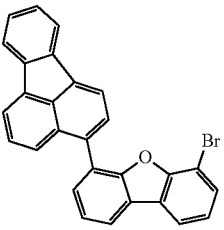 [SMILES: Brc1cccc2c1oc1c(-c3ccc4c5c(cccc35)-c3ccccc3-4)cccc12] | 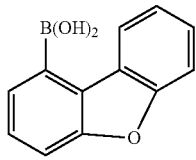 [SMILES: OB(O)c1cccc2oc3ccccc3c12] | 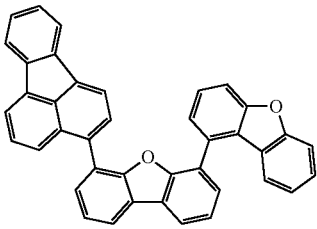 [SMILES: c1ccc2c(c1)-c1cccc3c(-c4cccc5c4oc4c(-c6cccc7oc8ccccc8c67)cccc45)ccc-2c13] | 65% |
| i30 | 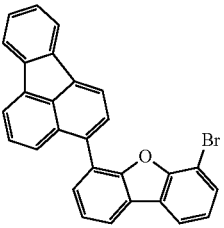 [SMILES: Brc1cccc2c1oc1c(-c3ccc4c5c(cccc35)-c3ccccc3-4)cccc12] | 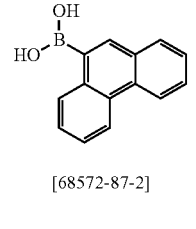<br>[68572-87-2] | 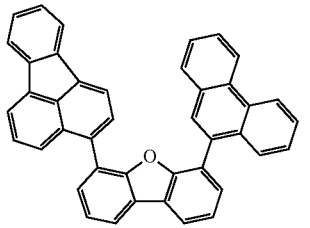 [SMILES: c1ccc2c(c1)-c1cccc3c(-c4cccc5c4oc4c(-c6cc7ccccc7c7ccccc67)cccc45)ccc-2c13] | 66% |
| i31 | 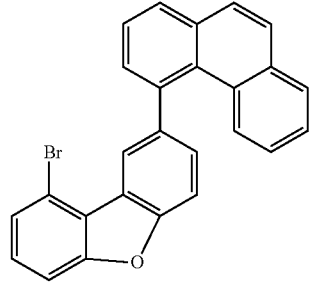 [SMILES: Brc1cccc2oc3ccc(-c4cccc5ccc6ccccc6c45)cc3c12] | 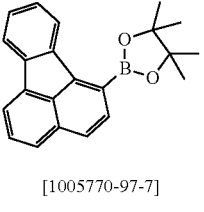<br>[1005770-97-7] | 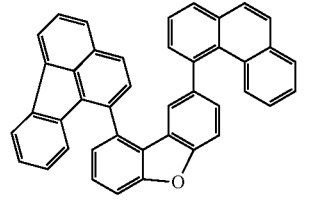 [SMILES: c1ccc2c(c1)-c1cccc3ccc(-c4cccc5oc6ccc(-c7cccc8ccc9ccccc9c78)cc6c45)c-2c13] | 64% |
| i32 | 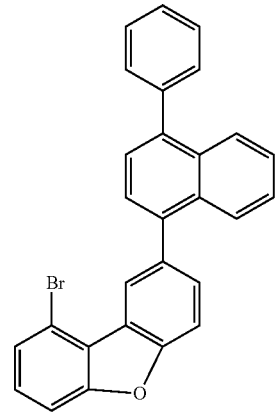 [SMILES: Brc1cccc2oc3ccc(-c4ccc(-c5ccccc5)c5ccccc45)cc3c12] | 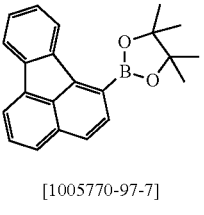<br>[1005770-97-7] | 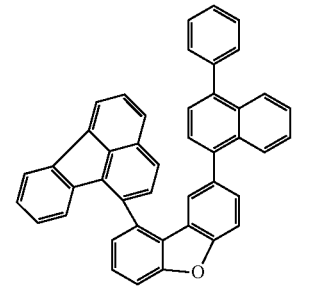 [SMILES: c1ccc(-c2ccc(-c3ccc4oc5cccc(-c6ccc7cccc8c7c6-c6ccccc6-8)c5c4c3)c3ccccc23)cc1] | 58% |
| i33 | 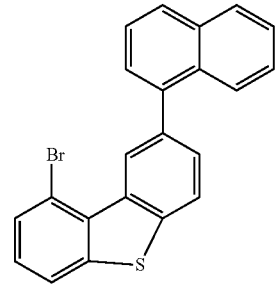 [SMILES: Brc1cccc2sc3ccc(-c4cccc5ccccc45)cc3c12] | 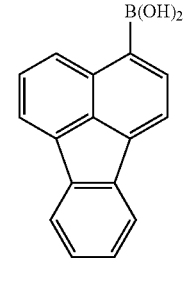 [SMILES: OB(O)c1ccc2c3c(cccc13)-c1ccccc1-2]<br>[359012-63-8] | 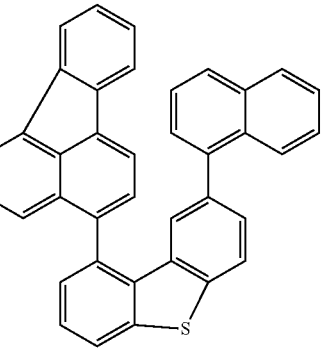 | 57% |

-continued

| | Reactant 1 | Reactant 2 | produkt | Yield |
|---|---|---|---|---|
| i34 | | [359012-63-8] | | 61% |
| i35 | | [359012-63-8] | | 65% |
| i36 | | [359012-63-8] | | 67% |
| i37 | | [100124-06-9] | | 65% |
| i38 | | [1251825-71-4] | | 66% |

-continued

| | Reactant 1 | Reactant 2 | produkt | Yield |
|---|---|---|---|---|
| i39 | (structure: Br-dibenzofuran-fluoranthene) | (1-naphthalene boronic acid) [13922-41-3] | (naphthyl-dibenzofuran-fluoranthene product) | 71% |
| i40 | (structure: Br-dibenzofuran-fluoranthene) | (phenanthrene-9-boronic acid) [68572-87-2] | (phenanthryl-dibenzofuran-fluoranthene product) | 74% | j) Trifluoro-methanesulfonic acid 8-fluoranthen-3-yl-dibenzofuran-1-yl ester

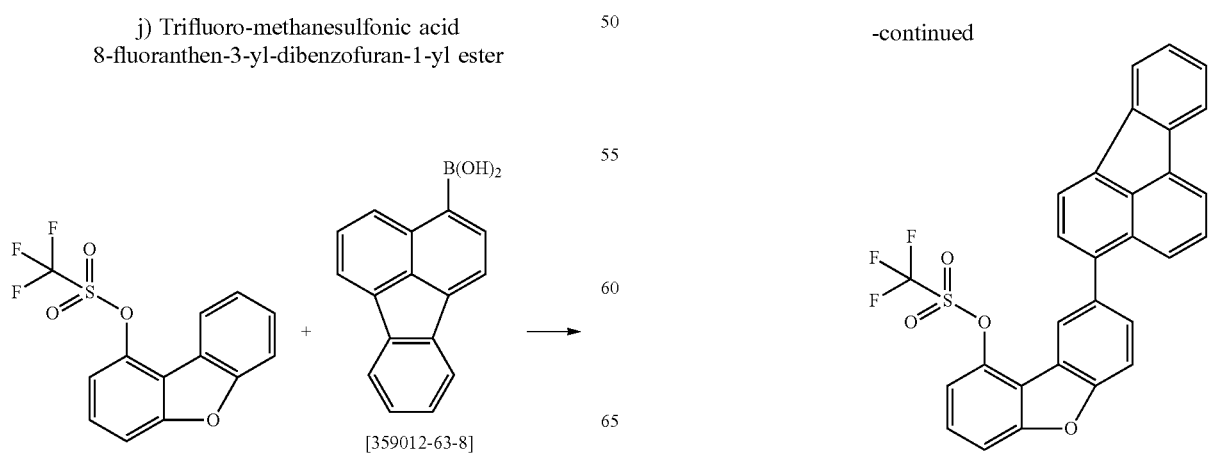

-continued 41 g (190 mmol) of 1-trifluoro-methanesulfonic acid 8-bromo-dibenzofuran-1-yl ester, 56.5 g (220 mmol) fluoranthen-3-boronic acid and 57 g (410 mmol) of potassium carbonate are suspended in 1000 mL toluene and 100 mL water. 1.8 g (1.5 mmol) of tetrakis (triphenylphosphine) palladium (0) are added and the reaction mixture is heated under reflux for 16 h. After cooling, the organic phase is separated, filtered through silica gel, washed three times with 200 mL water and then concentrated to dryness. The product is washed via column chromatography on silica gel with toluene/heptane (1:2) and via sublimation in high vacuum ($p=5\times10^{-7}$ mbar) (purity 99.9%).

The yield is 76 g (147 mmol), corresponding to 78% of theory.

The following compounds are prepared analogously:

| | Reactant 1 | Reactant 2 | Product | Yield |
|---|---|---|---|---|
| j1 | g1 | [68572-87-2] | | 64% |
| j2 | | [359012-63-8] | | 66% |
| j3 | f4 | [359012-63-8] | | 68% |

-continued
| Reactant 1 | Reactant 2 | Product | Yield |
|---|---|---|---|
| j4 (f5) | [944418-47-7] | | 64% |
| j5 (f6) | [162607-19-4] | | 71% |
k) 8-Fluoranthen-3-yl-1-(4,4,5,5-tetramethyl-[1,3,2]dioxaborolan-2-yl)dibenzofuran
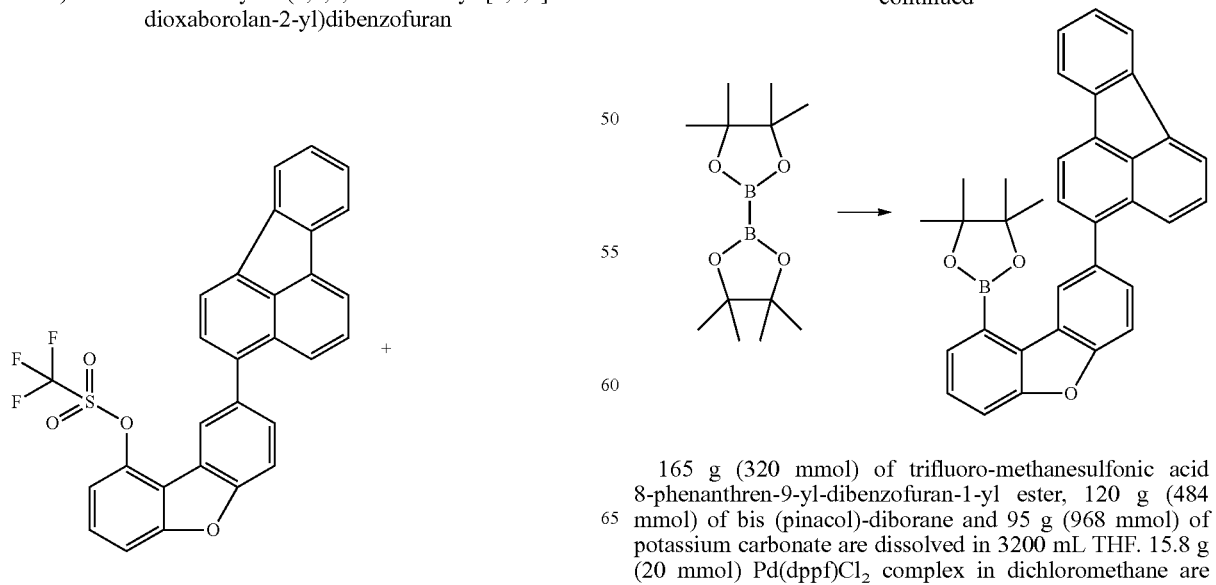
165 g (320 mmol) of trifluoro-methanesulfonic acid 8-phenanthren-9-yl-dibenzofuran-1-yl ester, 120 g (484 mmol) of bis (pinacol)-diborane and 95 g (968 mmol) of potassium carbonate are dissolved in 3200 mL THF. 15.8 g (20 mmol) Pd(dppf)Cl₂ complex in dichloromethane are added to the reaction mixture under inert gas, and the reaction mixture is heated under reflux during 16 h. After cooling, the reaction mixture is mixed with water and the organic phase is separated. The product is then washed via column chromatography on silica gel with toluene/heptane (2:2) and via sublimation under high vacuum ($5 \times 10^{-7}$ p=mbar) (purity 99.9%).

The yield is 88 g (179 mmol), corresponding to 56% of theory.

The following compounds are prepared analogously:

| | Reactant 1 | Product | Yield |
|---|---|---|---|
| k1 | | | 58% |
| k2 | | | 56% |
| k3 | | | 62% |

-continued

| Reactant 1 | Product | Yield |
|---|---|---|
| k4 | | 60% |
| k5 | | 67% |
| k6 | | 63% | l) 8-Fluoranthen-3-yl-[1,1']bi[dibenzofuranyl]
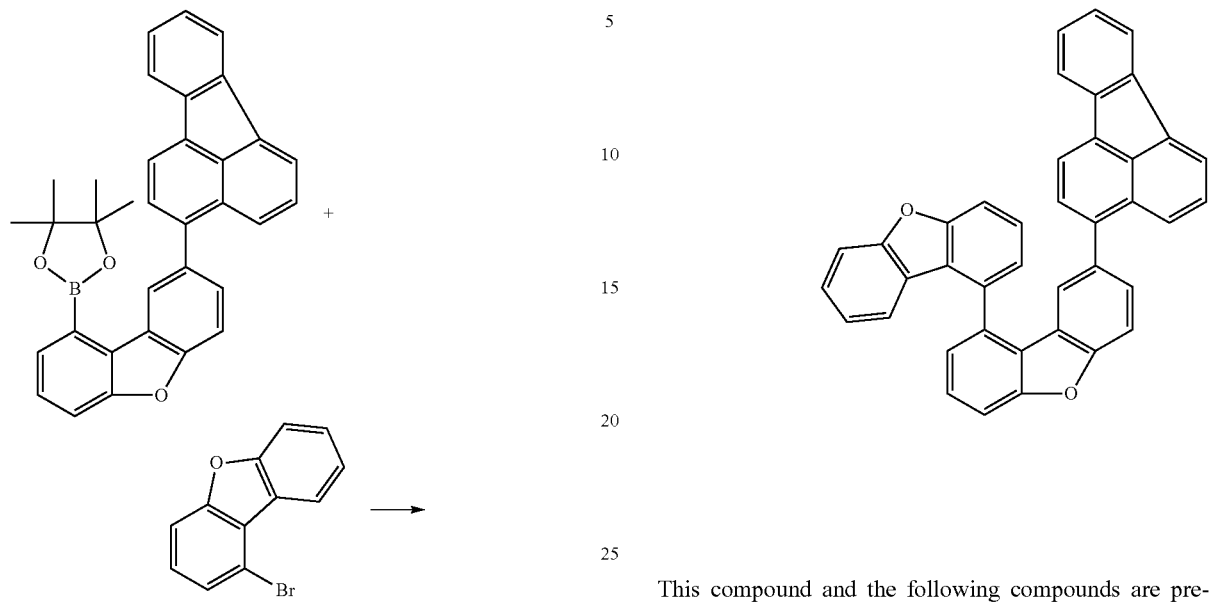
This compound and the following compounds are prepared analogously to method i):

-continued
| | Reactant 1 | Reactant 2 | Product | Yield |
|---|---|---|---|---|
| 13 | 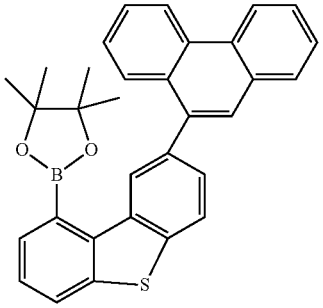 [SMILES: CC1(C)OB(c2cccc3sc4ccc(-c5cc6ccccc6c6ccccc56)cc4c23)OC1(C)C] | 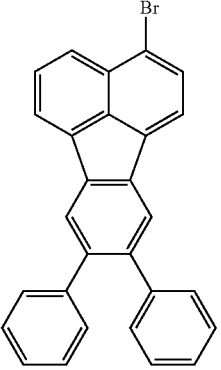 [SMILES: Brc1ccc2c3c(cccc13)-c1cc(-c3ccccc3)c(-c3ccccc3)cc1-2] [1448061-65-1] | 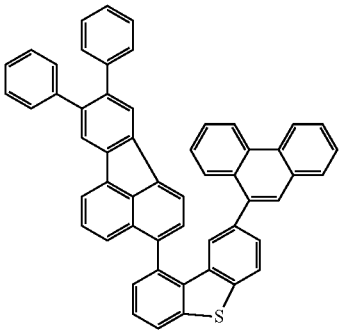 [SMILES: c1ccc(-c2cc3c(cc2-c2ccccc2)-c2ccc(-c4cccc5sc6ccc(-c7cc8ccccc8c8ccccc78)cc6c45)c4cccc-3c24)cc1] | 62% |
| 14 | 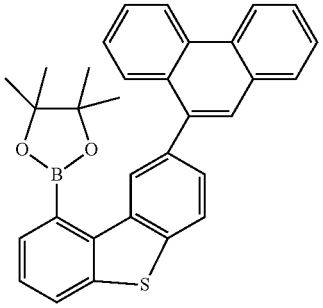 [SMILES: CC1(C)OB(c2cccc3sc4ccc(-c5cc6ccccc6c6ccccc56)cc4c23)OC1(C)C] | 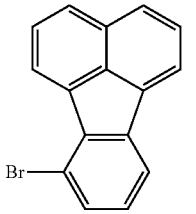 [SMILES: Brc1cccc2c1-c1cccc3cccc-2c13] [30924-53-9] | 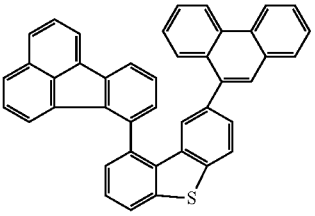 [SMILES: c1cc2c(c(-c3cccc4sc5ccc(-c6cc7ccccc7c7ccccc67)cc5c34)c1)-c1cccc3cccc-2c13] | 67% |
| 15 | 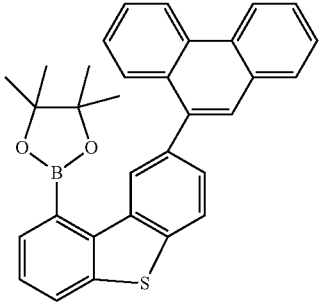 [SMILES: CC1(C)OB(c2cccc3sc4ccc(-c5cc6ccccc6c6ccccc56)cc4c23)OC1(C)C] | 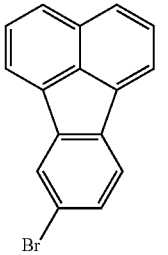 [SMILES: Brc1ccc2c(c1)-c1cccc3cccc-2c13] [2969-58-6] | 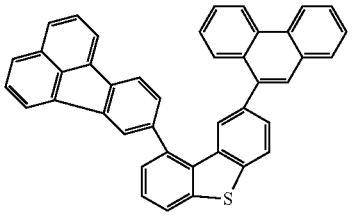 [SMILES: c1cc2c3c(cccc3c1)-c1cc(-c3cccc4sc5ccc(-c6cc7ccccc7c7ccccc67)cc5c34)ccc1-2] | 59% |
| 16 | 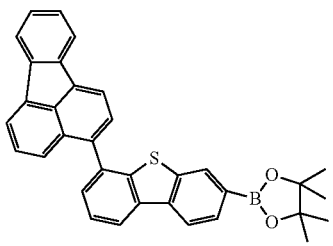 [SMILES: CC1(C)OB(c2ccc3c(c2)sc2c(-c4ccc5c6c(cccc46)-c4ccccc4-5)cccc23)OC1(C)C] | 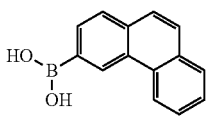 [SMILES: OB(O)c1ccc2ccc3ccccc3c2c1] [11188094-46-3] | 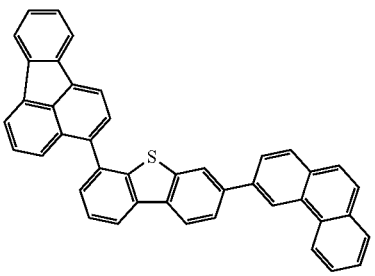 [SMILES: c1ccc2c(c1)-c1cccc3c(-c4cccc5c4sc4cc(-c6ccc7ccc8ccccc8c7c6)ccc45)ccc-2c13] | 63% |

| Reactant 1 | Reactant 2 | Product | Yield |
|---|---|---|---|
| 17 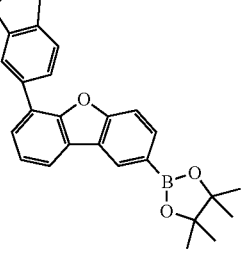 | 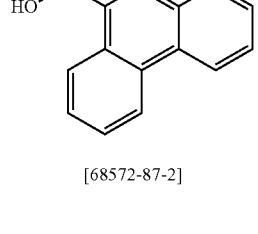[68572-87-2] | 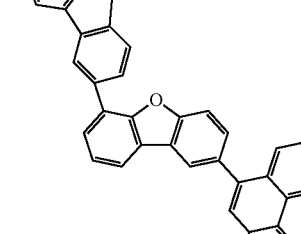 | 65% |
| 18 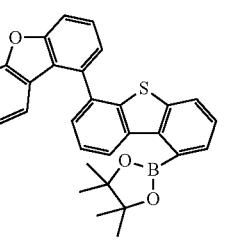 | 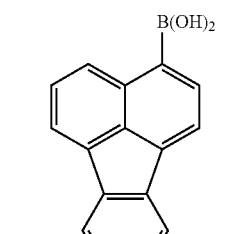[359012-63-8] | 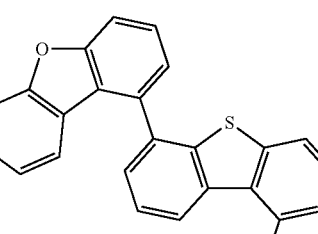 | 68% |
| 19 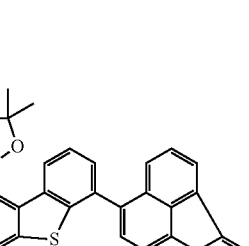 | 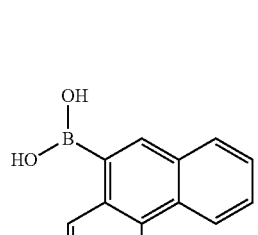[68572-87-2] | 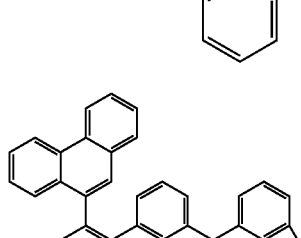 | 73% |

B) Fabrication of OLEDs

The following examples V1 to E13 (see Table 1 and 2) show data of various OLEDs.

Substrate Pre-Treatment of Examples V1-E13:

Glass plates with structured ITO (50 nm, indium tin oxide) form the substrates on which the OLEDs are processed. Before evaporation of the OLED materials, the substrates are pre-baked for 15 minutes at 250° C., followed by an $O_2$ and subsequent Argon plasma treatment.

The OLEDs have in principle the following layer structure: substrate/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The exact layer structure is denoted in Table 1. The materials used for the OLED fabrication are presented in Table 3.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as IC1:M1:TEG1 (55%:35%:10%) here means that material IC1 is present in the layer in a proportion by volume of 55%, M1 is present in the layer in a proportion of 35% and TEG1 is present in the layer in a proportion of 10%. Analogously, the electron-transport layer may also consist of a mixture of two materials.

The OLEDs are characterised by standard methods. For this purpose, the electroluminescence spectra, the current efficiency (CE1000, measured in cd/A at 1000 cd/m$^2$), the luminous efficacy (LE1000, measured in lm/W at 1000 cd/m$^2$), the external quantum efficiency (EQE1000, measured in % at 1000 cd/m$^2$) and the voltage (U1000, measured at 1000 cd/m$^2$ in V) are determined from current/voltage/ luminance characteristic lines (IUL characteristic lines) assuming a Lambertian emission profile. The electroluminescence (EL) spectra are recorded at a luminous density of 1000 cd/m² and the CIE 1931 x and y coordinates are then calculated from the EL spectrum.

The device data of various OLEDs is summarized in Table 2. The examples V1-V3 are comparison examples according to the state-of-the-art. The examples E1-E13 show data of inventive OLEDs.

In the following section several examples are described in more detail to show the advantages of the inventive OLEDs.

Use of Inventive Compounds as Host Material in Phosphorescent OLEDs

The use of the inventive compounds as host material results in significantly improved OLED device data compared to state-of-the-art materials, especially with respect to luminous efficacy.

The use of the inventive materials i39, i36, i37 and i38 as host material in phosphorescent red OLEDs results in 10-20% improved luminous efficacy compared to devices with the materials CE1, CE2 and CE3 (comparison of example V1 with E1, V2 with E2, E3 and the comparison of V3 with V4, respectively).

TABLE 2

OLED device data

| Example | U1000 (V) | CE1000 (cd/A) | LE1000 (lm/W) | EQE 1000 | CIE x/y at 1000 cd/m² |
|---|---|---|---|---|---|
| V1 | 3.5 | 23 | 21 | 21.5% | 0.67/0.33 |
| V2 | 3.4 | 23 | 21 | 22.1% | 0.67/0.33 |
| V3 | 3.5 | 21 | 19 | 21.0% | 0.67/0.33 |
| E1 | 3.4 | 27 | 25 | 22.7% | 0.67/0.34 |
| E2 | 3.3 | 26 | 25 | 23.2% | 0.67/0.33 |
| E3 | 3.3 | 27 | 26 | 23.4% | 0.67/0.33 |
| E4 | 3.4 | 24 | 22 | 22.4% | 0.67/0.33 |
| E5 | 3.5 | 24 | 22 | 22.5% | 0.67/0.33 |
| E6 | 3.5 | 23 | 21 | 22.0% | 0.67/0.33 |
| E7 | 3.3 | 26 | 25 | 23.1% | 0.67/0.33 |
| E8 | 3.4 | 23 | 21 | 22.7% | 0.67/0.33 |
| E9 | 3.4 | 22 | 20 | 22.2% | 0.67/0.33 |
| E10 | 3.3 | 25 | 24 | 22.9% | 0.67/0.33 |
| E11 | 3.6 | 23 | 20 | 22.3% | 0.67/0.33 |
| E12 | 3.5 | 22 | 20 | 21.9% | 0.67/0.33 |
| E13 | 3.4 | 25 | 23 | 23.0% | 0 67/0.33 |

TABLE 1

OLED layer structure

| Bsp. | HIL Dicke | HTL Dicke | EBL Dicke | EML Dicke | HBL Dicke | ETL Dicke |
|---|---|---|---|---|---|---|
| V1 | HATCN 5 nm | SpMA1 125 nm | SpMA3 10 nm | CE1:TER5 (95%:5%) 40 nm | — | ST2:LiQ (50%:50%) 35 nm |
| V2 | HATCN 5 nm | SpMA1 125 nm | SpMA3 10 nm | CE2:TER5 (95%:5%) 40 nm | — | ST2:LiQ (50%:50%) 35 nm |
| V3 | HATCN 5 nm | SpMA1 125 nm | SpMA3 10 nm | CE3:TER5 (95%:5%) 40 nm | — | ST2:LiQ (50%:50%) 35 nm |
| E1 | HATCN 5 nm | SpMA1 125 nm | SpMA3 10 nm | i42:TER5 (95%:5%) 40 nm | — | ST2:LiQ (50%:50%) 35 nm |
| E2 | HATCN 5 nm | SpMA1 125 nm | SpMA3 10 nm | i39:TER5 (95%:5%) 40 nm | — | ST2:LiQ (50%:50%) 35 nm |
| E3 | HATCN 5 nm | SpMA1 125 nm | SpMA3 10 nm | 140:TER5 (95%:5%) 40 nm | — | ST2:LiQ (50%:50%) 35 nm |
| E4 | HATCN 5 nm | SpMA1 125 nm | SpMA3 10 nm | i41:TER5 (95%:5%) 40 nm | — | ST2:LiQ (50%:50%) 35 nm |
| E5 | HATCN 5 nm | SpMA1 125 nm | SpMA3 10 nm | i:TER5 (95%:5%) 40 nm | — | ST2:LiQ (50%:50%) 35 nm |
| E6 | HATCN 5 nm | SpMA1 125 nm | SpMA3 10 nm | i2:TER5 (95%:5%) 40 nm | — | ST2:LiQ (50%:50%) 35 nm |
| E7 | HATCN 5 nm | SpMA1 125 nm | SpMA3 10 nm | i:TER5 (95%:5%) 40 nm | — | ST2:i6 (50%:50%) 35 nm |
| E8 | HATCN 5 nm | SpMA1 125 nm | SpMA3 10 nm | i:TER5 (95%:5%) 40 nm | i10 5 nm | ST2:LiQ (50%:50%) 30 nm |
| E9 | HATCN 5 nm | SpMA1 125 nm | SpMA3 10 nm | i18:TER5 (95%:5%) 40 nm | — | ST2:LiQ (50%:50%) 35 nm |
| E10 | HATCN 5 nm | SpMA1 125 nm | SpMA3 10 nm | i23:TER5 (95%:5%) 40 nm | — | ST2:LiQ (50%:50%) 35 nm |
| E11 | HATCN 5 nm | SpMA1 125 nm | SpMA3 10 nm | i27:TER5 (95%:5%) 40 nm | | ST2:LiQ (50%:50%) 35 nm |
| E12 | HATCN 5 nm | SpMA1 125 nm | SpMA3 10 nm | i34:TER5 (95%:5%) 40 nm | — | ST2:LiQ (50%:50%) 35 nm |
| E13 | HATCN 5 nm | SpMA1 125 nm | SpMA3 10 nm | I1:TER5 (95%:5%) 40 nm | | ST2:LiQ (50%:50%) 35 nm |

TABLE 3
Chemical structures of the OLED materials
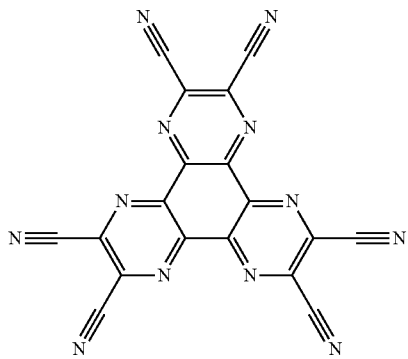 [SMILES: N#Cc1nc2c3nc(C#N)c(C#N)nc3c3nc(C#N)c(C#N)nc3c2nc1C#N]
HATCN
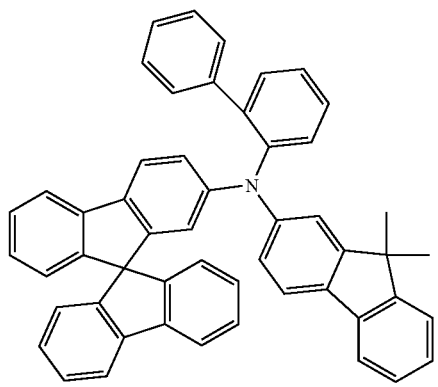 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
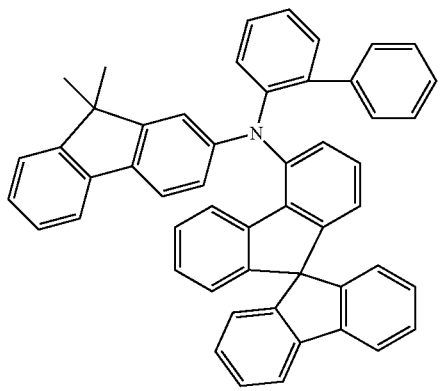 [SMILES: CC1(C)c2ccccc2-c2ccc(N(c3ccccc3-c3ccccc3)c3cccc4c3-c3ccccc3C43c4ccccc4-c4ccccc43)cc21]
SpMA3
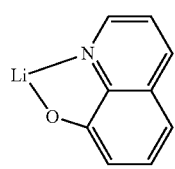
LiQ TABLE 3-continued
Chemical structures of the OLED materials
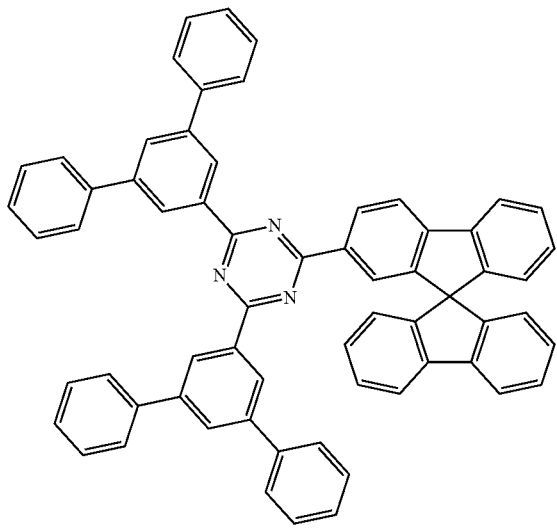 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2
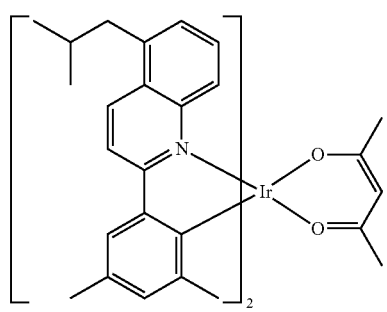
TER5
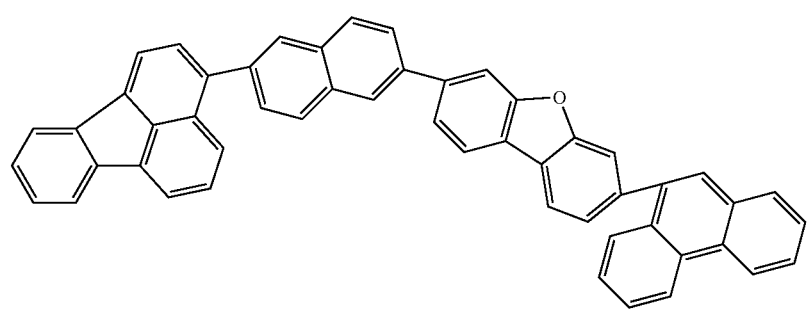 [SMILES: c1ccc2c(c1)-c1cccc3c(-c4ccc5cc(-c6ccc7c(c6)oc6cc(-c8cc9ccccc9c9ccccc89)ccc67)ccc5c4)ccc-2c13]
EP2372803
CE1

TABLE 3-continued
Chemical structures of the OLED materials
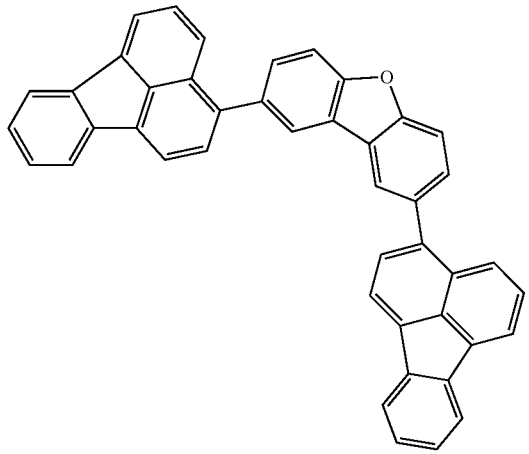 [SMILES: c1ccc2c(c1)-c1cccc3c(-c4ccc5oc6ccc(-c7ccc8c9c(cccc79)-c7ccccc7-8)cc6c5c4)ccc-2c13]
US20120119196A1
CE2
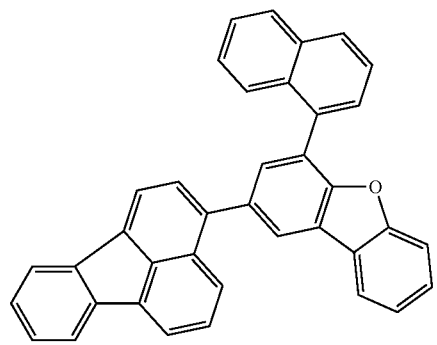 [SMILES: c1ccc2c(c1)-c1cccc3c(-c4cc(-c5cccc6ccccc56)c5oc6ccccc6c5c4)ccc-2c13]
US20140163233
CE3
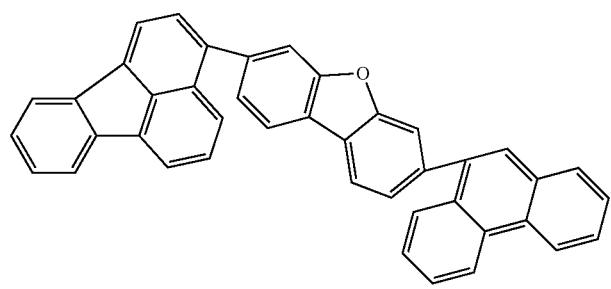 [SMILES: c1ccc2c(c1)-c1cccc3c(-c4ccc5c(c4)oc4cc(-c6cc7ccccc7c7ccccc67)ccc45)ccc-2c13]

TABLE 3-continued
Chemical structures of the OLED materials
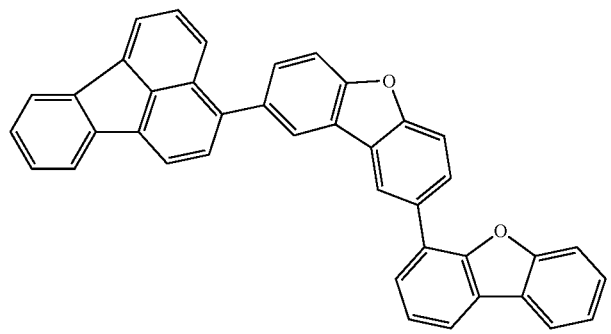 [SMILES: c1ccc2c(c1)-c1cccc3c(-c4ccc5oc6ccc(-c7cccc8c7oc7ccccc78)cc6c5c4)ccc-2c13]
i39
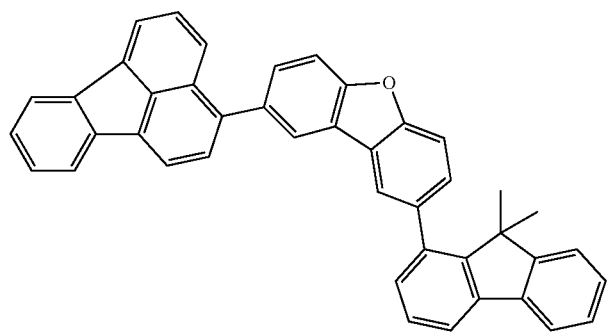 [SMILES: CC1(C)c2ccccc2-c2cccc(-c3ccc4oc5ccc(-c6ccc7c8c(cccc68)-c6ccccc6-7)cc5c4c3)c21]
i40
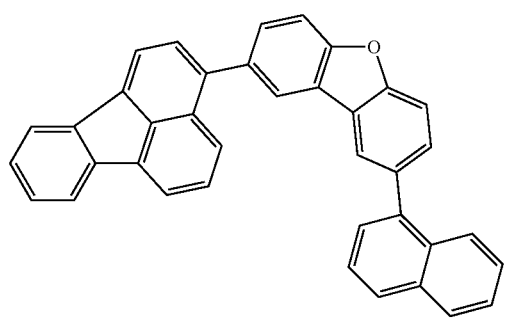 [SMILES: c1ccc2c(c1)-c1cccc3c(-c4ccc5oc6ccc(-c7cccc8ccccc78)cc6c5c4)ccc-2c13]
i41
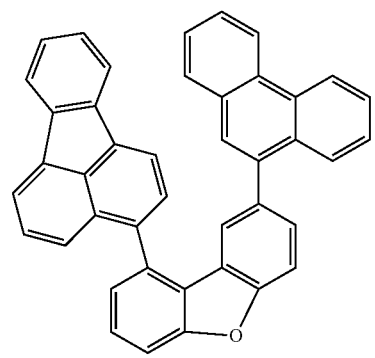 [SMILES: c1ccc2c(c1)-c1cccc3c(-c4cccc5oc6ccc(-c7cc8ccccc8c8ccccc78)cc6c45)ccc-2c13]
i

TABLE 3-continued
Chemical structures of the OLED materials
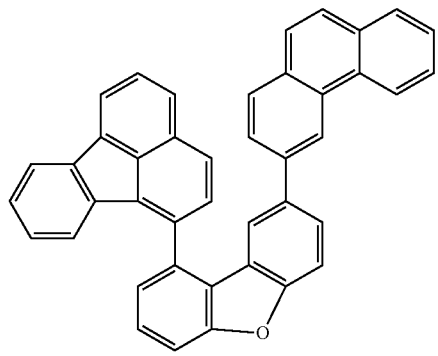 [SMILES: c1ccc2c(c1)-c1cccc3ccc(-c4cccc5oc6ccc(-c7ccc8ccc9ccccc9c8c7)cc6c45)c-2c13]
i2
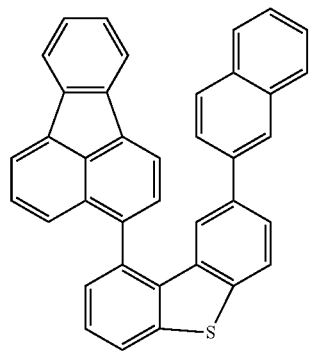 [SMILES: c1ccc2c(c1)-c1cccc3c(-c4cccc5sc6ccc(-c7ccc8ccccc8c7)cc6c45)ccc-2c13]
i6
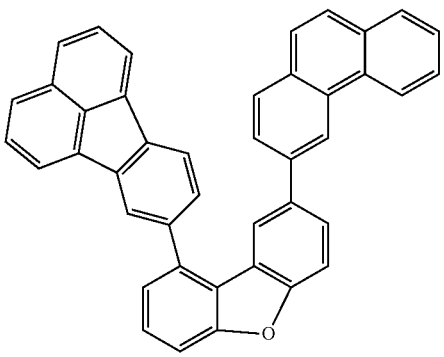 [SMILES: c1cc2c3c(cccc3c1)-c1cc(-c3cccc4oc5ccc(-c6ccc7ccc8ccccc8c7c6)cc5c34)ccc1-2]
i10
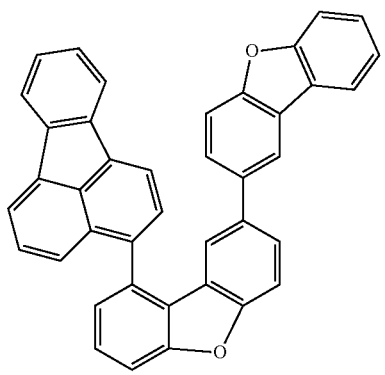 [SMILES: c1ccc2c(c1)-c1cccc3c(-c4cccc5oc6ccc(-c7ccc8oc9ccccc9c8c7)cc6c45)ccc-2c13]
i18

TABLE 3-continued
Chemical structures of the OLED materials
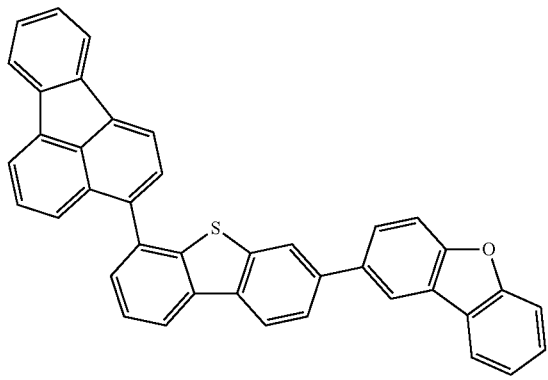 [SMILES: c1ccc2c(c1)-c1cccc3c(-c4cccc5c4sc4cc(-c6ccc7oc8ccccc8c7c6)ccc45)ccc-2c13]
i22
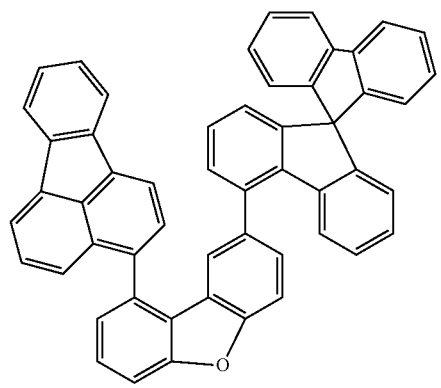 [SMILES: c1ccc2c(c1)-c1cccc3c(-c4cccc5oc6ccc(-c7cccc8c7-c7ccccc7C87c8ccccc8-c8ccccc87)cc6c45)ccc-2c13]
i26
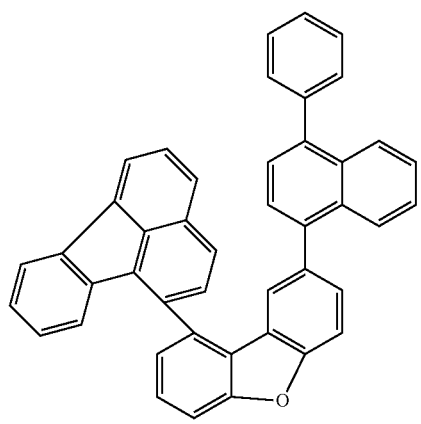 [SMILES: c1ccc(-c2ccc(-c3ccc4oc5cccc(-c6ccc7cccc8c7c6-c6ccccc6-8)c5c4c3)c3ccccc23)cc1]
i32

TABLE 3-continued

Chemical structures of the OLED materials

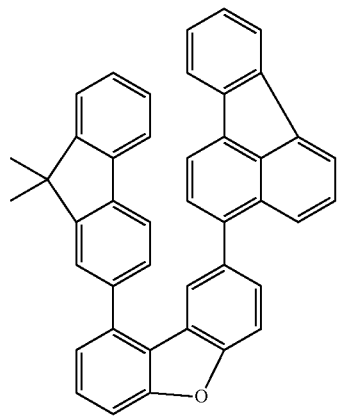 [SMILES: CC1(C)c2ccccc2-c2ccc(-c3cccc4oc5ccc(-c6ccc7c8c(cccc68)-c6ccccc6-7)cc5c34)cc21]

i1

The invention claimed is:

1. A host or matrix material for a light emitting layer comprising a compound of the formula (1) or (2),

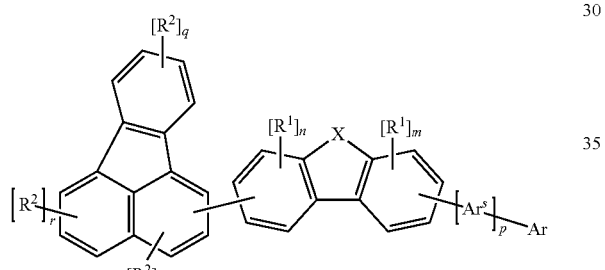

formula (1)

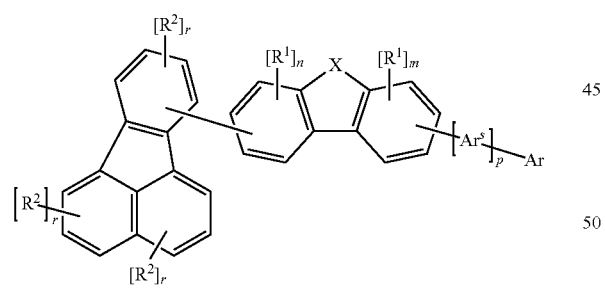

formula (2)

where the following applies to the symbols and indices used:

X is O or S;

$Ar^S$ is an aromatic or heteroaromatic ring system selected from the group consisting of formulae ($Ar^S$-1), ($Ar^S$-2), ($Ar^S$-6) to ($Ar^S$-13), $Ar^S$-1

-continued

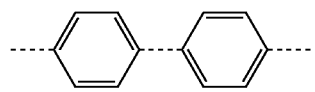
$Ar^S$-2

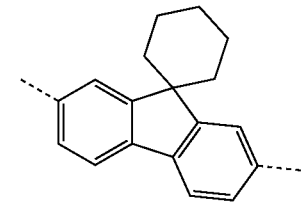
$Ar^S$-6

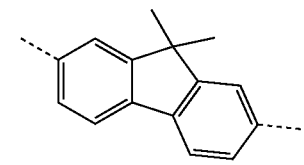
$Ar^S$-7

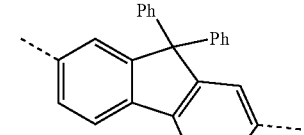
$Ar^S$-8

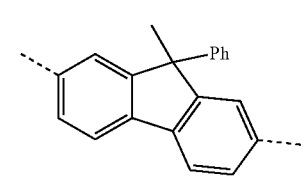
$Ar^S$-9

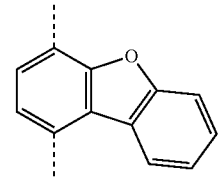
$Ar^S$-10

141

-continued

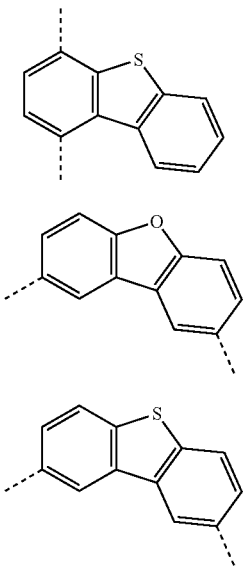

Ar<sup>s</sup>-11

Ar<sup>s</sup>-12

Ar<sup>s</sup>-13 where the dashed bonds indicates the bonds to the phenyl group of the heterocycle comprising X and to the group Ar as depicted in formula (1) or (2), and where the groups may be substituted at each free position by a group $R^3$;
Ar is a group of formula (Ar-1),

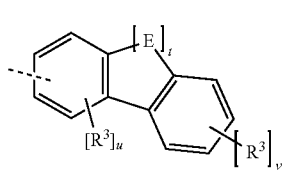

formula (Ar-1)

where the dashed line represents the bond to $Ar^S$ or, if $Ar^S$ is absent, to the phenyl group of the heterocycle comprising X as depicted in formula (1) or (2);
E is O, S, $C(R^0)_2$;
$R^0$ are on each occurrence, identically or differently, H, D, F, Cl, Br, I, CHO, C(=O)Ar$^1$, P(=O)(Ar$^1$)$_2$, S(=O)Ar$^1$, S(=O)$_2$Ar$^1$, (R$^4$)C=C(R$^4$)Ar$^1$, CN, NO$_2$, N(R$^4$)$_2$, Si(R$^4$)$_3$, B(OR$^4$)$_2$, B(R$^4$)$_2$, B(N(R$^4$)$_2$)$_2$, OSO$_2$R$^4$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which is optionally substituted by one or more radicals R$^4$, where one or more, CH$_2$ groups is optionally replaced by (R$^4$)C=C(R$^4$), C≡C, Si(R$^4$)$_2$, Ge(R$^4$)$_2$, Sn(R$^4$)$_2$, C=O, C=S, C=Se, P(=O)(R$^4$), SO, SO$_2$, N(R$^4$), O, S or CON(R$^4$) and where one or more H atoms is optionally replaced by D, F, Cl, Br, I, CN or NO$_2$, or an aromatic or heteroaromatic ring system having 5 to 60 aromatic ring atoms, which may in each case be substituted by one or more radicals R$^4$, or an aryloxy or heteroaryloxy group having 5 to 60 aromatic ring atoms, which is optionally substituted by one or more radicals R$^4$; two adjacent substituents R$^0$, two or more adjacent substituents R$^1$ and/or two or more adjacent substituents R$^3$ may also form a mono- or polycyclic, aliphatic or aromatic or heteroaromatic ring system with one another;
$R^1$, $R^2$ and $R^3$ are selected, identically or differently on each occurrence, from the group consisting of H, D, F, CN, a straight-chain alkyl or alkoxy group having 1 to 10 C atoms or a branched or cyclic alkyl or alkoxy group having 3 to 10 C atoms, each of which is optionally substituted by one or more radicals R$^4$, where one or more non-adjacent CH$_2$ groups is optionally replaced by O and where one or more H atoms is optionally replaced by F;
$Ar^1$ is on each occurrence, identically or differently, an aromatic or heteroaromatic ring system having 5 to 24 aromatic ring atoms, which may in each case be substituted by one or more radicals R$^4$;
$R^4$ is on each occurrence, identically or differently selected from the group consisting of H, D, F, Cl, Br, I, CN, Si(R$^5$)$_3$, a straight-chain alkyl, alkoxy or thioalkyl group having 1 to 40 C atoms or a branched or cyclic alkyl, alkoxy or thioalkyl with 3-40 C-atoms which is optionally substituted by one or more radicals R$^5$, wherein each one or more non-adjacent CH$_2$ groups by is optionally replaced C(R$^5$)=C(R$^5$), Si(R$^5$)$_2$, C=NR$^5$, P(=O)(R$^5$), SO, SO$_2$, NR$^5$, O, S or CONR$^5$ and where one or more H atoms is optionally replaced by D, F, Cl, Br or I, an aromatic or heteroaromatic ring system having 6 to 40 carbon atoms which is optionally substituted by one or more radicals R$^5$, an aryloxy group having 5 to 40 aromatic ring atoms which is optionally substituted by one or more radicals R$^5$, or an aralkyl group having 5 to 40 aromatic ring atoms which is optionally substituted by one or more radicals R$^5$, where optionally two or more adjacent substituents R$^4$ can form a mono- or polycyclic, aliphatic, aromatic or heteroaromatic ring system with one another;
$R^5$ is selected from the group consisting of H, D, F, an aliphatic hydrocarbon radical having 1 to 20 carbon atoms or an aromatic or heteroaromatic ring system having 5 to 30 C atoms, wherein two or more adjacent substituents R$^5$ can form a mono- or polycyclic, aliphatic, aromatic or heteroaromatic ring system with one another;
m, n, r, u are each, identically or differently, 0, 1, 2 or 3;
p is 0 or 1;
t is 1;
q, v are each, identically or differently, 0, 1, 2, 3 or 4;
s is 0, 1 or 2.

2. The host or matrix material according to claim 1, wherein p is 0.

3. The host or matrix material according to claim 1, wherein the compound is a compound of formulae (1-1) or (2-1),

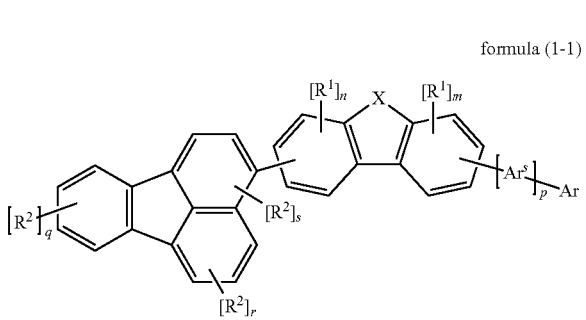

formula (1-1)

-continued
formula (2-1)
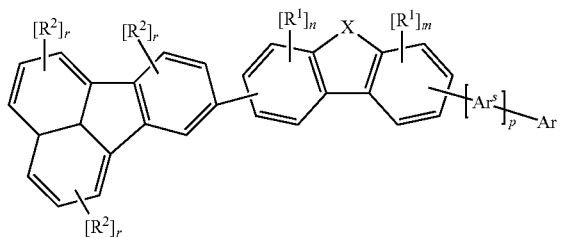
where the symbols and indices used have the same meanings as given in claim 1.
4. The host or matrix material according to claim 1, wherein the compound is a compound of formulae (1-1-1) to (2-1-4),
formula (1-1-1)
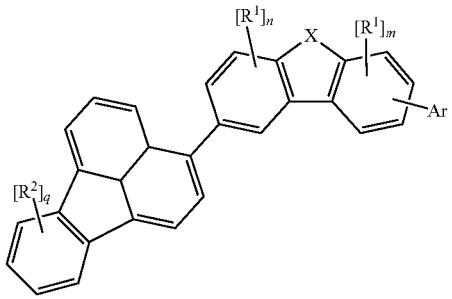
formula (1-1-2)
formula (1-1-3)
formula (1-1-4)
formula (2-1-1)
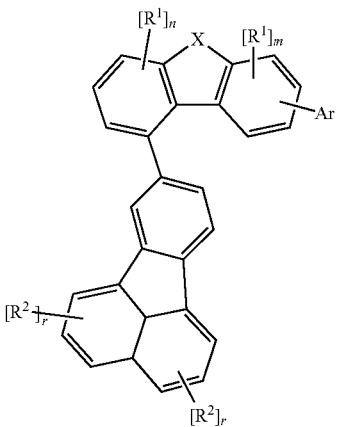
formula (2-1-2)
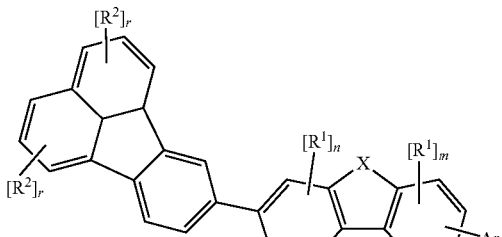
formula (2-1-3)
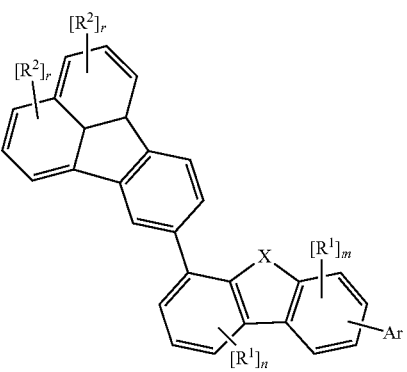

formula (2-1-4)
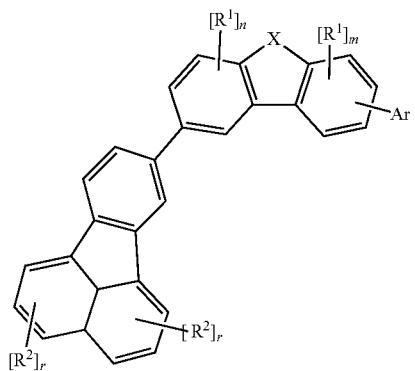
where the symbols and indices used have the same meanings as given in claim 1.
5. The host or matrix material according to claim 1, wherein the compound is a compound of formulae (1-1-1-a) to (2-1-4-d),
formula (1-1-1-a)
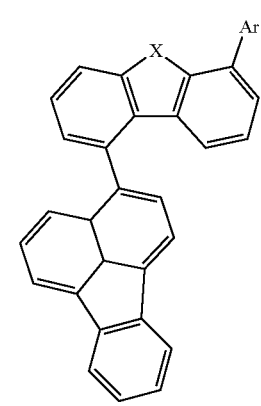
formula (1-1-1-b)
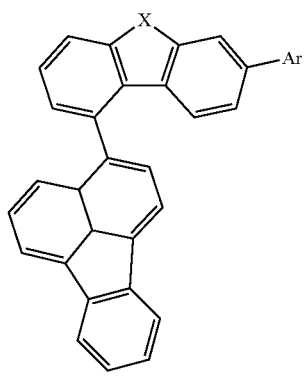
formula (1-1-1-c)
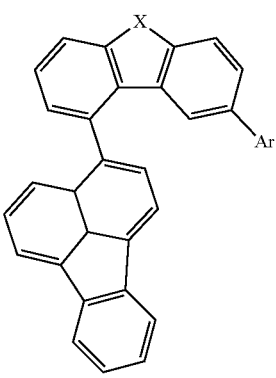
formula (1-1-1-d)
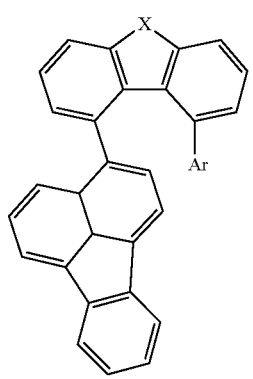
formula (1-1-2-a)
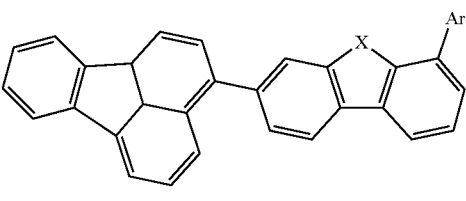
formula (1-1-2-b)
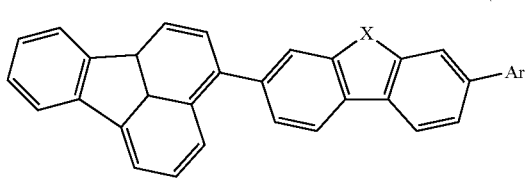
formula (1-1-2-c)
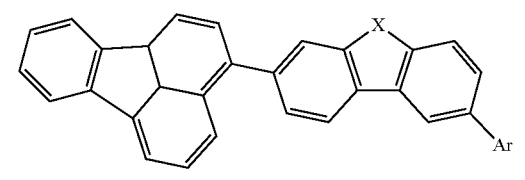
formula (1-1-2-d)
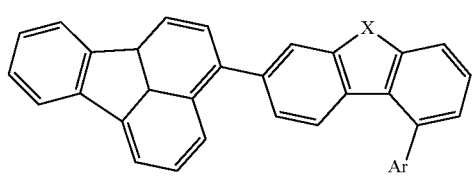

formula (1-1-3-a)
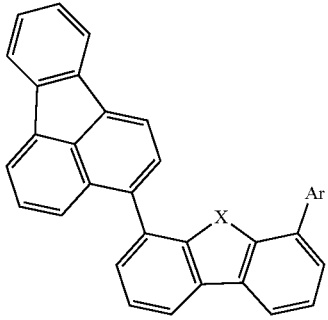
formula (1-1-3-b)
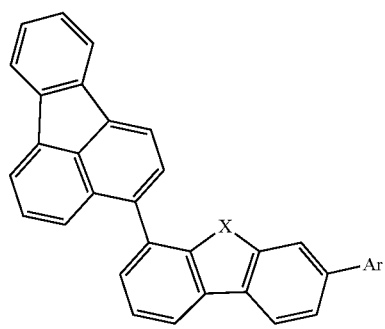
formula (1-1-3-c)
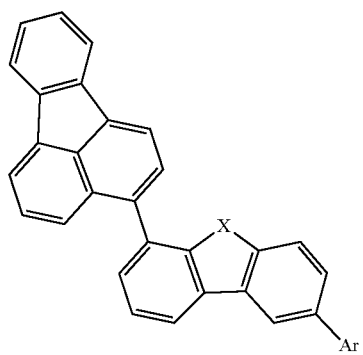
formula (1-1-3-d)
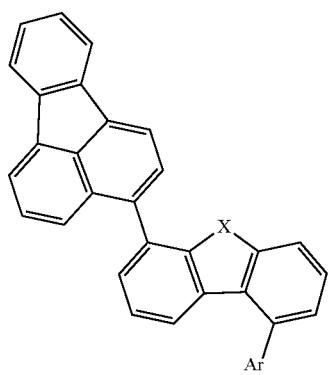
formula (1-1-4-a)
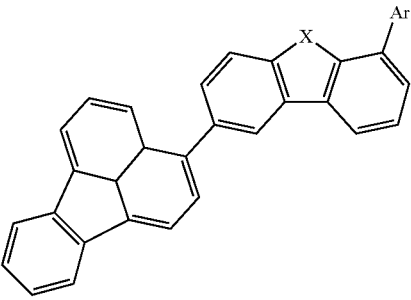
formula (1-1-4-b)
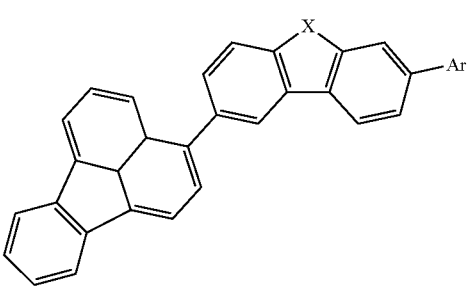
formula (1-1-4-c)
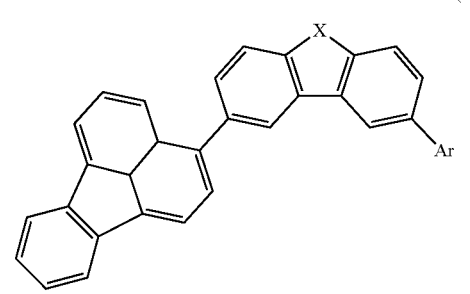
formula (1-1-4-d)
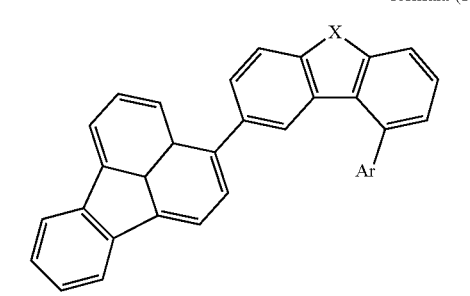
formula (2-1-1-a)
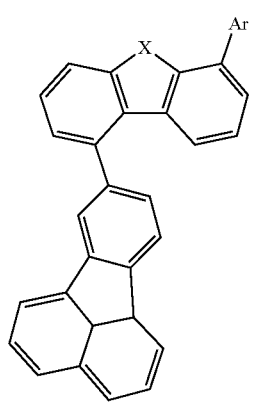

formula (2-1-1-b)
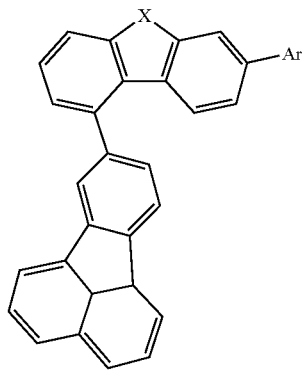
formula (2-1-1-c)
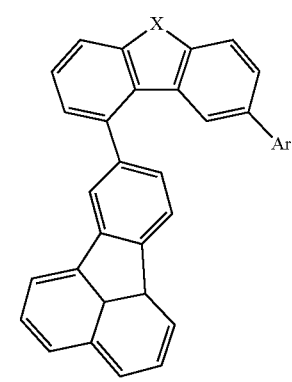
formula (2-1-1-d)
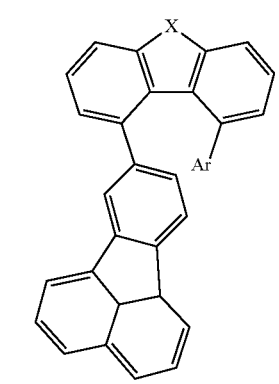
formula (2-1-2-a)
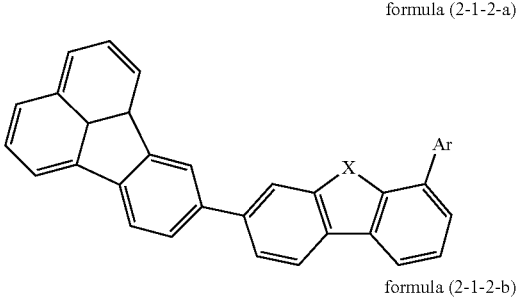
formula (2-1-2-b)
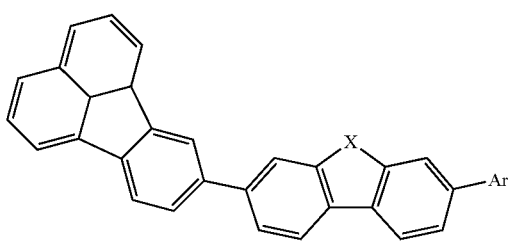
formula (2-1-2-c)
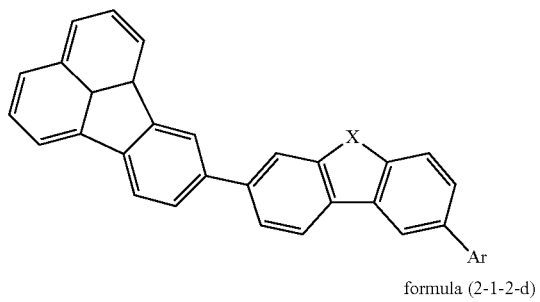
formula (2-1-2-d)
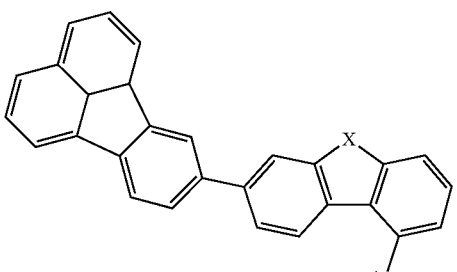
formula (2-1-3-a)
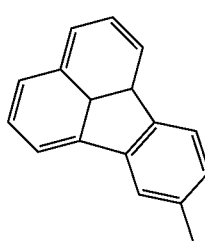
formula (2-1-3-b)
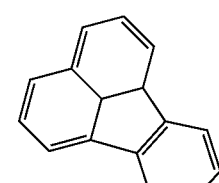
formula (2-1-3-c)
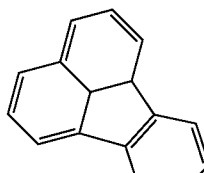

-continued formula (2-1-3-d)

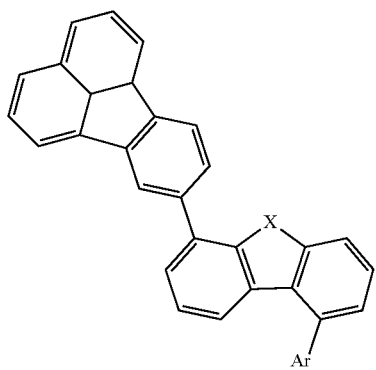

formula (2-1-4-a)

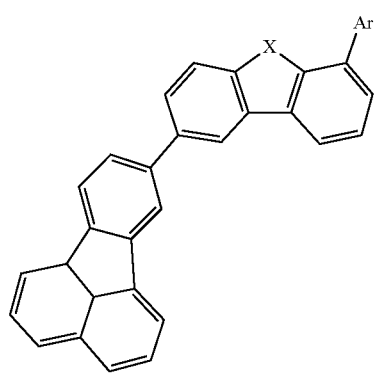

formula (2-1-4-b)

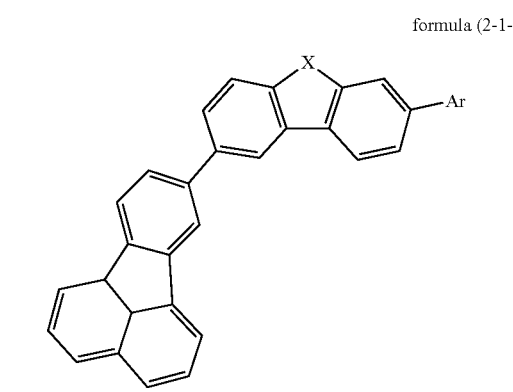

formula (2-1-4-c)

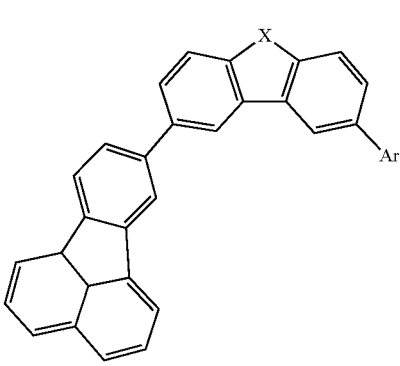

-continued formula (2-1-4-d)

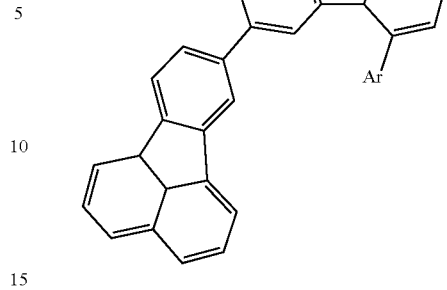

where the symbols and indices used have the same meanings as given in claim 1.

6. The host or matrix material according to claim 1, wherein $R^1$, $R^2$, $R^3$ are selected, identically or differently on each occurrence, from the group consisting of H, D, F, CN, a straight-chain alkyl group having 1 to 5 C atoms or a branched or cyclic alkyl group having 3 to 5 C atoms, each of which is optionally substituted by one or more radicals $R^4$, where one or more H atoms is optionally replaced by F.

7. The host or matrix material according to claim 1, wherein $R^0$ is selected on each occurrence, identically or differently, from the group consisting of H, D, F, CN, a straight-chain alkyl or alkoxy group having 1 to 10 C atoms or a branched or cyclic alkyl or alkoxy group having 3 to 10 C atoms, each of which is optionally substituted by one or more radicals $R^4$, where in each case one or more non-adjacent $CH_2$ groups is optionally replaced by O and where one or more H atoms is optionally replaced by D, F or CN, an aromatic or heteroaromatic ring system having 5 to 24 aromatic ring atoms, which may in each case be substituted by one or more radicals $R^4$, where two substituents $R^0$ may optionally form a mono- or polycyclic, aliphatic or aromatic or heteroaromatic ring system.

8. An organic electroluminescent device comprising the host or matrix material according to claim 1 is employed as a material for phosphorescent or fluorescent emitters, and the compounds of the formula (1) or (2) are further employed as a material in an electron-blocking or exciton-blocking material, a hole-blocking material, or an electron-transport material.

9. The host or matrix according to claim 1, wherein the host or matrix is used for phosphorescent or fluorescent emitters.

10. The host or matrix according to claim 1, wherein the host or matrix is used for phosphorescent emitters.

11. The host or matrix material according to claim 1, wherein Ar is selected from the groups of the following formulae (Ar-19) to (Ar-38),

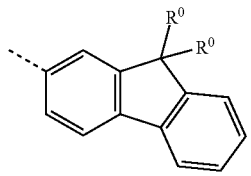

Ar-19

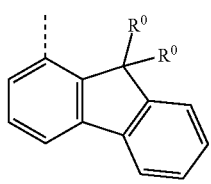 Ar-20
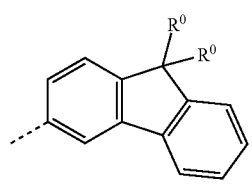 Ar-21
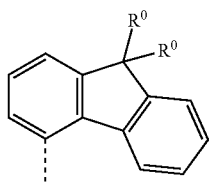 Ar-22
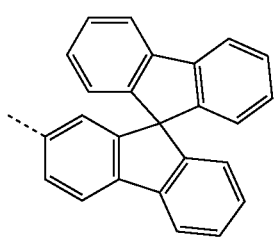 Ar-23
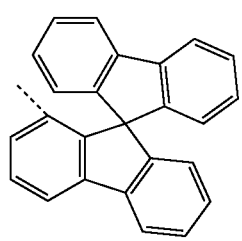 Ar-24
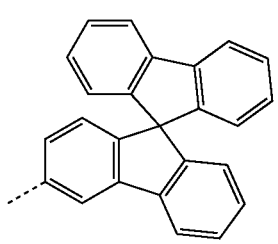 Ar-25
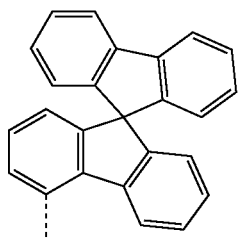 Ar-26
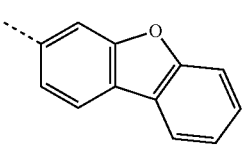 Ar-27
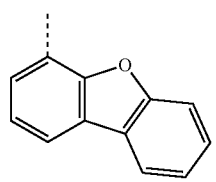 Ar-28
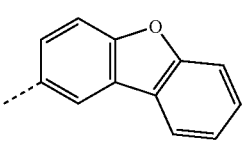 Ar-29
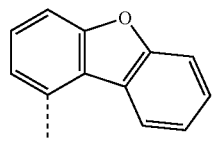 Ar-30
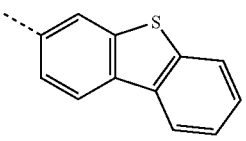 Ar-31
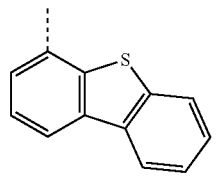 Ar-32
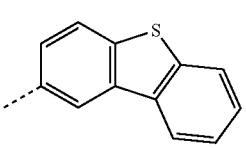 Ar-33

Ar-34
Ar-35
Ar-36
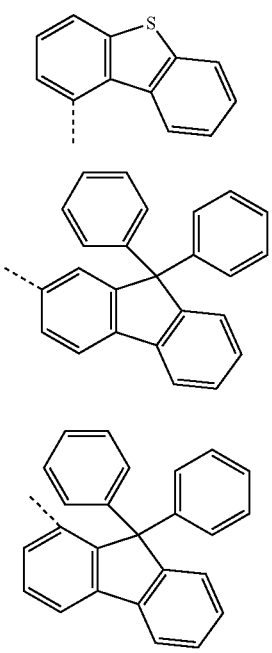
Ar-37
Ar-38
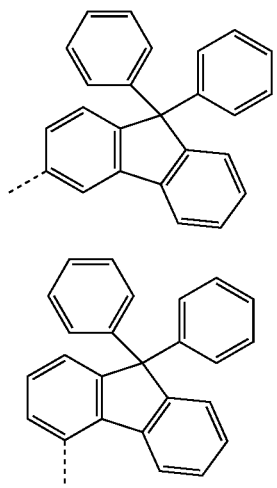
where $R^0$ has the same meaning as in claim 1 and where the groups of formulae (Ar-2) to (Ar-38) is optionally substituted by one or more radicals $R^3$ as defined in claim 1, at any free position.
\* \* \* \* \*